US009599618B2

(12) United States Patent
Imaizumi et al.

(10) Patent No.: US 9,599,618 B2
(45) Date of Patent: *Mar. 21, 2017

(54) METHOD, APPARATUS, SYSTEM, PROGRAM, AND COMPUTER-READABLE RECORDING MEDIUM FOR EVALUATING COLORECTAL CANCER

(75) Inventors: Akira Imaizumi, Kawasaki (JP); Toshihiko Ando, Kawasaki (JP); Naoyuki Okamoto, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 187 days.

This patent is subject to a terminal disclaimer.

(21) Appl. No.: 12/487,009

(22) Filed: Jun. 18, 2009

(65) Prior Publication Data

US 2010/0009401 A1    Jan. 14, 2010

Related U.S. Application Data

(63) Continuation of application No. PCT/JP2007/074270, filed on Dec. 18, 2007.

(30) Foreign Application Priority Data

Dec. 21, 2006 (JP) ................... 2006-344935

(51) Int. Cl.
G01N 33/48 (2006.01)
G01N 33/574 (2006.01)

(52) U.S. Cl.
CPC . *G01N 33/57419* (2013.01); *G01N 33/57488* (2013.01)

(58) Field of Classification Search
CPC ............................................. G01N 33/57419
USPC .......................................................... 702/19
See application file for complete search history.

(56) References Cited

U.S. PATENT DOCUMENTS

| | | | |
|---|---|---|---|
| 6,059,724 A | 5/2000 | Campell et al. | |
| 6,300,136 B1 | 10/2001 | Koch et al. | |
| 6,631,330 B1 | 10/2003 | Poynard | |
| 6,964,850 B2 | 11/2005 | Bevilacqua et al. | |
| 8,244,476 B2 | 8/2012 | Zhang et al. | |
| 2004/0039553 A1 | 2/2004 | Poynard | |
| 2006/0170928 A1 | 8/2006 | Masilamani et al. | |
| 2007/0281895 A1 | 12/2007 | Crockard et al. | |
| 2008/0147368 A1 | 6/2008 | Sugimoto et al. | |
| 2008/0154515 A1 | 6/2008 | Zhang et al. | |
| 2008/0305962 A1 | 12/2008 | Wirtz | |
| 2009/0046286 A1 | 2/2009 | Masilamani et al. | |
| 2009/0075284 A1 | 3/2009 | Chinnaiyan et al. | |
| 2009/0253116 A1 | 10/2009 | Takahashi et al. | |
| 2010/0004871 A1 | 1/2010 | Goldknopf | |
| 2010/0009402 A1 | 1/2010 | Imaizumi et al. | |
| 2010/0017144 A1 | 1/2010 | Imaizumi et al. | |
| 2010/0017145 A1 | 1/2010 | Imaizumi et al. | |
| 2011/0035156 A1 | 2/2011 | Imaizumi et al. | |
| 2011/0091924 A1 | 4/2011 | Imaizumi et al. | |
| 2011/0138889 A1 | 6/2011 | Okamoto et al. | |
| 2011/0143444 A1 | 6/2011 | Muramatsu et al. | |
| 2011/0282585 A9 | 11/2011 | Zhang et al. | |

FOREIGN PATENT DOCUMENTS

| | | |
|---|---|---|
| CN | 1315998 A | 10/2001 |
| CN | 1367830 A | 9/2002 |
| CN | 1878876 A | 12/2006 |
| EP | 1 570 779 A1 | 9/2005 |
| EP | 1 862 797 A1 | 12/2007 |
| IN | 209084 B | 9/2007 |
| JP | 61-126472 A | 6/1986 |
| JP | 2005-508505 A | 3/2005 |
| JP | 5746811 B2 | 7/2015 |
| WO | WO 97/48982 A1 | 12/1997 |
| WO | WO 00/04149 A2 | 1/2000 |
| WO | WO 00/20587 A | 4/2000 |
| WO | WO 00/65472 A1 | 11/2000 |
| WO | WO 02/16949 A1 | 2/2002 |
| WO | WO 2004/052191 A1 | 6/2004 |
| WO | WO 2006/098192 A1 | 9/2006 |
| WO | WO 2006/129513 A1 | 12/2006 |
| WO | WO 2007/030928 A2 | 3/2007 |
| WO | WO 2007/107334 A1 | 9/2007 |
| WO | WO 2008/016111 A | 2/2008 |
| WO | WO 2008/036691 A2 | 3/2008 |
| WO | WO 2008/075662 A1 | 6/2008 |
| WO | WO 2008/075664 A1 | 6/2008 |
| WO | WO 2009/099005 A1 | 8/2009 |
| WO | WO 2009/110517 A1 | 9/2009 |
| WO | WO 2009/154296 A1 | 12/2009 |
| WO | WO 2009/154297 A1 | 12/2009 |

OTHER PUBLICATIONS

Vecer et al., "Tissue amino acids in patients with colorectal carcinoma", Vnitr Lek., 1998, vol. 44, No. 4, abstract.*
Ando, Toshihiko, "Development of Health Check Method Based on Blood Amino Acid Concentration," Chemistry & Chemical Industry, Jan. 1, 2007, 60(1):40-41, with English translation, 5 pages.
Cascino et al., "Plasma Amino Acid Imbalance in Patients with Lung and Breast Cancer," Anticancer Research, 1995, 15:507-510.
Elling et al., "Freie Aminosauren im normalen und karzinomatosen Ovarialgewebe in Korrelation zum Seramspiegel-tumordiagnostische Moglichkeiten," Zent. Bl. Gynakol., 1987, 109:1013-1022, English abstract on first page.
Elling et al., "Therapiemonitoring bei Patientinnen mit Korpuskarzinom mit und ohne Progression durch freie Serumaminosaeuren," Zent. Bl. Gynakol., 1989, 111:1224-1230, English abstract on first page.
Evans et al., "Perturbations in Plasma Amino Acid Profiles in Small Cell Lung Cancer (SCLC) and their Response to Treatment," Proc. Amer. Assoc. Cancer Res. Ann. Meet., 1988, 29:18, No. 69.
Fukasawa et al., "Serum free amino acid content in hamsters with cheek pouch carcinoma," Jpn. J. Oral Biol., Oct. 20, 1992, 34:555-559, with English translation, 10 pages.

(Continued)

*Primary Examiner* — Jerry Lin
(74) *Attorney, Agent, or Firm* — Foley & Lardner LLP

(57) ABSTRACT

According to the method of evaluating colorectal cancer of the present invention, amino acid concentration data on the concentration value of amino acid in blood collected from a subject to be evaluated is measured, and a colorectal cancer state in the subject is evaluated based on the concentration value of at least one of Arg, Cys, Orn, Trp, Glu, ABA, Val, Phe, Leu, Gln, Ile and His contained in the measured amino acid concentration data of the subject.

44 Claims, 48 Drawing Sheets

(56) References Cited

OTHER PUBLICATIONS

Fukui et al., "Study onf Branched Chain Amino Acid Metabolism in Last-Stage Hepatic Cancer," Journal of Clinical and Experimental Medicine (Rinsho to Kenkyu), Apr. 1989, 66(4):1183-1187, with English translation, 16 pages.

Hirayama et al., "Plasma Amino Acid Patterns in Hepatocellular Carcinoma," Biochemical Medicine and Metabolic Biology, 1987, 38(2):127-133.

Inoue et al., "Changes of Plasma Free Amino Acids in Hepatocellular Carcinoma: Clinical and Experimental Studies on Evaluation of Tyr/Phe Molar Ratio," J. Iwate Med. Assoc., Jun. 1988, 40(3):351-361, with English translation, 20 pages.

Kimura et al., "The Application of Amino Acid Informatics," Reports on the Research Committee of Essential Amino Acids, Japan, 2006, 177:28-31, with partial English translation, 1 page.

Kwon et al., "Plasma Free Amino Acids and Biochemical Parameters for Nutrition Assessment in Gastric Cancer Patients," Journal of Surgery and Metabolism/Nutrition, Apr. 1995, 29(2):129-134, with English translation, 11 pages.

Lee et al., "Identification of optimal classification functions for biological sample and state discrimination from metabolic profiling data," Bioinformatics, 2004, 20(6):959-969.

Murakami et al., "Changes of Amino Acids in Tumor-Bearing Rats with Total Parenteral Nutrition," JJPEN, Aug. 15, 1987, 9(4):615-621, with English translation, 12 pages.

Nefyodov et al., "Amino Acids and their Derivatives in Blood Plasma of Patients with Breast Cancer Treated with Ukrain. Part V," Drugs Exptl. Clin. Res., 1996, 22(3-4-5):155-157.

Okamoto et al., "Development of New Lung Cancer Screening Method by Plasma Free Amino Acid Profile," $65^{th}$ Annual Meeting of the Japan Cancer Association, Aug. 28, 2006, 287:O-565, with English translation, 2 pages.

Okamoto et al., "Early Detection of Breast Cancer using Plasma Free Amino Acid Profiles," $66^{th}$ Annual Meeting of the Japan Cancer Association, Aug. 25, 2007, 66:517, P-1210.

Okuyama et al., "Study on plasma amino acids pattern in liver diseases by using multivariate analysis," Journal of Liver, Gall-Bladder and Pancreas, 1987, 15(1):111-117, with partial English translation, 1 page.

Proenza et al., "Breast and lung cancer are associated with a decrease in blood cell amino acid content," Journal of Nutritional Biochemistry, 2003, 14:133-138.

Rivera et al,. "Blood Amino Acid Compartmentation in Mice Bearing Lewis Lung Carcinoma," Cancer Research, Nov. 1, 1987, 47(21):5644-5646.

Shimazaki et al., "Free Amino Acids in Normal and Tumorous Tissues of Human Kidney, Bladder, and Prostate," GANN, Oct. 1974, 65(5):455-457.

Wilson et al., "Free Serum Amino Acids in Patients with Advanced Cervical Carcinoma," Gynecologic Oncology, 1976, 4(3):311-313.

Kubota et al., "Amino Acid Profiles Correlate Diagnostically with Organ Site in Three Kinds of Malignant Tumors," Cancer, May 1, 1992, 69(9):2343-2348.

Supplementary European Search Report dated Dec. 8, 2010, in corresponding EP 07850758.9, 9 pages.

Lee et al., "Plasma Amino Acid Levels in Patients with Colorectal Cancers and Liver Cirrhosis with Hepatocellular Carcimona," Hepato-Gastroenterology, Sep.-Oct. 2003, 50(53):1269-1273.

International Search Report mailed Feb. 5, 2008, in prior PCT/JP2007/074270, 5 pages.

Cynober, Luc A., Ed., Metabolic and Therapeutic Aspects of Amino Acids in Clinical Nutrition, $2^{nd}$ Ed., 2004, 339-355 and 689-704.

Iwagaki al., "Observation on the Plasma Amino Acids of Patients with Colorectal Cancer," Journal of Japan Society of Coloproctology, 1991, 44(6):917-922, with English translation of Results, 1 page.

Noguchi et al., "Network analysis of plasma and tissue amino acids and the generation of an amino index for potential diagnostic use," Am. J. Clin. Nutr., 2006, 83(Supp):513S-519S.

Park et al., "Arginine Metabolism in Benign and Malignant Disease of Breast and Colon: Evidence for Possible Inhibition of Tumor-Infiltrating Macrophages," Nutrition, May/Jun. 1991, 7(3):185-188.

Vissers et al., "Plasma arginine concentrations are reduced in cancer patients: evidence for arginine deficiency," Am. J. Clin. Nutr., 2005, 81:1142-1146.

Caballero et al., "Plasma amino acid concentrations in healthy elderly men and women," Am. J. Clin. Nutr., 1991, 53:1249-1252.

Cascino et al., "Increased Plasma Free Tryptophan Levels in Human Cancer: A Tumor Related Effect?" Anticancer Research, 1991, 11:1313-1316.

Heber et al., "Metabolic Abnormalities in the Cancer Patient," Cancer, 1985, 55:225-229.

Lai et al., "Plasma free amino acid profile in cancer patients," Seminars in Cancer Biology, 2005, 15:267-276.

Landuyt et al., "Differential protein expression profile in gastrointestinal stromal tumors," Amino Acids, 2004 27:335-337.

Laviano et al., "Tumor-Induced Changes in Host Metabolism: A Possible Role for Free Tryptophan as a Marker of Neoplastic Disease," Developments in Tryptophan and Serotonin Metabolism, Allegri et al. Eds.; 2003, 363-366.

Mellor et al., "IDO Expression by Dendritic Cells: Tolerance and Tryptophan Catabolism," Nature Reviews, Oct. 2004, 4:762-774.

Naini et al. "Preoperative and Postoperative Levels of Plasma Protein and Amino Acid in Esophageal and Lung Cancer Patients," Cancer, 1988, 62:355-360.

Norton et al., "Fasting Plasma Amino Acid Levels in Cancer Patients," Cancer, 1985, 56:1181-1186.

Rodriguez et al., "Arginase I in myeloid suppressor cells is induced by COX-2 in lung carcinoma," J. Exp. Med., Oct. 3, 2005, 202(7):931-939.

Shangyi et al., "Preliminary Observations on Free Amino Acid Values of Plasma of Patients with Ovarian Cancer and Uterine cervix cancer," Chinese Journal of Clinical Oncology, Dec. 31, 1994, 21:94, with English abstract.

Vissers et al., "Plasma arginine concentrations are reduced in cancer patients: evidence for arginine deficiency?" Am. J. Clin. Nutr., 2005, 81:1142-1146.

Fortunato et al., "Multivariate Discriminant Function Based on Six Biochemical Markers in Blood Can Predict the Cirrhotic Evolution of Chronic Hepatitis," Clinical Chemistry, 2001, 47(9):1696-1700.

Hirai, Yoshinori, "A Study of Amino Acid Metabolism in Patients with Gastric Cancer," Journal of Japan Surgical Society, Jul. 1, 1965, 66:983-1013, with English translation.

Kwon et al., "Plasma Free Amino Acids and Various Nutritional Indices Analyzed in Relation to Growth of Gastric Cancer," Japanese Journal of Surgical Metabolism and Nutrition, Apr. 1995, 29(2):129-134, with English translation.

Elling et al., "Therapy monitoring in endometrial carcinomas with and without progression by free serum amino acids," Zentralblatt fur Gynakologie, 1989, 111(18):1224-1230.

Elling et al., "Free amino acids in normal and ovarian cancer tissue in correlation to serum levels-tumour diagnostic possibilities," Zentralblatt fur Gynakologie, 1987, 109(16):1013-1022.

Miyake, Makoto, "Clinical Studies on the Metabolism of Plasma Amino Acids in Various Diseases," Journal of the Nagoya City University Medical Association, 1977, 28(2):308-351, with English translation.

Muscaritoli et al., "Plasma Amino Acid Profile in Cancer Patients: Moving Toward a New Set of Tumor Markers?", Nutritional Support in Cancer and Transplant Patients, 2001, 107-118.

Heintzelman et al., "Characterization of the Autofluorescence of Polymorphonuclear Leukocytes, Mononuclear Leukocytes and Cervical Epithelial Cancer Cells for Improved Spectroscopic Discrimination of Inflammation from Dysplasia," Photochemistry and Photobiology, 2000, 71(3):327-332.

Hirayama et al., "Quantitative Metabolome Profiling of Colon and Stomach Cancer Microenvironment by Capillary Electrophoresis Time-of-Flight Mass Spectrometry," Cancer Res., 2009, 69(11):4918-4925.

Leichtle et al., "Serum amino acid profiles and their alterations in colorectal cancer," Metabolomics, 2012, 8(4):643-653.

(56) References Cited

OTHER PUBLICATIONS

Qiu et al., "Serum Metabolite Profiling of Human Colorectal Cancer Using GC-TOFMS and UPLC-QTOFMS," Journal of Proteome Research, 2009, 8(10):4844-4850.

Selamnia et al., "De novo synthesis of arginine and ornithine from citrulline in human colon carcinoma cells: metabolic fate of L-ornithine," Biochimica et Biophysica Acta, 1998, 1425(1):93-102.

Tan et al., "Metabonomics Identifies Serum Metabolite Markers of Colorectal Cancer," Journal of Proteome Research, 2013, 12(6):3000-3009.

Miyagi et al., "Clinical Utility of AMINOINDEX Cancer Screening (AICS) for early detection of various cancers in comparison with detection using tumor markers," Physical Examination, 2014, 29:585-591, with English translation.

Miyagi et al., "Plasma Free Amino Acid Profiling of Five Types of Cancer Patients and Its Application for Early Detection," PLoS One, Sep. 2011, 6:e24143, pp. 1-12.

Okamoto et al., "Alternative method for the diagnosis of early breast cancer using plasma free amino acid profiles," Breast, Mar. 2007, 16(supp.1):S22, Abstract P34.

\* cited by examiner (BASIC PRINCIPLE OF THE INVENTION)

FIG.7

| USER ID | USER PASSWORD | NAME | ORGANI-ZATION ID | DEPART-MENT ID | DEPART-MENT NAME | E-MAIL ADDRESS | ... |
|---|---|---|---|---|---|---|---|
| : | : | : | : | : | : | : | : |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| : | : | : | : | : | : | : |

| INDIVIDUAL (SAMPLE) NO. | COLORECTAL CANCER STATE INDEX DATA (T) ||||  AMINO ACID CONCENTRATION DATA $_{106c}$ |||||| 
|---|---|---|---|---|---|---|---|---|---|---|
| | $T_1$ | $T_2$ | $T_3$ | ... | Gly | Leu | Val | Ile | Phe | ... |
| A-1 | 23.4 | 62.5 | 37.1 | ... | 9.5 | 11.2 | 2.7 | 8.5 | 4.9 | ... |
| A-2 | 27.5 | 66.1 | 39.5 | ... | 8.5 | 10.5 | 3.9 | 9.8 | 6.1 | ... |
| ... | ... | ... | ... | ... | ... | ... | ... | ... | ... | . |

FIG.10

| INDIVIDUAL (SAMPLE) NO. | COLORECTAL CANCER STATE INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | ⋮ | ⋮ | ⋮ | ⋮ |

| RANK | CANDIDATE MULTIVARIATE DISCRIMINANT |
|---|---|
| 1 | $F_1(Gly, Leu, Phe, ...)$ |
| 2 | $F_2(Gly, Leu, Phe, ...)$ |
| 3 | $F_3(Gly, Leu, Phe, ...)$ |
| ⋮ | ⋮ |

FIG.12

| RANK | CANDIDATE MULTIVARIATE DISCRIMINANT | VERIFICATION RESULT |
|---|---|---|
| 1 | $F_k(Gly,Leu,Phe,...)$ | 1.22 |
| 2 | $F_m(Gly,Leu,Phe,...)$ | 2.28 |
| 3 | $F_l(Gly,Leu,Phe,...)$ | 2.95 |
| ⋮ | ⋮ | ⋮ |

| INDIVIDUAL (SAMPLE) NO. | COLORECTAL CANCER STATE INDEX DATA (T) | AMINO ACID CONCENTRATION DATA | | |
|---|---|---|---|---|
| | $T_2$ | Leu | Phe | ... |
| A-1 | 62.5 | 11.2 | 4.9 | ... |
| A-2 | 66.1 | 10.5 | 6.1 | ... |
| ⋮ | ⋮ | ⋮ | ⋮ | ⋮ |

| RANK | MULTIVARIATE DISCRIMINANT | THRESHOLD VALUE | VERIFICATION RESULT |
|---|---|---|---|
| 1 | $F_p(Phe,...)$ | 0.23 | 0.62 |
| 2 | $F_p(Gly,Leu,Phe)$ | -2.12 | 1.02 |
| 3 | $F_k(Gly,Leu,Phe,...)$ | 1.23 | 1.22 |
| ⋮ | ⋮ | ⋮ | ⋮ |

| INDIVIDUAL (SAMPLE) NO. | RANK | DISCRIMINANT VALUE |
|---|---|---|
| U-1 | 1 | 1.13 |
| ⋮ | ⋮ | ⋮ |

106f

| INDIVIDUAL (SAMPLE) NO. | AMINO ACID CONCENTRATION DATA | | | | DISCRIMINANT VALUE | EVALUATION RESULT |
|---|---|---|---|---|---|---|
| | Gly | Leu | Phe | ... | | |
| U-1 | 9.5 | 11.2 | 4.9 | ... | | |
| U-2 | 8.5 | 10.5 | 6.1 | ... | | |
| ⋮ | ⋮ | ⋮ | ⋮ | ⋮ | ⋮ | ⋮ |

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| 0.8 | 1.000 | 0.000 | 0.036 | 1.000 | 0.036 |
| 0.9 | 1.000 | 0.008 | 0.036 | 1.000 | 0.044 |
| 1 | 1.000 | 0.077 | 0.039 | 1.000 | 0.110 |
| 1.1 | 1.000 | 0.336 | 0.053 | 1.000 | 0.360 |
| 1.2 | 1.000 | 0.678 | 0.104 | 1.000 | 0.690 |
| 1.25 | 0.969 | 0.805 | 0.157 | 0.999 | 0.811 |
| 1.3 | 0.969 | 0.894 | 0.254 | 0.999 | 0.896 |
| 1.31 | 0.969 | 0.902 | 0.270 | 0.999 | 0.904 |
| 1.32 | 0.906 | 0.917 | 0.290 | 0.996 | 0.917 |
| 1.33 | 0.844 | 0.930 | 0.310 | 0.994 | 0.927 |
| 1.35 | 0.844 | 0.942 | 0.351 | 0.994 | 0.938 |
| 1.4 | 0.750 | 0.974 | 0.522 | 0.990 | 0.966 |
| 1.5 | 0.531 | 0.992 | 0.708 | 0.983 | 0.975 |
| 1.75 | 0.094 | 1.000 | 1.000 | 0.967 | 0.967 |
| 2 | 0.031 | 1.000 | 1.000 | 0.965 | 0.965 |

FIG.27

| No. | FORMULA | ROC_AUC |
|---|---|---|
| 1 | (Orn)/(Trp+His)+(ABA+Ile)/(Leu) | 0.9729212 |
| 2 | (Orn)/(Tyr+His)+(ABA+Ile)/(Leu) | 0.9707244 |
| 3 | (Tau)/(Gln)+(Orn+Ile)/(Leu+Trp) | 0.969769 |
| 4 | (Orn)/(Leu+His)+(Tau+Ile)/(Gln) | 0.968693 |
| 5 | (Orn)/(Tyr+Arg)+(ABA+Ile)/(Leu) | 0.9666317 |
| 6 | (Orn)/(Leu+Trp)+(Tau+Ile)/(Gln) | 0.9664128 |
| 7 | (Orn)/(His+Arg)+(ABA+Ile)/(Leu) | 0.965907 |
| 8 | (Cys)/(Gln)+(Orn+Ile)/(Leu+Trp) | 0.965842 |
| 9 | (Orn)/(Trp+His)+(Tau+ABA)/(Gln) | 0.965474 |
| 10 | (Orn+ABA+Ile)/(Leu+Tyr+His) | 0.9654162 |
| 11 | (Orn)/(His)+(Cys+ABA+Ile)/(Leu) | 0.9651655 |
| 12 | (Tau)/(Gln)+(Orn+Ile)/(Leu+His) | 0.9651238 |
| 13 | (Phe)/(Gln)+(Orn+Ile)/(Leu+Trp) | 0.9650727 |
| 14 | (Orn)/(Leu+His)+(Tau+Phe)/(Gln) | 0.9650532 |
| 15 | (Orn)/(Tyr+Trp)+(ABA+Ile)/(Leu) | 0.9646747 |
| 16 | (Orn)/(Leu+Arg)+(Tau+Ile)/(Gln) | 0.9645978 |
| 17 | (Orn)/(Trp+Arg)+(ABA+Ile)/(Leu) | 0.9644844 |
| 18 | (Orn)/(Trp+His)+(Cys+Ile)/(Leu) | 0.9640515 |
| 19 | (Orn)/(Leu+His)+(Cys+Ile)/(Gln) | 0.9640099 |
| 20 | (Orn)/(Leu+Trp)+(Cys+Ile)/(Gln) | 0.9639834 |
| 21 | (Tau)/(Gln)+(Orn+Ile)/(Leu+Arg) | 0.9637854 |
| 22 | (Orn)/(Trp+His)+(Cys+Tau)/(Gln) | 0.9631876 |
| 23 | (Orn+Cys+Ile)/(Leu+Trp+His) | 0.9630811 |
| 24 | (Orn)/(Leu+Trp)+(ABA+Ile)/(Gln) | 0.963068 |
| 25 | (Orn)/(Leu+Tyr)+(Tau+Ile)/(Gln) | 0.9627966 |

FIG.28

| No | FORMULA | ROC_AUC |
|---|---|---|
| 26 | (Orn)/(Leu+His)+(Cys+Phe)/(Gln) | 0.962194 |
| 27 | (Orn)/(Leu+Trp)+(Ile+Phe)/(Gln) | 0.9620874 |
| 28 | (Orn)/(Trp+His)+(Tau+Phe)/(Gln) | 0.9618648 |
| 29 | (Orn+ABA+Ile)/(Leu+Tyr+Trp) | 0.9616489 |
| 30 | (Orn)/(Tyr+Arg)+(Cys+Ile)/(Leu) | 0.9616003 |
| 31 | (Orn)/(Tyr+Trp)+(Cys+Ile)/(Leu) | 0.9615182 |
| 32 | (Orn)/(Trp+Arg)+(Cys+Ile)/(Leu) | 0.9610903 |
| 33 | (Orn)/(Trp+His)+(Cys+ABA)/(Gln) | 0.9610508 |
| 34 | (Orn)/(Leu+Tyr)+(ABA+Ile)/(Gln) | 0.9610204 |
| 35 | (Orn)/(Leu+Tyr)+(Cys+Ile)/(Gln) | 0.960809 |
| 36 | (Orn)/(Leu+His+Arg)+(Tau)/(Gln) | 0.9608005 |
| 37 | (Orn)/(Leu+His)+(Cys+Tau)/(Gln) | 0.9604735 |
| 38 | (Orn)/(His)+(Tau+ABA)/(Leu+Arg) | 0.9604524 |
| 39 | (Tau)/(Gln)+(Orn+Ile)/(Leu+Tyr) | 0.9604244 |
| 40 | (Orn)/(Trp+His+Arg)+(Tau)/(Gln) | 0.9604106 |
| 41 | (Orn+ABA+Ile)/(Leu+Trp+Arg) | 0.960349 |
| 42 | (Ile)/(Leu)+(Orn+ABA)/(Tyr+Arg) | 0.9602244 |
| 43 | (Ile)/(Leu)+(Orn+Cys)/(Trp+His) | 0.960211 |
| 44 | (Orn)/(Tyr+His)+(Cys+Ile)/(Leu) | 0.9601099 |
| 45 | (Orn)/(Trp+His)+(Tau+Asn)/(Gln) | 0.9600795 |
| 46 | (Orn)/(Trp+His)+(Tau+Met)/(Gln) | 0.9600456 |
| 47 | (Orn)/(Leu+Arg)+(Tau+Phe)/(Gln) | 0.9596603 |
| 48 | (Orn)/(His)+(Cys+Ile)/(Leu) | 0.9595391 |
| 49 | (Orn+Cys+Ile)/(Leu+Trp+Arg) | 0.9594953 |
| 50 | (Orn)/(Trp+Arg)+(Ile+Met)/(Leu) | 0.9594765 |

FIG.29

| No. | FORMULA | ROC_AUC |
|---|---|---|
| 51 | (Orn+ABA+Ile)/(Leu+Tyr+Arg) | 0.9593855 |
| 52 | (Orn)/(Leu+Arg)+(ABA+Ile)/(Gln) | 0.959356 |
| 53 | (Ile)/(Leu)+(Orn+ABA)/(Trp+Arg) | 0.95911 |
| 54 | (Orn)/(Leu+Arg)+(Cys+Ile)/(Gln) | 0.9590267 |
| 55 | (Orn)/(Tyr+His)+(Tau+ABA)/(Gln) | 0.9589905 |
| 56 | (Orn)/(His)+(Tau+Ile)/(Leu+Trp) | 0.9589676 |
| 57 | (Orn)/(His+Arg)+(Tau+ABA)/(Gln) | 0.9589056 |
| 58 | (Orn)/(Leu+Trp+His)+(Phe)/(Gln) | 0.9588068 |
| 59 | (Orn)/(Tyr+His)+(Cys+Tau)/(Gln) | 0.9585067 |
| 60 | (Orn)/(Trp+Arg)+(Ile+Phe)/(Leu) | 0.958397 |
| 61 | (Cys)/(Gln)+(Orn+Ile)/(Leu+Tyr) | 0.958313 |
| 62 | (Orn+Cys+Ile)/(Leu+Tyr+Trp) | 0.958144 |
| 63 | (Orn)/(Trp+His)+(Tau)/(Gln) | 0.9581115 |
| 64 | (Orn)/(Leu+Tyr)+(Ile+Phe)/(Gln) | 0.9581049 |
| 65 | (Orn)/(Leu+Arg)+(ABA+Phe)/(Gln) | 0.9580841 |
| 66 | (Orn)/(His+Arg)+(Cys+Tau)/(Gln) | 0.9580381 |
| 67 | (Ile)/(Leu)+(Orn+Cys)/(Trp+Arg) | 0.958025 |
| 68 | (Orn)/(Tyr+Arg)+(Ile+Met)/(Leu) | 0.9579553 |
| 69 | (Orn+Cys+Ile)/(Leu+Tyr+His) | 0.9579214 |
| 70 | (ABA)/(Gln)+(Orn+Ile)/(Leu+Tyr) | 0.9577225 |
| 71 | (Ile)/(Gln)+(Orn+ABA)/(Leu+Tyr) | 0.9577105 |
| 72 | (Ile)/(Leu)+(Orn+Cys)/(Tyr+Arg) | 0.9575719 |
| 73 | (Orn)/(Trp+His)+(ABA+Phe)/(Gln) | 0.9575658 |
| 74 | (Orn)/(Tyr+His+Arg)+(Tau)/(Gln) | 0.9575348 |
| 75 | (Ile)/(Leu)+(Orn+Cys)/(Tyr+His) | 0.9573973 |

FIG.30

| No. | FORMULA | ROC_AUC |
|---|---|---|
| 76 | (Orn)/(Tyr+His)+(Cys+ABA)/(Gln) | 0.957391 |
| 77 | (Orn)/(Trp+His)+(Tau+Glu)/(Gln) | 0.9572892 |
| 78 | (Tau)/(Gln)+(Orn+ABA)/(Tyr+His) | 0.9571975 |
| 79 | (Orn)/(Trp+His)+(Tau+Ile)/(Gln) | 0.9571792 |
| 80 | (Phe)/(Gln)+(Orn+Ile)/(Leu+Tyr) | 0.9571721 |
| 81 | (Orn+Cys+Ile)/(Leu+Tyr+Arg) | 0.95713 |
| 82 | (Orn)/(Trp+His)+(Cys)/(Leu+Arg) | 0.9569346 |
| 83 | (Orn)/(Leu+Tyr+Trp)+(Ile)/(Gln) | 0.9567362 |
| 84 | (Orn)/(Trp+His)+(Asn+ABA)/(Gln) | 0.9567113 |
| 85 | (Orn)/(His)+(Tau+Phe)/(Leu+Arg) | 0.9566877 |
| 86 | (Orn)/(Tyr+Trp+His)+(Tau)/(Gln) | 0.9566798 |
| 87 | (Orn)/(Trp+His)+(Tau)/(Tyr+Gln) | 0.9566094 |
| 88 | (Orn+Cys+Ile)/(Leu+His+Arg) | 0.9565604 |
| 89 | (Ile)/(Leu)+(Orn+Tau)/(Trp+Arg) | 0.9565497 |
| 90 | (Orn)/(Tyr+His)+(Tau+Phe)/(Gln) | 0.9565432 |
| 91 | (Orn)/(His+Arg)+(Tau+Phe)/(Gln) | 0.9565007 |
| 92 | (Orn)/(His)+(Tau+ABA)/(Trp+Arg) | 0.9564974 |
| 93 | (Orn+Cys)/(Leu+Tyr+Trp+Gln) | 0.956456 |
| 94 | (Orn)/(Trp+His)+(Tau)/(Leu+Gln) | 0.9564466 |
| 95 | (Orn)/(Leu+Arg)+(Cys+Phe)/(Gln) | 0.9563473 |
| 96 | (Ile)/(Gln)+(Orn+Cys)/(Leu+His) | 0.9563302 |
| 97 | (Orn+Tau+Ile)/(Leu+Trp+Arg) | 0.9562989 |
| 98 | (Orn)/(His)+(Tau+Ile)/(Leu+Arg) | 0.9561678 |
| 99 | (Orn)/(Leu+Trp+Arg)+(Tau)/(Gln) | 0.9560128 |
| 100 | (Orn)/(Tyr+His)+(Tau+Glu)/(Gln) | 0.9559924 |

FIG.32

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| 0.00001 | 1.000 | 0.007 | 0.036 | 1.000 | 0.043 |
| 0.0001 | 1.000 | 0.081 | 0.039 | 1.000 | 0.114 |
| 0.001 | 1.000 | 0.370 | 0.056 | 1.000 | 0.392 |
| 0.0025 | 0.969 | 0.530 | 0.072 | 0.998 | 0.546 |
| 0.005 | 0.969 | 0.647 | 0.093 | 0.998 | 0.658 |
| 0.01 | 0.938 | 0.750 | 0.123 | 0.997 | 0.756 |
| 0.025 | 0.875 | 0.844 | 0.174 | 0.994 | 0.846 |
| 0.05 | 0.875 | 0.920 | 0.292 | 0.995 | 0.919 |
| 0.075 | 0.844 | 0.942 | 0.351 | 0.994 | 0.938 |
| 0.1 | 0.844 | 0.956 | 0.415 | 0.994 | 0.952 |
| 0.25 | 0.688 | 0.987 | 0.667 | 0.988 | 0.976 |
| 0.5 | 0.438 | 0.995 | 0.778 | 0.979 | 0.975 |
| 0.75 | 0.344 | 0.998 | 0.846 | 0.976 | 0.974 |
| 1 | 0.000 | 1.000 | 0.000 | 0.964 | 0.964 |

FIG.33

| No. | FORMULA | ROC_AUC |
|---|---|---|
| 1 | '1.0597+0.19024*Orn-0.012059*Gln-0.17162*Trp-0.10994*Cit' | 0.952668 |
| 2 | '-0.62797+0.19297*Orn-0.013264*Gln-0.20242*Trp+0.06429*Phe-0.11838*Cit' | 0.955958 |
| 3 | '-4.9691+0.18505*Orn-0.15816*Trp-0.13554*Cit' | 0.947222 |
| 4 | '-0.33517+0.16031*Orn-0.013619*Gln-0.1532*Trp' | 0.947661 |
| 5 | '-6.6186+0.18762*Orn-0.18397*Trp+0.049261*Phe-0.14526*Cit' | 0.950329 |
| 6 | '-1.9858+0.16305*Orn-0.015063*Gln-0.18187*Trp+0.059923*Phe' | 0.949123 |
| 7 | '0.36783+0.19183*Orn-0.013353*Gln+0.056296*ABA-0.1766*Trp-0.10478*Cit' | 0.956689 |
| 8 | '-1.1852+0.19595*Orn-0.014602*Gln+0.057311*ABA-0.20832*Trp+0.06272*Phe-0.11707*Cit' | 0.961184 |
| 9 | '-1.0699+0.16241*Orn-0.014915*Gln+0.062106*ABA-0.15725*Trp' | 0.955994 |
| 10 | '0.91995+0.18679*Orn-0.011732*Gln-0.18972*Trp+0.021537*Ile-0.12007*Cit' | 0.954057 |
| 11 | '0.23231+0.18612*Orn-0.011924*Gln-0.18661*Trp+0.00042603*Ala-0.10421*Cit' | 0.954313 |
| 12 | '-2.6274+0.18271*Orn-0.1293*Trp-0.048276*His-0.12538*Cit' | 0.95117 |
| 13 | '0.89634+0.1869*Orn-0.011826*Gln-0.18279*Trp+0.0059253*Pro-0.11119*Cit' | 0.95318 |
| 14 | '-3.7855+0.18252*Orn-0.14982*Trp-0.061453*His+0.056233*Phe-0.13184*Cit' | 0.955044 |
| 15 | '-1.493+0.19054*Orn-0.013175*Gln-0.21731*Trp+0.064624*Phe+0.00040337*Ala-0.11307*Cit' | 0.957822 |
| 16 | '0.89634+0.19118*Orn-0.16427*Trp-0.020824*Ser-0.1299*Cit' | 0.944371 |
| 17 | '-5.1136+0.18227*Orn-0.17816*Trp-0.023633*Ile-0.14318*Cit' | 0.948867 |
| 18 | '0.36219+0.18932*Orn-0.011982*Gln-0.18118*Trp-0.033705*His+0.066331*Phe-0.11348*Cit' | 0.957785 |
| 19 | '-5.9217+0.18264*Orn-0.17654*Trp+0.0047172*Ala-0.12834*Cit' | 0.949635 |
| 20 | '-5.9845+0.18538*Orn+0.043463*ABA-0.16113*Trp-0.13253*Cit' | 0.950914 |
| 21 | '-0.19062+0.19081*Orn-0.013299*Gln-0.17869*Trp+0.068797*Phe-0.11296*Cit-0.027384*Tyr' | 0.9553 |
| 22 | '1.7522+0.19333*Orn-0.011294*Gln-0.17284*Trp-0.012728*Ser-0.10834*Cit' | 0.949232 |
| 23 | '-1.3495+0.15735*Orn-0.013364*Gln-0.1726*Trp+0.0054015*Ala' | 0.951937 |
| 24 | '1.7943+0.18848*Orn-0.011147*Gln-0.15513*Trp-0.025102*His-0.10605*Cit' | 0.953728 |
| 25 | '0.4897+0.18834*Orn-0.012915*Gln-0.18562*Trp+0.0082598*Lys-0.1059*Cit' | 0.953801 |

FIG.34

| No. | FORMULA | ROC_AUC |
|---|---|---|
| 26 | '1.4545+0.18899*Orn−0.011876*Gln−0.15661*Trp−0.10961*Cit−0.017089*Tyr' | 0.951645 |
| 27 | '−5.0907+0.18233*Orn−0.17198*Trp+0.007056*Pro−0.13684*Cit' | 0.948794 |
| 28 | '−0.86724+0.19074*Orn−0.013074*Gln−0.20998*Trp+0.0047195*Pro+0.063547*Phe−0.117752*Cit' | 0.956104 |
| 29 | '−2.5134+0.16558*Orn−0.016584*Gln+0.060756*ABA−0.1857*Trp+0.058068*Phe' | 0.958297 |
| 30 | '1.225+0.19064*Orn−0.011951*Gln−0.17005*Trp−0.10839*Cit−0.0032631*Thr' | 0.95212 |
| 31 | '−0.36892+0.19017*Orn−0.01166*Arg−0.012947*Gln−0.19466*Trp+0.066682*Phe−0.11034*Cit' | 0.955117 |
| 32 | '−0.19772+0.19494*Orn−0.012777*Gln−0.20238*Trp+0.063666*Phe−0.0080481*Ser−0.11703*Cit' | 0.954423 |
| 33 | '1.0345+0.1901*Orn−0.012069*Gln−0.17138*Trp+0.11101*Cit+0.00015684*Gly' | 0.952705 |
| 34 | '1.0626+0.1902*Orn−0.00014556*Arg−0.012054*Gln−0.1715*Trp−0.10981*Cit' | 0.952558 |
| 35 | '−0.343326+0.19346*Orn−0.013161*Gln−0.20004*Trp+0.064678*Phe−0.11563*Cit−0.0052077*Thr' | 0.955409 |
| 36 | '−0.70583+0.19208*Orn−0.013056*Gln−0.20755*Trp+0.0073091*Ile+0.062464*Phe−0.12114*Cit' | 0.956213 |
| 37 | '−0.86119+0.19266*Orn−0.013687*Gln−0.2088*Trp+0.062181*Phe+0.0041376*Lys−0.11671*Cit' | 0.956287 |
| 38 | '−0.86573+0.19176*Orn−0.013401*Gln−0.020062*Trp+0.06526*Phe−0.11933*Cit+0.0013163*Gly' | 0.956652 |
| 39 | '−4.246+0.18429*Orn−0.13708*Trp−0.13758*Cit−0.024293*Tyr' | 0.946491 |
| 40 | '0.98984+0.15932*Orn−0.012109*Gln−0.13075*Trp−0.039503*His' | 0.949963 |
| 41 | '−1.2405+0.16051*Orn−0.03049*Arg−0.0013622*Gln−0.16471*Trp+0.067398*Phe' | 0.947149 |
| 42 | '0.12526+0.15989*Orn+0.018679*Arg−0.012555*Gln−0.14057*Trp' | 0.94587 |
| 43 | '−7.9875+0.15146*Orn−0.13507*Trp' | 0.934942 |
| 44 | '−4.4549+0.18596*Orn−0.015547*Trp−0.13278*Cit−0.0068176*Thr' | 0.946199 |
| 45 | '−0.99356+0.15938*Orn−0.01276*Gln−0.014639*Trp−0.17302*Trp+0.010769*Lys' | 0.949379 |
| 46 | '−0.48082+0.15945*Orn−0.01276*Gln−0.015446*Trp−0.049126*His+0.061864*Phe' | 0.951279 |
| 47 | '−4.6936+0.18256*Orn−0.0075361*Arg−0.15446*Gln−0.15164*Trp−0.12759*Cit' | 0.946564 |
| 48 | '0.43929+0.16552*Orn−0.012749*Gln−0.15683*Trp−0.013978*Ser' | 0.944406 |
| 49 | '0.24932+0.16013*Orn−0.013521*Gln−0.13333*Trp−0.024046*Tyr' | 0.946564 |
| 50 | '−1.3822+0.16307*Orn−0.014825*Gln−0.14892*Trp+0.067847*Phe−0.042167*Tyr' | 0.947259 |

FIG.35

| No. | FORMULA | ROC_AUC |
|---|---|---|
| 51 | '-4.8349+0.18554*Orn-0.15933*Trp-0.13441*Cit-0.00067673*Gly' | 0.947149 |
| 52 | '-4.8603+0.18529*Orn-0.15687*Trp-0.0008343*Lys-0.13599*Cit' | 0.947295 |
| 53 | '-2.9948+0.16126*Orn-0.014872*Gln-0.20052*Trp+0.060281*Phe+0.0050703*Ala' | 0.952705 |
| 54 | '-7.453+0.18887*Orn+0.042169*ABA-0.18794*Trp+0.047698*Phe-0.14508*Cit' | 0.954167 |
| 55 | '-0.37129+0.15704*Orn-0.013625*Gln-0.16151*Trp+0.0047127*Pro' | 0.948611 |
| 56 | '-7.6305+0.18679*Orn-0.20215*Trp+0.050276*Phe+0.0044727*Ala-0.13929*Cit' | 0.953509 |
| 57 | '0.17765+0.16314*Orn-0.013336*Gln-0.15017*Trp-0.0088363*Thr' | 0.945614 |
| 58 | '-5.0825+0.19255*Orn-0.18796*Trp+0.048478*Phe-0.017686*Ser-0.13891*Cit' | 0.948099 |
| 59 | '-6.042+0.18556*Orn-0.15521*Trp+0.052492*Phe-0.14234*Cit-0.031047*Tyr' | 0.949963 |
| 60 | '-0.38908+0.15742*Orn-0.013602*Gln-0.15965*Trp+0.008778*Ile' | 0.947661 |
| 61 | '-4.3449+0.15182*Orn-0.10046*Trp-0.066762*His' | 0.943421 |
| 62 | '-6.8822+0.18567*Orn-0.19404*Trp+0.0061579*Pro+0.048721*Phe-0.14411*Cit' | 0.951352 |
| 63 | '-0.27187+0.16076*Orn-0.013583*Gln-0.15391*Trp-0.00036678*Gly' | 0.947478 |
| 64 | '1.3895+0.19631*Orn-0.012436*Gln+0.062974*Arg-0.17078*Trp+0.054062*Phe-0.12934*Cit' | 0.953655 |
| 65 | '-5.9752+0.18141*Orn-0.018686*ABA-0.17712*Trp+0.019513*Ser-0.10334*Cit' | 0.949306 |
| 66 | '-0.38566+0.18817*Orn-0.013147*Gln+0.05487*ABA-0.19057*Trp+0.0038119*Ala-0.098992*Cit' | 0.958626 |
| 67 | '-2.0205+0.16*Orn-0.014537*Gln+0.060819*ABA-0.17644*Trp+0.0049859*Ala' | 0.95731 |
| 68 | '-3.2689+0.17896*Orn-0.14656*Trp-0.058112*His+0.0058643*Ala-0.11539*Cit' | 0.954423 |
| 69 | '1.2408+0.19066*Orn-0.012472*Gln+0.060086*ABA-0.15646*Trp-0.030976*His-0.099731*Cit' | 0.959832 |
| 70 | '-6.7105+0.18631*Orn-0.019312*Trp+0.013396*Ile+0.046083*Phe-0.14697*Cit' | 0.950841 |
| 71 | '-5.9919+0.18849*Orn-0.18048*Trp+0.050167*Phe-0.14207*Cit-0.0086545*Thr' | 0.949708 |
| 72 | '-1.3264+0.16618*Orn-0.01469*Gln-0.17872*Trp+0.061009*Phe-0.01139*Thr' | 0.945833 |
| 73 | '0.28199+0.16224*Orn-0.013419*Gln+0.065505*ABA-0.13206*Trp+0.043164*His' | 0.960599 |
| 74 | '-3.8748+0.19309*Orn+0.054421*ABA-0.16795*Trp-0.026841*Ser-0.12659*Cit' | 0.949232 |
| 75 | '-5.9605+0.18866*Orn-0.01758*Trp+0.052691*Phe-0.0059375*Lys-0.14816*Cit' | 0.950329 |

FIG. 36

| No. | FORMULA | ROC AUC |
|---|---|---|
| 76 | '-3.6609+0.18366*Orn+0.049392*ABA-0.12934*Trp-0.052348*His-0.12181*Cit' | 0.956542 |
| 77 | '0.79603+0.18983*Orn-0.013171*Gln+0.057105*ABA-0.015863*Trp-0.10377*Cit-0.019469*Tyr' | 0.956287 |
| 78 | '0.38459+0.18947*Orn-0.012953*Gln+0.048911*ABA-0.018639*Trp+0.01325*Ile-0.11341*Cit' | 0.957675 |
| 79 | '0.20233+0.18929*Orn-0.012963*Gln+0.05165*ABA-0.18359*Trp+0.0042339*Pro-0.10554*Cit' | 0.956615 |
| 80 | '-4.5985+0.18065*Orn-0.16928*Trp-0.072122*His+0.058561*Phe+0.0060604*Ala-0.12245*Cit' | 0.958077 |
| 81 | '-2.5999+0.160032*Orn-0.014562*Gln-0.16002*Trp+0.0014562*Gln-0.16002*Trp+0.07434*Phe+0.0081323*Ala-0.066997*Tyr' | 0.954861 |
| 82 | '0.80244+0.19244*Orn-0.013289*Gln+0.060329*ABA-0.17175*Trp-0.10032*Cit-0.0084982*Thr' | 0.855811 |
| 83 | '-2.0758+0.16078*Orn-0.015055*Gln-0.18821*Trp+0.0039559*Pro+0.059722*Phe' | 0.950037 |
| 84 | '-1.4646+0.16666*Orn-0.014343*Gln-0.18327*Trp+0.058469*Phe-0.0097622*Ser' | 0.946857 |
| 85 | '-2.2936+0.16321*Orn-0.015806*Gln-0.19365*Trp+0.056832*Phe+0.0069721*Lys' | 0.951608 |
| 86 | '-6.6156+0.18764*Orn-0.18399*Trp+0.0049255*Phe-0.14524*Cit-1.3414e-005*Gly' | 0.950329 |
| 87 | '-2.3593+0.17972*Orn-0.14439*Trp+0.0085166*Pro-0.05413*His-0.1263*Cit' | 0.952961 |
| 88 | '-0.055318+0.16871*Orn-0.013838*Gln+0.067216*ABA-0.16055*Trp-0.019453*Ser' | 0.953034 |
| 89 | '-5.4895+0.15188*Orn-0.11904*Trp-0.082365*His+0.054054*Phe' | 0.94375 |
| 90 | '-4.7695+0.1851*Orn+0.0050084*ABA-0.15064*Trp-0.065714*His+0.054883*Phe-0.13124*Cit' | 0.961221 |
| 91 | '-2.6989+0.17927*Orn-0.14894*Trp-0.048845*His+0.023611*Ile-0.13275*Cit' | 0.951499 |
| 92 | '-0.24475+0.16568*Orn-0.014697*Gln+0.068022*ABA-0.15068*Trp-0.014227*Thr' | 0.953216 |
| 93 | '0.1744+0.19354*Orn+0.00060791*Arg-0.013552*Gln+0.058702*ABA-0.18192*Trp-0.10964*Cit' | 0.957493 |
| 94 | '0.12102+0.19088*Orn-0.013632*Gln+0.054013*ABA-0.18264*Trp+0.00037109*Lys-0.10348*Cit' | 0.957237 |
| 95 | '-1.9597+0.16436*Orn-0.015123*Gln-0.17905*Trp-0.0047964*Ile+0.061315*Phe' | 0.948904 |
| 96 | '-2.16+0.16198*Orn-0.015172*Gln-0.18042*Trp+0.060702*Phe+0.00088115*Gly' | 0.949525 |
| 97 | '-1.0311+0.18756*Orn-0.013545*Trp-0.045482*His-0.019204*Ser-0.12137*Cit' | 0.947588 |
| 98 | '0.38451+0.19199*Orn-0.013348*Gln+0.056297*ABA-0.17674*Trp-0.10468*Cit-0.00010079*Gly' | 0.956615 |
| 99 | '-6.2736+0.14951*Orn-0.029538*Arg-0.11428*Trp' | 0.936075 |
| 100 | '0.21752+0.15561*Orn-0.011558*Gln-0.14842*Trp-0.049448*His+0.0063779*Ala' | 0.955263 |

FIG.38

| CUTOFF VALUE | SENSITIVITY | SPECIFICITY | POSITIVE PREDICTIVE VALUE | NEGATIVE PREDICTIVE VALUE | CORRECT DIAGNOSTIC RATE |
|---|---|---|---|---|---|
| -700 | 1.000 | 0.000 | 0.036 | 1.000 | 0.036 |
| -300 | 1.000 | 0.242 | 0.047 | 1.000 | 0.269 |
| -200 | 0.969 | 0.484 | 0.066 | 0.998 | 0.502 |
| -100 | 0.938 | 0.683 | 0.100 | 0.997 | 0.692 |
| -50 | 0.938 | 0.780 | 0.138 | 0.997 | 0.786 |
| 0 | 0.938 | 0.854 | 0.194 | 0.997 | 0.857 |
| 5 | 0.938 | 0.861 | 0.201 | 0.997 | 0.864 |
| 10 | 0.938 | 0.863 | 0.204 | 0.997 | 0.866 |
| 15 | 0.938 | 0.867 | 0.208 | 0.997 | 0.869 |
| 20 | 0.938 | 0.875 | 0.219 | 0.997 | 0.877 |
| 30 | 0.938 | 0.884 | 0.233 | 0.997 | 0.886 |
| 40 | 0.906 | 0.894 | 0.242 | 0.996 | 0.894 |
| 50 | 0.875 | 0.910 | 0.267 | 0.995 | 0.909 |
| 100 | 0.813 | 0.942 | 0.342 | 0.993 | 0.937 |
| 150 | 0.719 | 0.973 | 0.500 | 0.989 | 0.964 |
| 200 | 0.688 | 0.988 | 0.688 | 0.988 | 0.977 |
| 300 | 0.563 | 0.994 | 0.783 | 0.984 | 0.979 |
| 500 | 0.281 | 0.999 | 0.900 | 0.974 | 0.973 |
| 1000 | 0.000 | 1.000 | 0.000 | 0.964 | 0.964 |

FIG.39

| No. | FORMULA | ROC AUC |
|---|---|---|
| 1 | '(15.2591 ± 1.1929)*Orn-(1 ± 0.37155)*Gln-(6.5808 ± 3.0593)*Trp+(7.3284 ± 3.3462)*Phe-(6.4922 ± 3.8802)*Cit-(6.7531 ± 2.7438)*Tyr' | 0.950877 |
| 2 | '(12.4921 ± 1.6021)*Orn-(1 ± 0.31942)*Gln-(5.64 ± 2.698)*Trp+(5.8469 ± 2.9314)*Phe-(5.5584 ± 2.4107)*Tyr' | 0.943677 |
| 3 | '(30.1815 ± 3.9243)*Orn-(2.483 ± 0.78132)*Gln-(14.9699 ± 6.6541)*Trp+(14.5444 ± 7.1689)*Phe+(1 ± 0.76895)*Ala-(16.31 ± 6.2433)*Tyr' | 0.950548 |
| 4 | '(12.3719 ± 1.6305)*Orn-(1 ± 0.322312)*Gln+(4.6747 ± 3.7886)*ABA-(5.4117 ± 2.7388)*Trp+(5.4402 ± 2.9898)*Phe-(5.9949 ± 2.4536)*Tyr' | 0.953253 |
| 5 | '(13.7415 ± 1.7735)*Orn-(1 ± 0.366635)*Gln-(5.59 ± 3.0428)*Trp+(3.2115 ± 2.8302)*His+(7.0663 ± 3.2843)*Phe-(5.7401 ± 2.694)*Tyr' | 0.94682 |
| 6 | '(14.1354 ± 1.8248)*Orn-(1.6887 ± 1.5436)*Arg-(1 ± 0.38587)*Gln-(6.0182 ± 3.0956)*Trp+(6.8651 ± 3.3426)*Phe-(5.8441 ± 2.7825)*Tyr' | 0.94375 |
| 7 | '(43.8087 ± 5.7207)*Orn-(3.7696 ± 1.1702)*Gln-(20.0836 ± 9.5898)*Trp+(21.7447 ± 10.4959)*Phe+(1 ± 1.3323)*Gly-(19.0245 ± 8.6262)*Tyr' | 0.943969 |
| 8 | '(23.8715 ± 3.1728)*Orn-(1.7894 ± 0.61454)*Gln-(9.9752 ± 5.1485)*Trp+(11.5309 ± 5.579)*Phe-(1 ± 1.728)*Lys-(9.8216 ± 4.6228)*Tyr' | 0.940387 |
| 9 | '(39.6602 ± 5.2752)*Orn-(3.2638 ± 1.0345)*Gln-(18.7554 ± 8.7731)*Trp+(1 ± 1.7622)*Pro+(18.5995 ± 9.4986)*Phe-(18.4479 ± 7.8409)*Tyr' | 0.944115 |
| 10 | '(18.1355 ± 2.3511)*Orn-(1 ± 0.46554)*Gln-(5.0473 ± 3.4743)*His+(8.6995 ± 4.1066)*Phe-(7.3103 ± 4.7377)*Cit-(9.8087 ± 3.1928)*Tyr' | 0.949561 |
| 11 | '(52.4639 ± 6.8629)*Orn-(4.308 ± 1.4048)*Gln-(23.6584 ± 11.4953)*Trp+(25.016 ± 12.4905)*Phe+(1 ± 5.1939)*Ser-(23.7081 ± 10.2515)*Tyr' | 0.943823 |
| 12 | '(95.9358 ± 12.5886)*Orn-(7.818 ± 2.5494)*Gln-(43.668 ± 20.8908)*Trp+(45.4409 ± 22.7477)*Phe-(43.5778 ± 19.1762)*Tyr+(1 ± 7.8173)*Thr' | 0.944006 |
| 13 | '(96.2345 ± 12.9404)*Orn-(7.7557 ± 2.4815)*Gln-(44.161 ± 21.6761)*Trp+(1 ± 14.2655)*Ile+(44.8718 ± 23.8785)*Phe-(43.3267 ± 18.9115)*Tyr' | 0.943713 |
| 14 | '(13.2271 ± 1.7169)*Orn-(1 ± 0.34021)*Gln+(5.8605 ± 3.9669)*ABA-(4.8948 ± 2.8803)*Trp-(4.3689 ± 2.3662)*Tyr' | 0.954605 |
| 15 | '(15.7382 ± 2.0447)*Orn-(1 ± 0.38983)*Gln+(6.1472 ± 4.4332)*ABA-(5.5509 ± 3.1892)*Trp-(5.3308 ± 4.0567)*Cit-(4.9911 ± 2.6392)*Tyr' | 0.956798 |
| 16 | '(15.7433 ± 2.0388)*Orn-(1 ± 0.39272)*Gln+(6.6126 ± 3.5069)*Phe-(6.5476 ± 4.1065)*ABA-(4.5764 ± 3.0585)*His+(6.4507 ± 3.6231)*Phe-(8.4772 ± 2.8047)*Tyr' | 0.94364 |
| 17 | '(14.5842 ± 1.9618)*Orn-(1 ± 0.40095)*Gln+(6.3499 ± 4.5488)*ABA-(4.5764 ± 3.0585)*His+(6.4507 ± 3.6231)*Phe-(8.4772 ± 2.8047)*Tyr' | 0.953289 |
| 18 | '(15.464 ± 2.0594)*Orn-(1 ± 0.39326)*Gln+(5.778 ± 4.5007)*ABA+(60.6529 ± 3.5414)*Phe-(61.321 ± 4.1265)*Cit-(9.6854 ± 2.7115)*Tyr' | 0.951754 |
| 19 | '(16.0797 ± 2.023)*Orn-(1 ± 0.38968)*Gln-(5.8515 ± 3.1796)*Trp-(5.7012 ± 4.0453)*Cit-(4.2984 ± 2.5929)*Tyr' | 0.949196 |
| 20 | '(28.2312 ± 3.7561)*Orn-(1.9161 ± 0.77047)*Gln-(10.508 ± 5.9992)*His+(13.9363 ± 6.9162)*Phe+(1 ± 0.74535)*Ala-(18.3468 ± 5.7405)*Tyr' | 0.949342 |
| 21 | '(14.6823 ± 1.9305)*Orn-(1 ± 0.39683)*Gln-(4.5631 ± 3.0278)*His+(6.9638 ± 3.5608)*Phe-(8.0199 ± 2.7659)*Tyr' | 0.942982 |
| 22 | '(32.9183 ± 4.3003)*Orn-(2.5389 ± 0.85189)*Gln-(14.2029 ± 9.9377)*ABA-(13.4193 ± 7.2226)*Trp+(1.435 ± 1.2283)*Lys-(7.9999 ± 4.6419)*Cit-(9.4752 ± 3.166)*Tyr' | 0.959722 |
| 23 | '(18.7107 ± 2.4417)*Orn-(1 ± 0.45378)*Gln+(8.4723 ± 4.0348)*Phe-(1.435 ± 1.2283)*Lys-(7.9999 ± 4.6419)*Cit-(9.4752 ± 3.166)*Tyr' | 0.941118 |
| 24 | '(13.3857 ± 1.6896)*Orn-(1 ± 0.33743)*Gln-(5.1371 ± 2.8303)*Trp-(3.6695 ± 2.306)*Tyr' | 0.945358 |
| 25 | '(36.1243 ± 4.5957)*Orn-(23.126 ± 0.88259)*Gln-(14.3955 ± 7.2647)*Trp+(1 ± 0.84896)*Ala-(12.384 ± 9.1779)*Cit-(12.352 ± 6.2724)*Tyr' | 0.95413 |

FIG.40

| No. | FORMULA | ROC AUC |
|---|---|---|
| 26 | '(12.7354 ± 1.7163)*Orn−(1 ± 0.33998)*Gln+(5.6009 ± 3.9796)*ABA+(4.7663 ± 3.1178)*Phe−(8.1927 ± 2.3934)*Tyr' | 0.947515 |
| 27 | '(20.0448 ± 4.0781)*Orn−(2.4449 ± 0.81335)*Gln−(13.5238 ± 6.8776)*Trp+(1 ± 0.80264)*Ala−(11.4719 ± 5.9368)*Tyr' | 0.950585 |
| 28 | '(17.0059 ± 2.2367)*Orn−(2.1855 ± 1.8963)*Arg−(1 ± 0.48051)*Gln−(4.7721 ± 3.5372)*His+(8.307 ± 4.1296)*Phe−(8.5938 ± 3.2643)*Tyr' | 0.942982 |
| 29 | '(15.1125 ± 1.9905)*Orn−(2.2315 ± 1.6735)*Arg−(1 ± 0.4193)*Gln+(6.5135 ± 3.6199)*Phe−(8.3651 ± 2.8521)*Tyr' | 0.937573 |
| 30 | '(12.8268 ± 1.6894)*Orn−(1 ± 0.33654)*Gln+(5.2234 ± 3.0651)*Phe−(7.7899 ± 2.3609)*Tyr' | 0.935673 |
| 31 | '(45.1033 ± 5.9101)*Orn−(2.9272 ± 1.1353)*Gln+(19.1042 ± 10.1327)*Phe+(1 ± 1.0826)*Ala−(18.3556 ± 11.882)*Cit−(30.1236 ± 8.455)*Tyr' | 0.947332 |
| 32 | '(14.7401 ± 1.9832)*Orn−(1.9606 ± 1.6699)*Arg−(1 ± 0.41531)*Gln+(5.8245 ± 4.6328)*ABA+(5.8816 ± 3.6155)*Phe−(8.7142 ± 2.8431)*Tyr' | 0.947588 |
| 33 | '(14.7199 ± 1.9839)*Orn−(1 ± 0.381186)*Gln−(6.8004 ± 4.3952)*ABA+(6.0084 ± 3.4798)*Phe−(1.2393 ± 1.0664)*Lys−(8.0669 ± 2.7409)*Tyr' | 0.946528 |
| 34 | '(38.9291 ± 5.0799)*Orn−(2.6846 ± 1.0009)*Gln+(17.4921 ± 8.7981)*Phe−(17.1342 ± 10.2559)*Cit+(1 ± 1.1234)*Gly−(22.6539 ± 6.757)*Tyr' | 0.943896 |
| 35 | '(14.3737 ± 1.8664)*Orn−(1 ± 0.38426)*Gln+(6.473 ± 4.3136)*ABA−(4.7501 ± 3.1831)*Trp−(2.4767 ± 2.9333)*His−(4.2783 ± 2.6331)*Tyr' | 0.958151 |
| 36 | '(14.7089 ± 1.9088)*Orn−(1.3454 ± 1.6159)*Arg−(1 ± 0.40177)*Gln+(6.1381 ± 4.4342)*ABA−(5.1149 ± 3.2049)*Trp−(4.3676 ± 2.6968)*Tyr' | 0.953692 |
| 37 | '(17.0315 ± 2.2604)*Orn−(1.5806 ± 1.8885)*Arg−(1 ± 0.446693)*Gln+(7.3688 ± 3.8515)*Phe−(5.8049 ± 4.8035)*Cit−(9.5984 ± 3.0779)*Tyr' | 0.94269 |
| 38 | '(29.2425 ± 3.7284)*Orn−(3.5402 ± 3.11749)*Arg−(1.9428 ± 0.7895)*Gln+(11.5537 ± 6.3301)*Trp+(1 ± 0.73744)*Ala−(9.53897 ± 5.495)*Tyr' | 0.94894 |
| 39 | '(13.4629 ± 1.7825)*Orn−(1 ± 0.35362)*Gln+(6.5737 ± 4.1195)*ABA−(6.5729 ± 2.1489)*Tyr' | 0.948501 |
| 40 | '(32.7017 ± 4.3542)*Orn−(5.3908 ± 3.6776)*Arg−(2.1673 ± 0.91512)*Gln+(14.357 ± 7.8995)*Phe+(1 ± 0.85229)*Ala−(21.1633 ± 6.6856)*Tyr' | 0.941813 |
| 41 | '(13.7974 ± 1.7839)*Orn−(1 ± 0.34823)*Gln+(7.5787 ± 2.522)*Trp−(4.8748 ± 3.664)*Cit' | 0.952778 |
| 42 | '(11.7357 ± 1.5188)*Orn−(1 ± 0.30762)*Gln−(6.7339 ± 2.2865)*Trp' | 0.947295 |
| 43 | '(15.1444 ± 1.9137)*Orn−(1.5886 ± 1.6241)*Arg−(1 ± 0.40598)*Gln−(5.4106 ± 3.2332)*Trp−(3.6289 ± 2.6676)*Tyr' | 0.943604 |
| 44 | '(14.6549 ± 1.9538)*Orn−(1 ± 0.393375)*Gln−(8.4779 ± 3.0343)*Trp−(4.1194 ± 2.9612)*His+(4.8392 ± 3.1904)*Phe−(5.5667 ± 3.9963)*Cit' | 0.957822 |
| 45 | '(16.0358 ± 2.11268)*Orn−(1 ± 0.40612)*Gln+(6.9605 ± 4.6124)*ABA−(5.3941 ± 4.2313)*Cit−(7.5015 ± 2.4028)*Tyr' | 0.951023 |
| 46 | '(27.8301 ± 3.545)*Orn−(1.9224 ± 0.73424)*Gln−(10.5541 ± 6.0917)*Trp−(5.9191 ± 5.6928)*His+(1 ± 0.7086)*Ala−(9.1631 ± 5.2205)*Tyr' | 0.955154 |
| 47 | '(13.9194 ± 1.7883)*Orn−(1.9523 ± 1.5269)*Arg−(1 ± 0.3886)*Gln−(7.0482 ± 2.7818)*Trp' | 0.945102 |
| 48 | '(52.0068 ± 6.8319)*Orn−(4.1658 ± 1.3854)*Gln+(24.0862 ± 15.7736)*ABA−(19.253 ± 11.3332)*Trp+(1 ± 1.58)*Gly−(16.3282 ± 9.502)*Tyr' | 0.955409 |
| 49 | '(15.7759 ± 2.10028)*Orn−(1 ± 0.391199)*Gln−(6.6226 ± 3.3383)*Trp+(1.6076 ± 2.101)*Ile−(5.9512 ± 4.0779)*Cit−(4.922 ± 2.7215)*Tyr' | 0.951389 |
| 50 | '(32.2367 ± 4.1742)*Orn−(2.0608 ± 0.799387)*Gln−(12.4731 ± 6.5134)*Trp+(1 ± 1.3194)*Pro−(11.9498 ± 8.2467)*Cit−(9.3426 ± 5.3346)*Tyr' | 0.951535 |

FIG.41

| No. | FORMULA | ROC AUC |
|---|---|---|
| 51 | (37.368 ± 5.0077)*Orn-(2.8992 ± 0.97667)*Gln+(16.4232 ± 11.3884)*ABA-(14.6035 ± 8.2537)*Trp+(1 ± 1.6673)*Pro-(13.0611 ± 6.8412)*Tyr | 0.955227 |
| 52 | (12.9483 ± 1.7422)*Orn-(2.1303 ± 1.475)*Arg-(1 ± 0.37327)*Gln-(7.9366 ± 2.8134)*Trp+(3.7948 ± 2.9461)*Phe | 0.946711 |
| 53 | (39.6033 ± 5.3842)*Orn-(3.1577 ± 1.0547)*Gln+(7.1612 ± 12.4662)*ABA+(15.0131 ± 9.7614)*Phe+(1 ± 1.0414)*Ala-(28.7228 ± 8.1329)*Tyr | 0.951389 |
| 54 | (12.8294 ± 1.7132)*Orn-(1 ± 0.33302)*Gln-(6.3602 ± 2.5702)*Trp-(3.3384 ± 2.723)*Phe-(5.0201 ± 3.4936)*Cit | 0.954459 |
| 55 | (17.2888 ± 2.1806)*Orn-(1 ± 0.43381)*Gln-(5.7704 ± 3.5074)*Trp-(2.3257 ± 3.2458)*His-(5.9486 ± 4.3677)*Cit-(4.1719 ± 2.8674)*Tyr | 0.951937 |
| 56 | (12.4021 ± 1.6698)*Orn-(1 ± 0.349903)*Gln+(7.3557 ± 2.7371)*Trp-(3.8331 ± 2.6773)*His+(4.0468 ± 2.8771)*Phe | 0.95223 |
| 57 | (15.1431 ± 1.9986)*Orn-(1 ± 0.41001)*Gln+(7.4457 ± 4.619)*ABA-(3.6515 ± 3.077)*His-(6.3433 ± 2.5651)*Tyr | 0.954276 |
| 58 | (1.41441 ± 1.9456)*Orn-(1.0886 ± 0.37055)*Gln+(6.1195 ± 4.3542)*ABA-(5.7996 ± 3.2605)*Trp-(1 ± 2.0528)*Ile-(5.0959 ± 2.6688)*Tyr | 0.954605 |
| 59 | (3.0804 ± 0.40063)*Orn-(1.0867 ± 0.656683)*Trp-(1 ± 0.59534)*His-(1.637 ± 0.71662)*Phe-(1.7163 ± 0.80443)*Cit-(1.4517 ± 0.584458)*Tyr | 0.950621 |
| 60 | (14.4752 ± 1.8272)*Orn-(1 ± 0.37908)*Gln-(5.0254 ± 3.13206)*Trp-(2.3197 ± 2.89942)*His-(3.5162 ± 2.5577)*Tyr | 0.948721 |
| 61 | (29.709 ± 3.9919)*Orn-(2.1125 ± 0.77321)*Gln-(13.5905 ± 8.85699)*ABA-(10.0813 ± 6.4733)*Trp-(1 ± 2.1655)*Lys-(6.904 ± 5.4333)*Tyr | 0.95402 |
| 62 | (0.85575 ± 5.127)*Orn-(3.0543 ± 1.0193)*Gln+(15.8737 ± 9.2811)*Phe+(1 ± 0.99688)*Ala-(26.6835 ± 7.7714)*Tyr | 0.939693 |
| 63 | (59.0579 ± 7.4689)*Orn-(3.8773 ± 1.4689)*Gln-(21.488 ± 11.7237)*Trp-(21.7151 ± 14.9575)*Cit+(1 ± 1.6373)*Gly-(14.7901 ± 9.7164)*Tyr | 0.950475 |
| 64 | (14.4864 ± 1.9437)*Orn-(2.1148 ± 1.6594)*Arg-(1 ± 0.427)*Gln-(7.9996 ± 3.2263)*Trp-(3.9604 ± 3.1424)*His+(5.1645 ± 3.3667)*Phe | 0.949854 |
| 65 | (15.5417 ± 2.0903)*Orn-(1 ± 0.39153)*Gln-(6.4209 ± 3.0274)*Trp-(6.0146 ± 3.2305)*Phe-(1.3272 ± 1.0534)*Lys-(6.3452 ± 3.9955)*Cit | 0.949306 |
| 66 | (17.5816 ± 2.322)*Orn-(1.11 ± 0.432888)*Gln-(1 ± 2.3465)*Ile-(7.8381 ± 4.078)*Phe-(7.1574 ± 4.5221)*Cit-(9.9911 ± 3.0603)*Tyr | 0.943713 |
| 67 | (57.1008 ± 7.5702)*Orn-(3.6792 ± 1.4385)*Gln+(1 ± 2.8834)*Pro+(23.8399 ± 12.8695)*Phe-(24.2455 ± 15.0495)*Cit-(34.9563 ± 10.0063)*Tyr | 0.944627 |
| 68 | (20.4095 ± 2.7651)*Orn-(1.289 ± 0.54179)*Gln-(5.5544 ± 4.1176)*His+(9.9327 ± 4.8673)*Phe-(1 ± 1.5069)*Lys-(10.1501 ± 3.8553)*Tyr | 0.938487 |
| 69 | (14.4889 ± 1.9327)*Orn-(1.0035 ± 0.37216)*Gln+(6.323 ± 3.3821)*Phe-(1 ± 1.0324)*Lys-(7.6462 ± 2.8726)*Tyr | 0.931579 |
| 70 | (37.2768 ± 5.10599)*Orn-(3.1728 ± 1.03666)*Gln+(17.3032 ± 11.8061)*ABA+(14.9949 ± 9.284)*Phe+(1 ± 1.11857)*Gly-(23.5658 ± 7.1304)*Tyr | 0.947661 |
| 71 | (11.4073 ± 1.5344)*Orn-(1 ± 0.30619)*Gln+(4.068 ± 3.5556)*ABA-(6.7769 ± 2.2764)*Trp | 0.957966 |
| 72 | (30.8071 ± 4.0601)*Orn-(2.0463 ± 0.80463)*Gln+(13.3006 ± 6.9555)*Phe+(1 ± 2.8846)*Ser-(12.7903 ± 8.0973)*Cit-(18.5376 ± 5.3241)*Tyr | 0.943677 |
| 73 | (13.2618 ± 1.7002)*Orn-(1 ± 0.36113)*Gln-(6.4987 ± 2.728)*Trp-(3.0558 ± 2.7012)*His | 0.95011 |
| 74 | (18.0079 ± 2.314)*Orn-(1 ± 1.9492)*Arg-(1.0665 ± 0.4583)*Gln-(6.347 ± 3.6346)*Trp-(5.5556 ± 4.8946)*Cit-(4.5007 ± 3.0156)*Tyr | 0.949013 |
| 75 | (41.6159 ± 5.4587)*Orn-(2.7264 ± 1.0668)*Gln+(17.7962 ± 9.34493)*Phe-(17.8083 ± 10.9953)*Cit-(25.4907 ± 7.4023)*Tyr+(1 ± 3.244)*Thr | 0.944079 |

FIG.42

| No. | FORMULA | ROC_AUC |
|---|---|---|
| 76 | '(45.2969 ± 5.9028)*Orn-(3.3408 ± 1.2044)*Gln+(20.4173 ± 13.6724)*ABA-(16.9412 ± 9.823)*Trp-(1 ± 4.4865)*Ser-(14.8774 ± 8.0782)*Tyr' | 0.954423 |
| 77 | '(63.0876 ± 8.2539)*Orn-(4.6731 ± 1.6672)*Gln+(28.3164 ± 19.013)*ABA-(23.237 ± 13.5979)*Trp-(20.3177 ± 11.477)*Tyr-(1 ± 5.15561)*Thr' | 0.954386 |
| 78 | '(36.6935 ± 4.4063)*Orn-(2.5914 ± 0.86472)*Gln-(13.7018 ± 7.2881)*Trp+(1 ± 1.4744)*Pro-(9.9719 ± 5.9623)*Tyr' | 0.946674 |
| 79 | '(55.4874 ± 7.3811)*Orn-(4.0432 ± 1.5649)*Gln-(16.6325 ± 11.5949)*His+(27.2973 ± 13.6215)*Phe+(1 ± 1.7318)*Gly-(29.9405 ± 10.5766)*Tyr' | 0.942507 |
| 80 | '(13.0621 ± 1.767)*Orn-(1 ± 0.33772)*Gln-(5.7048 ± 2.956)*Trp+(1.2335 ± 1.857)*Ile-(4.1269 ± 2.4066)*Tyr' | 0.944737 |
| 81 | '(39.0325 ± 5.3096)*Orn-(2.7021 ± 1.0705)*Gln+(1 ± 1.7808)*Pro-(12.9479 ± 8.2463)*His+(18.5302 ± 9.617)*Phe-(22.1452 ± 7.5159)*Tyr' | 0.944846 |
| 82 | '(10.899 ± 1.4731)*Orn-(1 ± 0.295595)*Gln-(7.3487 ± 2.3336)*Trp+(2.7136 ± 2.4684)*Phe' | 0.948173 |
| 83 | '(15.5437 ± 1.9999)*Orn-(1 ± 0.40693)*Gln-(7.3982 ± 3.0125)*His-(3.1821 ± 2.9823)*Trp-(5.2465 ± 4.112)*Cit' | 0.954898 |
| 84 | '(17.9685 ± 2.3842)*Orn-(1 ± 0.46845)*Gln+(7.9023 ± 5.1706)*ABA-(3.8394 ± 3.4423)*His-(5.742 ± 4.7514)*Cit-(7.3199 ± 2.8701)*Tyr' | 0.956213 |
| 85 | '(31.3984 ± 4.1833)*Orn-(2.0632 ± 0.8569)*Gln+(15.2304 ± 9.6537)*ABA-(9.2101 ± 6.5568)*His-(1 ± 0.82865)*Ala-(15.8479 ± 5.7638)*Tyr' | 0.961001 |
| 86 | '(16.4436 ± 2.111)*Orn-(1 ± 0.40703)*Gln-(5.8205 ± 4.2307)*Cit-(6.8664 ± 2.3726)*Tyr' | 0.94386 |
| 87 | '(13.3249 ± 1.7967)*Orn-(1 ± 0.344466)*Gln+(4.0947 ± 3.907)*ABA-(7.5638 ± 2.4958)*Trp-(4.5393 ± 3.6361)*Cit' | 0.959503 |
| 88 | '(45.3325 ± 5.989)*Orn-(2.6817 ± 1.1193)*Gln-(15.5924 ± 9.0478)*Trp-(1 ± 3.0128)*Lys-(16.1607 ± 11.2796)*Cit-(11.1533 ± 7.5758)*Tyr' | 0.948684 |
| 89 | '(28.8087 ± 3.8649)*Orn-(2.442 ± 0.7671)*Gln+(1.8.6475 ± 5.7976)*Trp+(8.9444 ± 6.2564)*Phe-(12.2642 ± 7.9154)*Cit+(1 ± 0.86444)*Gly' | 0.955482 |
| 90 | '(15.4333 ± 2.039)*Orn-(1.7762 ± 1.7176)*Arg-(1 ± 0.4284)*Gln+(6.9826 ± 4.7421)*ABA-(6.702 ± 2.5587)*Tyr' | 0.94788 |
| 91 | '(26.6737 ± 3.6015)*Orn-(1.8978 ± 0.74228)*Gln-(8.8999 ± 5.6859)*His+(13.0838 ± 6.5737)*Phe-(15.1863 ± 5.1978)*Tyr+(1 ± 2.2875)*Thr' | 0.942982 |
| 92 | '(39.123 ± 5.2277)*Orn-(6.0475 ± 4.3819)*Arg-(2.8117 ± 1.1217)*Gln+(18.0175 ± 9.5368)*Phe+(1 ± 1.2208)*Gly-(21.0682 ± 7.5216)*Tyr' | 0.937025 |
| 93 | '(18.2233 ± 2.46607)*Orn-(1.2342 ± 0.4864)*Gln-(5.5012 ± 3.7109)*His-(1 ± 2.6257)*Ile+(9.0664 ± 4.5882)*Phe-(9.5083 ± 3.4761)*Tyr' | 0.943165 |
| 94 | '(12.984 ± 1.7336)*Orn-(1 ± 0.36254)*Gln+(4.9329 ± 4.0243)*ABA-(6.5323 ± 2.7372)*Trp-(3.2971 ± 2.7163)*His' | 0.962135 |
| 95 | '(13.4233 ± 1.7908)*Orn-(5.3443 ± 2.10311)*Gln-(30.8695 ± 16.782)*Trp-(30.4597 ± 21.4909)*Cit-(23.1804 ± 14.0582)*Tyr+(1 ± 6.369)*Trp' | 0.953911 |
| 96 | '(84.6284 ± 10.7513)*Orn-(5.3443 ± 2.10311)*Gln-(30.8695 ± 16.782)*Trp-(25.9356 ± 14.3451)*Trp+(1 ± 1.9978)*Gly-(17.5156 ± 11.8847)*Tyr' | 0.950037 |
| 97 | '(67.4763 ± 8.5929)*Orn-(5.2727 ± 1.7584)*Gln-(25.9356 ± 14.3451)*Trp+(1 ± 1.9978)*Gly-(17.5156 ± 11.8847)*Tyr' | 0.94598 |
| 98 | '(120.8787 ± 15.3553)*Orn-(7.4311 ± 3.0343)*Gln-(44.1778 ± 24.0477)*Trp-(1 ± 10.9083)*Ser-(42.9347 ± 30.4189)*Cit-(32.1859 ± 19.4853)*Tyr' | 0.949159 |
| 99 | '(13.6551 ± 1.758)*Orn-(1 ± 0.35132)*Gln-(5.9068 ± 2.10025)*Tyr' | 0.938999 |
| 100 | '(35.4564 ± 4.7346)*Orn-(2.5074 ± 1.0053)*Gln-(10.9006 ± 7.3799)*His+(17.1528 ± 8.693)*Phe+(1 ± 3.585)*Ser-(19.5916 ± 6.7313)*Tyr' | 0.94375 |

FIG.43

| ROC_AUC | 0.7 | | 0.75 | | 0.8 | | 0.85 | |
|---|---|---|---|---|---|---|---|---|
| RANK | AMINO ACID | FREQUENCY | AMINO ACID | FREQUENCY | AMINO ACID | FREQUENCY | AMINO ACID | FREQUENCY |
| 1 | Cys | 1794 | Orn | 1794 | Orn | 1794 | Orn | 1794 |
| 2 | Orn | 1794 | Cys | 1699 | Cys | 728 | Ile | 265 |
| 3 | Arg | 1591 | Arg | 1063 | Ile | 495 | Leu | 262 |
| 4 | Trp | 1499 | Tau | 932 | Arg | 480 | Cys | 257 |
| 5 | Tau | 1432 | Ile | 921 | Trp | 406 | Arg | 245 |
| 6 | His | 1423 | Trp | 918 | Leu | 399 | Trp | 239 |
| 7 | Glu | 1384 | Glu | 820 | Tau | 387 | Phe | 236 |
| 8 | Ile | 1283 | His | 815 | Phe | 355 | Glu | 235 |
| 9 | Gln | 1240 | Phe | 757 | Tyr | 354 | Val | 235 |
| 10 | ABA | 1219 | Pro | 740 | ABA | 352 | Lys | 235 |
| 11 | Pro | 1195 | ABA | 729 | Gln | 328 | Tau | 234 |
| 12 | Phe | 1170 | Leu | 719 | His | 319 | Pro | 234 |
| 13 | Lys | 1126 | Lys | 712 | Glu | 317 | Gly | 234 |
| 14 | Leu | 1088 | Cit | 644 | Lys | 317 | Ala | 234 |
| 15 | Ala | 1086 | Ala | 642 | Gly | 314 | ABA | 234 |
| 16 | Cit | 1070 | Gln | 618 | Pro | 307 | Thr | 233 |
| 17 | Tyr | 1049 | Gly | 598 | Val | 298 | Ser | 233 |
| 18 | Val | 1024 | Val | 596 | Ala | 291 | Asn | 233 |
| 19 | Gly | 1003 | Tyr | 596 | Cit | 289 | Gln | 233 |
| 20 | Ser | 961 | Met | 574 | Ser | 287 | Cit | 233 |
| 21 | Met | 946 | Ser | 563 | Met | 284 | Met | 233 |
| 22 | Thr | 908 | Thr | 546 | Thr | 267 | Tyr | 233 |
| 23 | Asn | 810 | Asn | 447 | Asn | 252 | His | 233 |

FIG.45

| SUBJECT TO BE DISCRIMINATED | ROC_AUC |
|---|---|
| Thr | 0.6078 |
| Ser | 0.5293 |
| Asn | 0.5874 |
| Glu | 0.655 |
| Gln | 0.5591 |
| Pro | 0.5416 |
| Gly | 0.5052 |
| Ala | 0.5227 |
| Cit | 0.6536 |
| a-ABA | 0.5794 |
| Val | 0.716 |
| Met | 0.6498 |
| Ile | 0.716 |
| Leu | 0.699 |
| Tyr | 0.7075 |
| Phe | 0.7131 |
| His | 0.6578 |
| Trp | 0.5988 |
| Orn | 0.5529 |
| Lys | 0.5345 |
| Arg | 0.4915 |

FIG.47

| No. | Formula | AUC |
|---|---|---|
| 1 | 'Gln/Val-0.83239*Cit/a-ABA-0.15094*Thr/Glu' | 0.9371 |
| 2 | 'Gln/Val-0.84403*Cit/a-ABA-1.7266*Thr/Pro' | 0.9291 |
| 3 | 'Gln/Val-0.19917*Thr/a-ABA+1.6145*Glu/His' | 0.9253 |
| 4 | 'Ile-157.0114*a-ABA/His+246.1437*Asn/Ala' | 0.9197 |
| 5 | 'Gln/Val+7.0423*a-ABA/Thr-0.28176*His/Glu' | 0.9187 |
| 6 | 'Glu/Val+0.0081499*Gln/Cit+0.9244*a-ABA/Leu' | 0.9178 |
| 7 | 'Glu/Val+0.85831*a-ABA/Ile+0.028453*Gln/Phe' | 0.9145 |
| 8 | 'Ile-152.5139*a-ABA/His-53.0322*Glu/Thr' | 0.9145 |
| 9 | 'Gln/Val+0.5334*Glu/Cit+2.9232*a-ABA/His' | 0.9107 |
| 10 | 'Glu/Val+0.0069227*Gln/Cit-0.02584*Ile/a-ABA' | 0.9102 |
| 11 | 'a-ABA/Ile-2.6816*Phe/Gln+0.025351*Ala/His' | 0.9102 |
| 12 | 'a-ABA/Ile-2.6816*Phe/Gln+0.025351*Ala/His' | 0.9102 |
| 13 | 'Glu/Val-0.034058*Ile/a-ABA-1.0655*Thr/Gln' | 0.9093 |
| 14 | 'a-ABA/Ile+1.2995*Glu/Val-1.1752*Thr/Gln' | 0.9083 |
| 15 | 'Glu/Val+0.95192*a-ABA/Ile+0.033478*Gln/His' | 0.9083 |
| 16 | 'Gln/Phe-2.792*Cit/a-ABA+20.6672*Glu/Val' | 0.9078 |
| 17 | 'a-ABA/Ile+1.1051*Glu/Val-1.0332*Thr/Gln' | 0.9078 |
| 18 | 'Gln/Phe+24.6115*a-ABA/Thr+20.9578*Glu/Val' | 0.9074 |
| 19 | 'a-ABA/Met+0.31539*Gln/Val-1.5266*Thr/Ala' | 0.9074 |
| 20 | 'a-ABA/Ile-3.5266*Phe/Gln+0.048008*Ala/Thr' | 0.9064 |
| 21 | 'a-ABA/Ile+1.0076*Glu/Val+0.027569*Gln/His' | 0.906 |
| 22 | 'Glu/Val+0.81675*a-ABA/Ile+0.035983*Gln/Thr' | 0.9055 |
| 23 | 'Glu/Val-0.048516*Ile/a-ABA-0.88698*His/Ala' | 0.9055 |
| 24 | 'a-ABA/Ile-0.38186*Thr/Pro-0.003581*His' | 0.9055 |
| 25 | 'Gln/Phe-0.57353*Thr/a-ABA+16.3388*Glu/Val' | 0.9045 |
| 26 | 'a-ABA/Ile+1.0326*Glu/Val-1.2343*Thr/Gln' | 0.9045 |
| 27 | 'a-ABA/Ile-0.77513*Thr/Ala-0.0031592*His' | 0.9041 |
| 28 | 'Glu/Val-0.035377*Ile/a-ABA-1.1543*Thr/Gln' | 0.9031 |
| 29 | 'Glu/Val+0.73348*a-ABA/Ile-0.94952*Thr/Gln' | 0.9026 |
| 30 | 'a-ABA/Ile+1.2622*Glu/Val-0.63004*Phe/Lys' | 0.9026 |
| 31 | 'Glu/Val+0.018874*Gly/Cit-0.014378*Thr/a-ABA' | 0.9022 |
| 32 | 'Gln/Phe-0.83169*Thr/a-ABA+18.278*Glu/Val' | 0.9022 |
| 33 | 'Glu/Val+0.57405*a-ABA/Ile+0.0070616*Gln/Cit' | 0.9017 |
| 34 | 'Glu/Val+0.77928*a-ABA/Ile-2.5128*Phe/Gln' | 0.9008 |
| 35 | 'a-ABA/Ile+1.0423*Glu/Val-0.13757*Leu/Trp' | 0.9008 |
| 36 | 'Gln/Val-0.20153*Thr/a-ABA+1.8112*Glu/Ile' | 0.9003 |
| 37 | 'Glu/Val+0.67613*a-ABA/Ile+0.02255*Gln/His' | 0.8998 |
| 38 | 'Gln/Phe-0.82599*Thr/a-ABA+21.8772*Glu/Val' | 0.8998 |
| 39 | 'Glu/Val+0.83349*a-ABA/Ile-1.2462*Thr/Gln' | 0.8998 |
| 40 | 'Glu/Val+0.91103*a-ABA/Ile+0.03108*Gln/His' | 0.8993 |
| 41 | 'Glu/Val+0.0095696*Gln/Cit-0.0017643*Leu' | 0.8989 |
| 42 | 'Thr/a-ABA-0.84275*Gln/Phe-19.1543*Glu/Val' | 0.8989 |
| 43 | 'Ile-120.8313*a-ABA/His+26.5672*Cit/Glu' | 0.8984 |
| 44 | 'Gln/Val+2.1842*a-ABA/Met-1.8674*Thr/Pro' | 0.8984 |
| 45 | 'Glu/Val+0.044554*Arg/Cit-0.017773*Thr/a-ABA' | 0.8979 |
| 46 | 'Ile-288.8196*a-ABA/Thr-8.1978*Gln/Phe' | 0.8979 |
| 47 | 'a-ABA/Ile+0.03537*Gln/Phe-0.33579*Thr/Pro' | 0.8979 |
| 48 | 'Glu/Val-5.3511*Cit/Gln+0.97224*a-ABA/Leu' | 0.8974 |
| 49 | 'a-ABA/Met+0.35509*Gln/Val-0.054974*Thr/Glu' | 0.8974 |
| 50 | 'Gln/Phe+26.933*a-ABA/Ile+9.0698*Glu/His' | 0.8974 |

FIG.48

| No. | Formula | AUC |
|---|---|---|
| 51 | 'Glu/Val+0.70554*a-ABA/Ile-0.3657*His/Lys' | 0.897 |
| 52 | 'Glu/Val+0.4824*a-ABA/Ile-1.4541*Cit/Gly' | 0.897 |
| 53 | 'Gln/Phe-0.57077*Thr/a-ABA+0.85846*Ala/Val' | 0.897 |
| 54 | 'Glu/Val+0.48474*a-ABA/Ile+0.0067768*Gln/Cit' | 0.897 |
| 55 | 'Glu/Val+0.7478*a-ABA/Ile+0.027093*Gln/His' | 0.897 |
| 56 | 'a-ABA/Ile+0.027672*Gln/Phe+0.25574*Glu/His' | 0.897 |
| 57 | 'Glu/Val-6.1552*Cit/Gln+1.1057*a-ABA/Leu' | 0.897 |
| 58 | 'Gln/Phe-0.57077*Thr/a-ABA+0.85846*Ala/Val' | 0.897 |
| 59 | 'Glu/Val-0.027161*Ile/a-ABA-3.2475*Cit/Gln' | 0.8965 |
| 60 | 'Gln/Phe-0.50649*Thr/a-ABA+18.7821*Glu/Val' | 0.8965 |
| 61 | 'Gln/Phe-2.1914*Cit/a-ABA-11.9907*Thr/Ala' | 0.896 |
| 62 | 'Ile+4.556*Thr/a-ABA+1.8151*Val/Glu' | 0.8956 |
| 63 | 'Glu/Val+0.80334*a-ABA/Ile-0.0028056*His' | 0.8956 |
| 64 | 'Glu/Val+0.72327*a-ABA/Ile-1.088*Thr/Gln' | 0.8956 |
| 65 | 'Glu/Val+0.78675*a-ABA/Ile-1.0683*Thr/Gln' | 0.8956 |
| 66 | 'a-ABA/Leu-0.38268*Thr/Ala+0.026259*Lys/Met' | 0.8956 |
| 67 | 'Glu/Val+0.73835*a-ABA/Ile-1.8092*His/Gln' | 0.8951 |
| 68 | 'Glu/Val+0.0079658*Gln/Cit+0.40698*a-ABA/His' | 0.8946 |
| 69 | 'Glu/Val-0.054814*Ile/a-ABA-1.2394*Thr/Gln' | 0.8946 |
| 70 | 'Glu/Val-0.023053*Ile/a-ABA-3.2591*Cit/Gln' | 0.8941 |
| 71 | 'Glu/Val+0.77968*a-ABA/Ile-1.9486*His/Gln' | 0.8941 |
| 72 | 'Glu/Val+0.53222*a-ABA/Ile-0.395*Phe/Lys' | 0.8941 |
| 73 | 'Glu/Val+0.049737*Gln/Thr-0.02939*Leu/a-ABA' | 0.8937 |
| 74 | 'Glu/Val+0.0064426*Gln/Cit+0.77539*a-ABA/Leu' | 0.8937 |
| 75 | 'Glu/Val+0.84182*a-ABA/Ile-2.0881*His/Gln' | 0.8937 |
| 76 | 'Gln/Phe+20.0191*a-ABA/Thr-12.7801*His/Ala' | 0.8937 |
| 77 | 'Glu/Val+0.024996*Gln/Ile-0.07259*Cit/a-ABA' | 0.8932 |
| 78 | 'Gln/Phe+4.7476*a-ABA/Cit-0.37318*Val/Glu' | 0.8927 |
| 79 | 'Glu/Val+0.042956*Gln/Phe-0.029195*Thr/a-ABA' | 0.8922 |
| 80 | 'Glu/Val-0.038335*Ile/a-ABA-1.9595*His/Gln' | 0.8922 |
| 81 | 'Glu/Val+0.0077703*Gln/Cit-0.018461*Leu/a-ABA' | 0.8922 |
| 82 | 'Glu/Val+0.76093*a-ABA/Ile+0.022302*Gln/His' | 0.8918 |
| 83 | 'Glu/Val+0.71202*a-ABA/Ile+0.022707*Gln/His' | 0.8918 |
| 84 | 'Glu/Val+0.0078226*Gln/Cit+0.76085*a-ABA/Leu' | 0.8918 |
| 85 | 'a-ABA/Ile+1.266*Glu/Val+0.030079*Gln/Phe' | 0.8913 |
| 86 | 'Gln/Phe-0.45641*Thr/a-ABA+0.10847*Ala/Cit' | 0.8913 |
| 87 | 'Ile-147.9682*a-ABA/His+104.1199*Thr/Ala' | 0.8913 |
| 88 | 'Glu/Val+0.58838*a-ABA/Ile-0.83597*Thr/Gln' | 0.8908 |
| 89 | 'Glu/Val+0.079841*Lys/Ile+0.51008*a-ABA/His' | 0.8908 |
| 90 | 'Glu/Val+0.60719*a-ABA/Ile+0.034945*Gly/Thr' | 0.8908 |
| 91 | 'Glu/Val+0.81461*a-ABA/Ile+0.022798*Gln/His' | 0.8904 |
| 92 | 'Glu/Val+0.62979*a-ABA/Ile+0.021442*Gln/Phe' | 0.8904 |
| 93 | 'Glu/Val+0.0098792*Gln/Cit-0.32088*Thr/Gly' | 0.8899 |
| 94 | 'Glu/Val+0.0074098*Gln/Cit+0.83166*a-ABA/Leu' | 0.8899 |
| 95 | 'Glu/Val+0.61701*a-ABA/Ile+0.02329*Gln/Phe' | 0.8899 |
| 96 | 'Thr/Ala-0.92069*a-ABA/Ile-0.037588*Gln/Phe' | 0.8899 |
| 97 | 'Ile+4.7995*Thr/a-ABA-11.7838*Pro/His' | 0.8889 |
| 98 | 'Ile+4.7995*Thr/a-ABA-11.7838*Pro/His' | 0.8889 |
| 99 | 'Gln/Phe+25.1236*a-ABA/Ile+6.8327*Glu/His' | 0.8885 |
| 100 | 'Glu/Val-6.2781*Cit/Gln+1.0415*a-ABA/Leu' | 0.8885 |

FIG.50

| No. | Formula | ROC_AUC |
|---|---|---|
| 1 | '−0.89776−0.041732*Val+0.09588*Glu−0.038785*Thr+0.17714*a−ABA+0.0093693*Gln+0.018113*Pro' | 0.8993 |
| 2 | '3.3839−0.037697*Val−0.072233*Phe+0.092641*Glu−0.176*Cit+0.16635*a−ABA+0.013821*Gln' | 0.9012 |
| 3 | '3.6936−0.031125*Val−0.10127*Phe−0.06289*His+0.097103*Glu+0.2087*a−ABA+0.013807*Gln' | 0.9017 |
| 4 | '2.5905−0.045479*Val+0.09416*Glu−0.20792*Cit+0.13895*a−ABA+0.012237*Gln' | 0.8951 |
| 5 | '−0.49791−0.032824*Val−0.091801*Phe+0.092786*Glu+0.18525*a−ABA+0.010048*Gln+0.012174*Pro' | 0.896 |
| 6 | '−0.19628−0.032447*Val−0.11143*Phe+0.024565*Tyr+0.0938*Glu+0.19212*a−ABA+0.011239*Gln' | 0.9031 |
| 7 | '3.6405−0.044612*Val+0.090636*Glu−0.20411*Cit−0.054531*Met+0.15012*a−ABA+0.012472*Gln' | 0.8956 |
| 8 | '1.1448−0.031798*Val−0.069974*Phe+0.093244*Glu+0.18447*a−ABA+0.011963*Gln−0.023791*Orn' | 0.8918 |
| 9 | '4.9347−0.029098*Phe−0.061342*Phe+0.079386*Glu−0.025931*Thr+0.16924*a−ABA+0.018583*Pro' | 0.8899 |
| 10 | '2.8797−0.034451*Val−0.026361*Leu+0.095466*Glu−0.21035*Cit+0.15446*a−ABA+0.012144*Gln' | 0.896 |
| 11 | '1.8465−0.032189*Val−0.083176*Phe+0.081918*Glu−0.025399*Asn+0.18632*a−ABA+0.010503*Gln' | 0.8894 |
| 12 | '0.40415−0.030647*Val−0.091495*Phe+0.088538*Glu+0.015429*Met+0.17862*a−ABA+0.010461*Gln' | 0.8885 |
| 13 | '0.68372−0.032635*Val−0.091085*Phe+0.0050907*Leu+0.087069*Glu+0.17849*a−ABA+0.010561*Gln' | 0.888 |
| 14 | '3.2947−0.054633*Phe−0.048265*Leu+0.073641*Glu−0.025895*Thr+0.18601*a−ABA+0.016903*Pro' | 0.8776 |
| 15 | '2.2659−0.065666*Phe−0.056873*Leu+0.078836*Glu−0.16169*Cit+0.17689*a−ABA+0.010891*Gln' | 0.8871 |
| 16 | '3.7675−0.082255*Ile−0.091301*Phe−0.079471*His+0.074913*Glu+0.22692*a−ABA+0.012135*Gln' | 0.8951 |
| 17 | '0.65954−0.075438*Phe−0.04619*Leu+0.07561*Glu−0.022608*Thr+0.20232*a−ABA+0.0096072*Gln' | 0.8852 |
| 18 | '3.5678−0.028445*Val−0.068987*Phe+0.080445*Glu+0.15624*a−ABA+0.013611*Pro' | 0.8833 |
| 19 | '−0.33738−0.037747*Val−0.052853*His+0.094816*Glu+0.15842*a−ABA+0.0091393*Gln+0.012128*Pro' | 0.8809 |
| 20 | '0.2312−0.039852*Val+0.094262*Glu−0.022092*Thr+0.16294*a−ABA+0.010345*Gln−0.014616*Orn' | 0.8866 |
| 21 | '0.10811−0.039917*Val+0.0028622*Tyr+0.092043*Glu−0.02614*Thr+0.1646*a−ABA+0.0096644*Gln' | 0.8852 |
| 22 | '0.91751−0.041557*Ile−0.030797*Val+0.089026*Glu−0.026951*Thr+0.16505*a−ABA+0.0094624*Gln' | 0.8842 |
| 23 | '1.792−0.063705*Leu+0.07799*Glu−0.028568*Thr+0.17595*a−ABA+0.017237*Pro' | 0.8715 |
| 24 | '−1.4156−0.081586*Phe−0.046644*Leu+0.079664*Glu+0.18442*a−ABA+0.0077304*Gln+0.0098243*Pro' | 0.8833 |
| 25 | '5.7569−0.027683*Val−0.076951*Phe+0.022761*Tyr+0.079131*Glu−0.016229*Thr+0.16727*a−ABA' | 0.8757 |
| 26 | '0.51724−0.039779*Val+0.089549*Glu−0.022865*Thr−0.0094595*Asn+0.16455*a−ABA+0.0095814*Gln' | 0.8871 |
| 27 | '−0.20349−0.038411*Val+0.082927*Glu−0.11552*Met+0.16941*a−ABA+0.0075867*Gln+0.014559*Pro' | 0.8804 |
| 28 | '2.5204−0.068468*Ile−0.020721*Val−0.067656*His+0.08741*Glu+0.19259*a−ABA+0.0097335*Gln' | 0.8856 |
| 29 | '−2.1547−0.039412*Val+0.08992*Glu+0.14084*a−ABA+0.0070635*Gln+0.01105*Pro' | 0.8729 |
| 30 | '2.8824−0.07091*Ile−0.096778*Phe+0.062631*Glu−0.12092*Cit+0.17963*a−ABA+0.0093556*Gln' | 0.8875 |
| 31 | '5.5825−0.035769*Val+0.083464*Glu−0.11918*Cit−0.024136*Thr+0.13357*a−ABA+0.01808*Pro' | 0.8823 |
| 32 | '−0.45592−0.080646*Phe−0.043377*Leu+0.075016*Glu+0.18258*a−ABA+0.008285*Gln' | 0.8733 |
| 33 | '3.9977−0.060543*Leu−0.039323*His+0.078272*Glu−0.024842*Thr+0.18074*a−ABA+0.016999*Pro' | 0.8776 |
| 34 | '2.9076−0.03547*Val+0.06331*Glu−0.02949*Thr+0.0022279*Trp+0.14609*a−ABA+0.018709*Pro' | 0.8748 |
| 35 | '0.27351−0.082934*Phe−0.045822*Leu+0.079848*Glu+0.18476*a−ABA+0.0093928*Gln−0.021793*Orn' | 0.879 |
| 36 | '1.601−0.067117*Leu−0.05173*His+0.086673*Glu−0.020377*Thr+0.19876*a−ABA+0.0097358*Gln' | 0.8809 |
| 37 | '4.5892−0.027163*Val−0.077233*Phe+0.01704*Tyr+0.079049*Glu+0.15776*a−ABA' | 0.8696 |
| 38 | '1.2119−0.022852*Val−0.031641*Leu−0.052979*His+0.093428*Glu+0.17577*a−ABA+0.009567*Gln' | 0.8795 |
| 39 | '2.1475−0.010779*Tyr−0.061734*Leu+0.076847*Glu−0.026858*Thr+0.17458*a−ABA+0.018119*Pro' | 0.8752 |
| 40 | '1.9702−0.062685*Phe−0.046357*Leu+0.075046*Glu+0.17068*a−ABA+0.01163*Pro' | 0.87 |
| 41 | '4.6367−0.059738*Phe−0.042826*Leu−0.047113*His+0.075885*Glu+0.17909*a−ABA+0.012711*Pro' | 0.8757 |
| 42 | '5.4444−0.026614*Val−0.071224*Phe+0.080594*Glu+0.061076*Met−0.016876*Thr+0.15199*a−ABA' | 0.8719 |
| 43 | '7.0849−0.08315*Ile−0.077912*Phe+0.02326*Tyr−0.055561*His+0.068217*Glu+0.20242*a−ABA' | 0.8762 |
| 44 | '6.3161−0.079143*Ile−0.062697*Phe−0.061234*His+0.067188*Glu+0.19085*a−ABA+0.012668*Pro' | 0.8762 |
| 45 | '1.8881−0.063184*Leu+0.07151*Glu−0.0074859*Met−0.028009*Thr+0.17675*a−ABA+0.017312*Pro' | 0.8696 |
| 46 | '6.4822−0.02525*Val−0.078251*Phe+0.01789*Tyr−0.032526*His+0.079702*Glu+0.16561*a−ABA' | 0.8767 |
| 47 | '−1.0594−0.037486*Val+0.086273*Glu+0.13899*a−ABA+0.0075633*Gln' | 0.8634 |
| 48 | '−2.1008−0.038948*Val+0.089895*Glu−0.0036902*Trp+0.14113*a−ABA+0.0070911*Gln+0.011276*Pro' | 0.8729 |
| 49 | '0.8698−0.028047*Val−0.026472*Leu+0.081493*Glu−0.037081*Asn+0.16777*a−ABA+0.0079963*Gln' | 0.8771 |
| 50 | '−0.34725−0.028817*Val−0.025324*Leu+0.093971*Glu+0.1591*a−ABA+0.009082*Gln−0.023925*Orn' | 0.8795 |

FIG.51

| No. | Formula | ROC_AUC |
|---|---|---|
| 51 | '5.9964−0.027272*Val−0.060634*Phe+0.071283*Glu−0.018063*Asn+0.15427*a-ABA' | 0.8663 |
| 52 | '1.8865−0.1106*Ile−0.086209*His+0.075*Glu+0.18977*a-ABA+0.0076791*Gln+0.010165*Pro' | 0.8809 |
| 53 | '4.6045−0.028954*Val−0.06614 8*Phe+0.076119*Glu+0.02062*Trp+0.1517*a-ABA' | 0.871 |
| 54 | '5.3696−0.070863*Leu+0.072287*Glu−0.13458*Cit−0.035367*Asn+0.16314*a-ABA+0.013423*Pro' | 0.8738 |
| 55 | '6.2172−0.034618*Ile−0.019*Val−0.05395*Phe+0.071509*Glu−0.013384*Thr+0.16996*a-ABA' | 0.8667 |
| 56 | '5.1793−0.032541*Ile−0.019254*Val−0.058754*Phe+0.072043*Glu+0.16269*a-ABA' | 0.8648 |
| 57 | '6.5878−0.028553*Val−0.067318*Phe−0.036373*His+0.077861*Glu+0.030408*Trp+0.16112*a-ABA' | 0.8814 |
| 58 | '−0.90846−0.027782*Val−0.022846*Leu+0.087547*Glu+0.15374*a-ABA+0.0074412*Gln' | 0.8691 |
| 59 | '0.77266−0.064425*Leu−0.059239*His+0.085948*Glu+0.18043*a-ABA+0.0086237*Gln' | 0.8686 |
| 60 | '3.5596−0.079428*Leu+0.076049*Glu−0.18917*Cit−0.03449*Asn+0.17253*a-ABA+0.0099365*Gln' | 0.8757 |
| 61 | '4.1694−0.072671*Ile−0.071386*Phe+0.061496*Glu−0.025941*Thr+0.18567*a-ABA+0.016347*Pro' | 0.8663 |
| 62 | '2.048−0.1073*Phe+0.062029*Glu−0.13022*Cit−0.05178*Trp+0.13479*a-ABA+0.01054*Gln' | 0.8743 |
| 63 | '7.1637−0.022523*Val−0.042143*Phe−0.015967*Leu+0.077314*Glu−0.10875*Cit+0.14457*a-ABA' | 0.8719 |
| 64 | '−0.69984−0.040124*Val+0.092142*Glu+0.0065751*Trp+0.14251*a-ABA+0.0089723*Gln−0.02242*Orn' | 0.8762 |
| 65 | '5.7168−0.031832*Val−0.062037*Phe+0.071299*Glu+0.02909*Trp−0.025497*Asn+0.15795*a-ABA' | 0.8738 |
| 66 | '5.9634−0.023896*Val−0.056475*Phe−0.0092242*Leu+0.07169*Glu−0.01955*Asn+0.1595*a-ABA' | 0.871 |
| 67 | '6.921−0.020173*Val−0.059695*Phe−0.010738*Leu−0.03328*His+0.076265*Glu+0.16371*a-ABA' | 0.8748 |
| 68 | '8.3034−0.026503*Val−0.05081*Phe−0.025043*His+0.076224*Glu−0.088496*Cit+0.14447*a-ABA' | 0.8719 |
| 69 | '7.9638−0.0782*Ile−0.056004*Phe−0.049958*His+0.062795*Glu−0.0088796*Thr+0.1927*a-ABA' | 0.871 |
| 70 | '6.7941−0.080339*Ile−0.069119*Phe−0.056029*His+0.070394*Glu+0.056965*Met+0.18409*a-ABA' | 0.8724 |
| 71 | '5.9002−0.056221*Phe−0.041542*Leu−0.040268*His+0.072122*Glu+0.17539*a-ABA' | 0.87 |
| 72 | '6.7812−0.029869*Val−0.051061*Phe+0.0767*Glu−0.097094*Cit+0.012161*Trp+0.1373*a-ABA' | 0.8696 |
| 73 | '0.55972−0.038859*Val−0.00046329*Tyr+0.080306*Glu−0.033928*Asn+0.14984*a-ABA+0.0080176*Gln' | 0.8719 |
| 74 | '4.9228−0.10271*Ile−0.069672*His+0.068438*Glu+0.17155*a-ABA+0.011462*Pro' | 0.8667 |
| 75 | '5.227−0.023363*Val−0.060051*Phe−0.0072067*Leu+0.076515*Glu+0.15329*a-ABA−0.0061486*Orn' | 0.8705 |
| 76 | '4.9088−0.034915*Val+0.082163*Glu−0.13726*Cit−0.010331*Trp+0.12054*a-ABA+0.013424*Pro' | 0.8672 |
| 77 | '7.4923−0.077319*Ile−0.058821*Phe−0.053657*His+0.063754*Glu+0.1887*a-ABA+1.0259e−007*Orn' | 0.8696 |
| 78 | '−0.29588−0.068111*Leu+0.084007*Glu−0.021968*Thr+0.18537*a-ABA+0.0085821*Gln−0.015116*Orn' | 0.8715 |
| 79 | '4.3801−0.035439*Val+0.069142*Glu−0.079947*Met−0.033516*Asn+0.15366*a-ABA+0.017101*Pro' | 0.8681 |
| 80 | '4.6494−0.036289*Val+0.081874*Glu−0.13751*Cit+0.12001*a-ABA+0.0021822*Orn+0.012669*Pro' | 0.8663 |
| 81 | '5.3446−0.031857*Ile−0.019371*Val−0.058358*Phe+0.072767*Glu+0.16176*a-ABA−0.0040852*Orn' | 0.8629 |
| 82 | '8.3491−0.071545*Ile−0.015106*Val−0.051805*His+0.066876*Glu−0.033214*Asn+0.17694*a-ABA' | 0.8729 |
| 83 | '0.59511−0.12428*Phe−0.058851*His+0.068868*Glu+0.1659*a-ABA+0.010979*Gln' | 0.8639 |
| 84 | '0.44722−0.037489*Val+0.011733*Tyr+0.080782*Glu−0.10748*Met+0.16424*a-ABA+0.0082362*Gln' | 0.8667 |
| 85 | '−0.83472−0.067381*Leu+0.082781*Glu+0.017352*Met−0.025601*Thr+0.18356*a-ABA+0.0078637*Gln' | 0.8719 |
| 86 | '−1.129−0.028966*Val−0.023639*Leu+0.088069*Glu+0.010626*Trp+0.15384*a-ABA+0.0073497*Gln' | 0.8719 |
| 87 | '1.2111−0.0084218*Tyr−0.062714*Leu−0.058875*His+0.084447*Glu+0.18021*a-ABA+0.0086922*Gln' | 0.8696 |
| 88 | '3.7899−0.058473*Phe−0.043285*Leu+0.071671*Glu+0.16621*a-ABA−0.0087375*Orn' | 0.862 |
| 89 | '5.2576−0.064028*Phe−0.042978*Leu−0.041798*His+0.078095*Glu+0.045826*Met+0.17168*a-ABA' | 0.8715 |
| 90 | '5.0856−0.075149*Ile−0.075361*Phe+0.063001*Glu−0.088602*Cit+0.16435*a-ABA+0.011007*Pro' | 0.8705 |
| 91 | '6.849−0.050805*Phe−0.0447*Leu−0.039967*His+0.067525*Glu−0.020036*Asn+0.18089*a-ABA' | 0.8663 |
| 92 | '6.9103−0.041346*Ile−0.025902*Val+0.075489*Glu−0.13203*Cit+0.13453*a-ABA' | 0.8629 |
| 93 | '3.051−0.026759*Val−0.016416*Leu+0.075606*Glu−0.08982*Met+0.15711*a-ABA+0.015109*Pro' | 0.8653 |
| 94 | '0.59489−0.066998*Leu−0.060931*His+0.086684*Glu+0.0097833*Trp+0.1817*a-ABA+0.0085877*Gln' | 0.87 |
| 95 | '1.0632−0.063801*Ile−0.10166*Phe+0.064409*Glu+0.18572*a-ABA+0.0082421*Gln−0.011371*Orn' | 0.8724 |
| 96 | '6.2585−0.067162*Ile−0.014605*Val−0.049259*His+0.073217*Glu+0.16378*a-ABA' | 0.8677 |
| 97 | '7.3616−0.021737*Val−0.029589*Leu+0.080048*Glu−0.12915*Cit−0.010838*Thr+0.14248*a-ABA' | 0.8705 |
| 98 | '−0.57813−0.065855*Leu+0.080837*Glu−0.02495*Thr−0.00056443*Trp+0.18516*a-ABA+0.0078328*Gln' | 0.871 |
| 99 | '2.8636−0.10815*Ile−0.079676*His+0.072485*Glu−0.0042254*Trp+0.18997*a-ABA+0.0081445*Gln' | 0.8748 |
| 100 | '3.4698−0.019635*Val−0.029114*Leu−0.040218*His+0.083439*Glu+0.15538*a-ABA+0.012887*Pro' | 0.8667 |

FIG.53

| No. | Formula | ROC_AUC |
|---|---|---|
| 1 | 'Ile+0.66515*His-0.64228*Glu+0.54058*Cit+0.28678*Asn-1.8575*a-ABA' | 0.8757 |
| 2 | 'Ile+0.68254*His-0.71192*Glu+0.63869*Cit-1.7806*a-ABA' | 0.8738 |
| 3 | 'Ile+0.83334*Phe+0.73217*His-0.95479*Glu+0.59145*Cit-2.5962*a-ABA' | 0.8724 |
| 4 | 'Ile+0.67121*His-0.6109*Glu-0.094707*Trp+0.33033*Asn-1.861*a-ABA' | 0.8724 |
| 5 | 'Ile+0.67106*His-0.64157*Glu+0.31622*Asn-1.9102*a-ABA' | 0.8705 |
| 6 | 'Ile+0.68036*His-0.73888*Glu+0.71294*Cit+0.09706*Trp-1.8376*a-ABA' | 0.8705 |
| 7 | 'Ile+0.66969*His-0.6381*Glu-0.09733*Met+0.32934*Asn-1.8731*a-ABA' | 0.87 |
| 8 | 'Ile+0.86293*Phe+0.74249*His-0.97057*Glu-2.6758*a-ABA' | 0.8677 |
| 9 | 'Ile+0.853*Phe+0.74369*His-0.9223*Glu-0.15812*Trp-2.5792*a-ABA' | 0.8677 |
| 10 | 'Ile+0.69359*His-0.71042*Glu+0.26287*Met-0.03437*Trp-1.9345*a-ABA' | 0.8667 |
| 11 | 'Ile+0.69183*His-0.71915*Glu-0.0018182*Trp-1.8449*a-ABA' | 0.8663 |
| 12 | 'Ile+0.6918*His-0.71967*Glu-1.8459*a-ABA' | 0.8658 |
| 13 | 'Ile+0.78198*Phe+0.7209*His-0.88364*Glu+0.25668*Asn-2.6502*a-ABA' | 0.8658 |
| 14 | 'Ile+1.2368*Phe-1.0719*Glu+1.1375*Cit+0.32653*Trp-2.7718*a-ABA' | 0.8644 |
| 15 | 'Ile+0.69309*His-0.72024*Glu+0.24294*Met-1.9452*a-ABA' | 0.8639 |
| 16 | 'Ile+1.1556*Phe-0.90428*Glu+0.8107*Cit+0.22482*Asn-2.5932*a-ABA' | 0.8596 |
| 17 | 'Ile+1.2325*Phe-0.97906*Glu+0.89102*Cit-2.6061*a-ABA' | 0.8592 |
| 18 | 'Ile+1.2401*Phe-0.98113*Glu+0.88784*Cit-0.074915*Met-2.583*a-ABA' | 0.8587 |
| 19 | 'Ile+1.201*Phe-0.9498*Glu+0.10513*Trp+0.25049*Asn-2.7648*a-ABA' | 0.854 |
| 20 | 'Ile+1.2068*Phe-0.90585*Glu-0.34426*Met+0.3119*Asn-2.5862*a-ABA' | 0.853 |
| 21 | 'Ile+1.1869*Phe-0.91208*Glu+0.26704*Asn-2.6989*a-ABA' | 0.8521 |
| 22 | 'Ile+1.2923*Phe-1.0052*Glu-0.064049*Met-2.707*a-ABA' | 0.8507 |
| 23 | 'Ile+1.3163*Phe-1.0665*Glu-0.19419*Met+0.18981*Trp-2.7821*a-ABA' | 0.8488 |
| 24 | 'Ile+1.2958*Phe-1.0552*Glu+0.16955*Trp-2.8306*a-ABA' | 0.8469 |
| 25 | 'Phe-0.69872*Glu+0.92908*Cit+0.457*Trp-0.082359*Asn-1.4677*a-ABA' | 0.8445 |
| 26 | 'Phe+0.4276*His-0.76249*Glu+0.76368*Cit+0.30842*Trp-1.7173*a-ABA' | 0.8426 |
| 27 | 'Phe-0.68219*Glu+0.90146*Cit-0.051207*Met+0.4447*Trp-1.4705*a-ABA' | 0.8417 |
| 28 | 'Phe-0.68279*Glu+0.90417*Cit+0.44141*Trp-1.4913*a-ABA' | 0.8407 |
| 29 | 'Ile+0.60166*Phe+0.58269*His+0.77463*Cit+0.58965*Asn-2.2678*a-ABA' | 0.836 |
| 30 | 'Phe+0.43739*His-0.67978*Glu+0.53222*Cit-1.5726*a-ABA' | 0.8351 |
| 31 | 'Ile-0.70318*Glu+1.1887*Cit+0.45053*Trp+0.22075*Asn-1.7325*a-ABA' | 0.8351 |
| 32 | 'Phe+0.44119*His-0.68343*Glu+0.54078*Cit+0.068328*Met-1.6138*a-ABA' | 0.8346 |
| 33 | 'Phe+0.42625*His-0.72526*Glu-0.047572*Met+0.19485*Trp-1.6785*a-ABA' | 0.8341 |
| 34 | 'Ile+0.62649*Phe+0.5918*His+0.63285*Asn-2.3658*a-ABA' | 0.8327 |
| 35 | 'Phe+0.43942*His-0.67408*Glu+0.05895*Met+0.034247*Asn-1.6433*a-ABA' | 0.8303 |
| 36 | 'Phe+0.43509*His-0.67598*Glu-1.6016*a-ABA' | 0.8299 |
| 37 | 'Phe+0.43731*His-0.67074*Glu+0.041794*Asn-1.6185*a-ABA' | 0.8299 |
| 38 | 'Phe+0.43882*His-0.67853*Glu+0.087471*Met-1.6429*a-ABA' | 0.8299 |
| 39 | 'Ile-0.55619*Glu+0.81611*Cit+0.30844*Asn-1.5324*a-ABA' | 0.8294 |
| 40 | 'Ile-0.62989*Glu+0.96209*Cit+0.82737*Met-1.7848*a-ABA' | 0.8289 |
| 41 | 'Phe-0.63956*Glu+0.30245*Trp-1.469*a-ABA' | 0.8284 |
| 42 | 'Phe-0.64147*Glu+0.30397*Trp-0.010663*Asn-1.4659*a-ABA' | 0.8284 |
| 43 | 'Phe-0.64344*Glu+0.064742*Met+0.30039*Trp-0.018388*Asn-1.4898*a-ABA' | 0.8275 |
| 44 | 'Ile+0.87829*Phe+0.72533*His-1.0806*Glu+1.5885*Cit-1.5634*Met' | 0.8261 |
| 45 | 'Ile+0.89271*Phe+1.0545*Cit+0.37209*Met+0.54636*Asn-2.3835*a-ABA' | 0.8251 |
| 46 | 'Phe-0.55179*Glu+0.038564*Asn-1.3218*a-ABA' | 0.8247 |
| 47 | 'Phe-0.55719*Glu-1.3075*a-ABA' | 0.8237 |
| 48 | 'Ile+0.81561*Phe+0.61741*His-2.359*a-ABA' | 0.8233 |
| 49 | 'Ile-0.72023*Glu+0.71487*Met+0.27921*Trp-1.971*a-ABA' | 0.8233 |
| 50 | 'Ile+0.98671*Phe+1.4445*Cit+1.016*Met+0.10926*Trp-2.5925*a-ABA' | 0.8233 |

FIG.54

| No. | Formula | ROC_AUC |
|---|---|---|
| 51 | 'Phe-0.56487*Glu+0.26562*Met-1.4253*a-ABA' | 0.8228 |
| 52 | 'Ile-0.64002*Glu+0.88045*Met-1.8832*a-ABA' | 0.8228 |
| 53 | 'Ile+0.59042*His-0.22794*Trp+0.59776*Asn-1.6984*a-ABA' | 0.8228 |
| 54 | 'Ile+0.91521*Phe+1.0193*Cit+0.59399*Asn-2.2684*a-ABA' | 0.8228 |
| 55 | 'Ile+0.91521*Phe+1.0193*Cit+0.59399*Asn-2.2684*a-ABA' | 0.8228 |
| 56 | 'Phe-0.56405*Glu+0.26147*Met+0.0050187*Asn-1.4254*a-ABA' | 0.8223 |
| 57 | 'Ile+0.93533*Phe+0.3379*Met+0.60974*Asn-2.5066*a-ABA' | 0.8218 |
| 58 | 'Ile+0.59612*His+0.42476*Met-0.26664*Trp+0.54738*Asn-1.8398*a-ABA' | 0.8209 |
| 59 | 'Ile+0.66687*His-0.92204*Glu+1.7847*Cit-0.93003*Met+0.42641*Trp' | 0.8204 |
| 60 | 'Ile-0.55395*Glu+0.35337*Asn-1.608*a-ABA' | 0.8199 |
| 61 | 'Ile+1.076*Phe-1.2945*Glu+2.9087*Cit+0.70421*Trp' | 0.8199 |
| 62 | 'Ile+1.1995*Phe-1.0559*Glu+1.883*Cit-1.3329*Met+0.13619*Asn' | 0.8199 |
| 63 | 'Ile+0.95181*Phe-0.11606*Trp+0.65193*Asn-2.339*a-ABA' | 0.819 |
| 64 | 'Ile+1.0833*Phe+1.5062*Cit+0.2147*Trp-2.3108*a-ABA' | 0.819 |
| 65 | 'Ile+1.0894*Phe+1.3176*Cit-2.2255*a-ABA' | 0.8185 |
| 66 | 'Ile+1.3044*Phe-1.3694*Glu+2.6758*Cit-1.9341*Met+0.85045*Trp' | 0.8185 |
| 67 | 'Ile+0.6748*His-0.93419*Glu+1.9591*Cit+0.35997*Trp-0.03893*Asn' | 0.8185 |
| 68 | 'Ile-0.64033*Glu+0.26662*Trp+0.31362*Asn-1.7468*a-ABA' | 0.8176 |
| 69 | 'Ile+0.59155*His+1.0336*Cit+1.0263*Met-1.9749*a-ABA' | 0.8171 |
| 70 | 'Ile+0.69401*Phe+0.72133*His-1.0562*Glu+1.8977*Cit' | 0.8162 |
| 71 | 'Ile+1.0867*Phe-1.0805*Glu+2.1977*Cit' | 0.8162 |
| 72 | 'Ile+1.0518*Phe+1.1436*Met-0.099066*Trp-2.7106*a-ABA' | 0.8157 |
| 73 | 'Ile+0.97961*Phe+0.7533*His-1.1806*Glu-1.7723*Met+0.12863*Trp' | 0.8119 |
| 74 | 'Phe+0.39926*His-0.90945*Glu+1.6666*Cit-1.0954*Met+0.6104*Trp' | 0.811 |
| 75 | 'His-1.4602*Glu+2.7086*Cit+1.4376*Trp-2.3514*a-ABA' | 0.81 |
| 76 | 'Ile+0.69734*His-0.87313*Glu-0.74659*Met+0.15968*Trp' | 0.8095 |
| 77 | 'Ile+1.164*Phe-2.3924*a-ABA' | 0.8095 |
| 78 | 'Phe-0.87861*Glu+2.0329*Cit+0.70566*Trp' | 0.8077 |
| 79 | 'Ile-0.94251*Glu+2.3597*Cit-0.59865*Met+0.80769*Trp+0.02342*Asn' | 0.8077 |
| 80 | 'Phe+1.2378*Cit+0.77916*Met+0.3282*Trp+0.1752*Asn-1.6998*a-ABA' | 0.8077 |
| 81 | 'Phe+0.43471*His-1.0444*Glu+2.0943*Cit+0.65976*Trp-0.35046*Asn' | 0.8072 |
| 82 | 'Ile+0.67969*His-0.75286*Glu-0.88909*Met+0.27556*Asn' | 0.8067 |
| 83 | 'Ile+0.69685*His-0.81542*Glu+0.12098*Asn' | 0.8048 |
| 84 | 'Ile+0.70403*His-0.869*Glu+0.078269*Trp' | 0.8048 |
| 85 | 'Phe+1.0188*Cit+1.0807*Met-1.617*a-ABA' | 0.8039 |
| 86 | 'Phe+1.0188*Cit+1.0807*Met-1.617*a-ABA' | 0.8039 |
| 87 | 'Ile+0.78113*Phe+0.7557*His-1.1212*Glu' | 0.8034 |
| 88 | 'Ile+0.78577*Phe+0.75696*His-1.1263*Glu-0.014848*Asn' | 0.8029 |
| 89 | 'Ile+1.596*Cit+0.4351*Trp-1.4695*a-ABA' | 0.8015 |
| 90 | 'Ile+1.596*Cit+0.4351*Trp-1.4695*a-ABA' | 0.8015 |
| 91 | 'Ile-0.71276*Glu+1.6948*Cit' | 0.7973 |
| 92 | 'Phe-0.63472*Glu+1.1807*Cit-0.35677*Met' | 0.7963 |
| 93 | 'Phe-0.65137*Glu+1.2047*Cit-0.27236*Met-0.10121*Asn' | 0.7963 |
| 94 | 'His-1.2858*Glu+0.98056*Trp+0.17006*Asn-2.3122*a-ABA' | 0.7949 |
| 95 | 'Ile+1.3547*Phe-1.1695*Glu-1.3359*Met' | 0.7944 |
| 96 | 'Ile-0.68745*Glu+1.6685*Cit+0.11494*Asn' | 0.7944 |
| 97 | 'Phe-0.67404*Glu+1.2979*Cit-0.15109*Asn' | 0.7944 |
| 98 | 'Ile+0.082455*Trp+0.59442*Asn-1.5917*a-ABA' | 0.7921 |
| 99 | 'Phe+0.82425*Cit+0.27951*Asn-1.2655*a-ABA' | 0.7911 |
| 100 | 'Phe+0.45922*His-0.82665*Glu+1.4316*Cit-0.18504*Asn' | 0.7906 |

FIG.55

| AMINO ACID | FREQUENCY OF APPEARANCE |
|---|---|
| Glu | 493 |
| ABA | 493 |
| Val | 253 |
| Phe | 205 |
| Leu | 201 |
| Gln | 168 |
| Ile | 159 |
| His | 153 |
| Pro | 147 |
| Cit | 130 |
| Thr | 109 |
| Asn | 90 |
| Met | 70 |
| Tyr | 70 |
| Orn | 68 |
| Trp | 64 |
| Ser | 0 |
| Gly | 0 |
| Ala | 0 |
| Lys | 0 |
| Arg | 0 |

METHOD, APPARATUS, SYSTEM, PROGRAM, AND COMPUTER-READABLE RECORDING MEDIUM FOR EVALUATING COLORECTAL CANCER

This application is a Continuation of PCT/JP2007/074270, filed Dec. 18, 2007, which claims priority from Japanese patent application JP 2006-344935 filed Dec. 21, 2006. The contents of each of the aforementioned application are incorporated herein by reference in their entirety.

BACKGROUND OF THE INVENTION

1. Field of the Invention

The present invention relates to a method of evaluating colorectal cancer, a colorectal cancer-evaluating apparatus, a colorectal cancer-evaluating method, a colorectal cancer-evaluating system, a colorectal cancer-evaluating program and recording medium, which utilize the concentration of amino acids in blood (plasma).

2. Description of the Related Art

The number of deaths from colorectal cancer in Japan in 2003 is 21962 males and 18373 females, and the number of deaths from colorectal cancer ranks fourth in males among the deaths from cancers, while the number of deaths from colorectal cancer ranks first in females among the deaths from cancers. The morbidity rate of colorectal cancer in recent years tends to be leveling off.

The five-year survival rate of early colorectal cancer (A and B in Dukes classification) is 80% or higher, and particularly, the five-year survival rate of class A colorectal cancer (tumor remaining within the colorectal wall) is about 90%.

However, the five-year survival rate of progressive colorectal cancer, particularly in class D of Dukes classification (having distal metastasis to the peritoneum, liver, lung and the like) is extremely lowered to about 10%. Therefore, early detection is important for the healing of colorectal cancer.

Here, diagnosis of colorectal cancer includes diagnosis based on the immunological fecal occult blood reaction, diagnosis by colonoscopy, and the like.

However, diagnosis based on a fecal occult blood test does not serve as definitive diagnosis, and most of the persons with positive-finding are false-positive. Furthermore, in regard to early colorectal cancer, there is a concern that both the detection sensitivity and the detection specificity become lower in the diagnosis based on a fecal occult blood test or the diagnosis by colonoscopy. In particular, early cancer in the right side colon is frequently overlooked when diagnosed by a fecal occult blood test. Diagnostic imaging by CT (computer tomography), MRI (magnetic resonance imaging), PET (positron emission computerized-tomography) or the like is not suitable for the diagnosis of colorectal cancer.

On the other hand, colorectal biopsy by colonoscopy serves as definitive diagnosis, but is a highly invasive examination, and implementing colonoscopic examination at the screening stage is not practical. Furthermore, invasive diagnosis such as colonoscopy gives a burden to patients, such as accompanying pain, and there may also be a risk of bleeding upon examination, or the like.

Therefore, from the viewpoints of a physical burden imposed on patients and of cost-benefit performance, it is desirable to narrow down the target range of test subjects with high possibility of onset of colorectal cancer, and to subject those people to treatment. Specifically, it is desirable that test subjects are selected by a less invasive method, the target range of the selected test subjects is narrowed by subjecting the selected test subjects to a colonoscopic examination, and the test subjects who are definitively diagnosed as having colorectal cancer are subjected to treatment.

Incidentally, it is known that the concentrations of amino acids in blood change as a result of onset of cancer. For example, Cynober ("Cynober, L. ed., Metabolic and therapeutic aspects of amino acids in clinical nutrition. 2nd ed., CRC Press.") has reported that, for example, the amount of consumption increases in cancer cells, for glutamine mainly as an oxidation energy source, for arginine as a precursor of nitrogen oxide and polyamine, and for methionine through the activation of the ability of cancer cells to take in methionine, respectively. Vissers, et al. ("Vissers, Y. L J., et. al., Plasma arginine concentration are reduced in cancer patients: evidence for arginine deficiency?, The American Journal of Clinical Nutrition, 2005. 81, p 1142-1146") and Park ("Park, K. G., et. al., Arginine metabolism in benign and malignant disease of breast and colon: evidence for possible inhibition of tumor-infiltrating macropharges., Nutrition, 1991. 7, p. 185-188") have reported that the amino acid composition in plasma in colorectal cancer patients is different from that of healthy individuals.

However, there is a problem that the development of techniques of diagnosing the presence or absence of onset of colorectal cancer with a plurality of amino acids as explanatory variables is not conducted from the viewpoint of time and cost and is not practically used.

SUMMARY OF THE INVENTION

It is an object of the present invention to at least partially solve the problems in the conventional technology. The present invention is made in view of the problem described above, and an object of the present invention is to provide a method of evaluating colorectal cancer, a colorectal cancer-evaluating apparatus, a colorectal cancer-evaluating method, a colorectal cancer-evaluating system, a colorectal cancer-evaluating program and a recording medium, which are capable of evaluating a colorectal cancer state accurately by utilizing the concentration of amino acids related to a colorectal cancer state among amino acids in blood.

The present inventors have made extensive study for solving the problem described above, and as a result they have identified amino acids which are useful in discrimination of between 2 groups of colorectal cancer and colorectal cancer-free (specifically, amino acids varying with a statistically significant difference between the 2 groups), and have found that multivariate discriminant (correlation equation, index) including the concentrations of the identified amino acids as explanatory variables correlates significantly with the state (specifically, progress of a morbid state) of colorectal cancer (specifically, early colorectal cancer), and the present invention was thereby completed.

To solve the problem and achieve the object described above, a method of evaluating colorectal cancer according to one aspect of the present invention includes a measuring step of measuring amino acid concentration data on the concentration value of amino acid in blood collected from a subject to be evaluated, and a concentration value criterion evaluating step of evaluating a colorectal cancer state in the subject, based on the concentration value of at least one of Arg, Cys, Orn, Trp, Glu, ABA (ABA is α-aminobutyric acid), Val, Phe, Leu, Gln, Ile and His contained in the amino acid concentration data of the subject measured at the measuring step.

Another aspect of the present invention is the method of evaluating colorectal cancer, wherein the concentration value criterion evaluating step further includes a concentration value criterion discriminating step of discriminating between colorectal cancer and colorectal cancer-free in the subject, based on the concentration value of at least one of Arg, Cys, Orn, Trp, Glu, ABA, Val, Phe, Leu, Gln, Ile and His contained in the amino acid concentration data of the subject measured at the measuring step.

Still another aspect of the present invention is the method of evaluating colorectal cancer, wherein the concentration criterion evaluating step further includes a discriminant value calculating step of calculating a discriminant value that is a value of multivariate discriminant, based on both the concentration value of at least one of Arg, Cys, Orn, Trp, Glu, ABA, Val, Phe, Leu, Gln, Ile and His contained in the amino acid concentration data of the subject measured at the measuring step and a previously established multivariate discriminant with the concentration of the amino acid as explanatory variable, and a discriminant value criterion evaluating step of evaluating the colorectal cancer state in the subject, based on the discriminant value calculated at the discriminant value calculating step, wherein the multivariate discriminant contains at least one of Arg, Cys, Orn, Trp, Glu, ABA, Val, Phe, Leu, Gln, Ile and His as the explanatory variable.

Still another aspect of the present invention is the method of evaluating colorectal cancer, wherein the discriminant value criterion evaluating step further includes a discriminant value criterion discriminating step of discriminating between colorectal cancer and colorectal cancer-free in the subject based on the discriminant value calculated at the discriminant value calculating step.

Still another aspect of the present invention is the method of evaluating colorectal cancer, wherein the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant.

Still another aspect of the present invention is the method of evaluating colorectal cancer, wherein the multivariate discriminant is formula 1 or 2:

$$a_1 \times Orn/(Trp+His) + b_1'(ABA+Ile)/Leu + c_1 \quad \text{(formula 1)}$$

$$a_2 \times Gln/Val + b_2 \times Cit/ABA + c_2 \times Thr/Glu + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

Still another aspect of the present invention is the method of evaluating colorectal cancer, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating colorectal cancer, wherein the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

The present invention also relates to a colorectal cancer-evaluating apparatus, the colorectal cancer-evaluating apparatus according to one aspect of the present invention includes a control unit and a memory unit to evaluate a colorectal cancer state in a subject to be evaluated. The control unit includes a discriminant value-calculating unit that calculates a discriminant value that is a value of multivariate discriminant, based on both the concentration value of at least one of Arg, Cys, Orn, Trp, Glu, ABA, Val, Phe, Leu, Gln, Ile and His contained in previously obtained amino acid concentration data on the concentration value of amino acid in the subject and a multivariate discriminant with the concentration of the amino acid as explanatory variable stored in the memory unit, where at least one of Arg, Cys, Orn, Trp, Glu, ABA, Val, Phe, Leu, Gln, Ile and His is contained as the explanatory variable, and a discriminant value criterion-evaluating unit that evaluates the colorectal cancer state in the subject, based on the discriminant value calculated by the discriminant value-calculating unit.

Another aspect of the present invention is the colorectal cancer-evaluating apparatus, wherein the discriminant value criterion-evaluating unit further includes a discriminant value criterion-discriminating unit that discriminates between colorectal cancer and colorectal cancer-free in the subject based on the discriminant value calculated by the discriminant value-calculating unit.

Still another aspect of the present invention is the colorectal cancer-evaluating apparatus, wherein the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant.

Still another aspect of the present invention is the colorectal cancer-evaluating apparatus, wherein the multivariate discriminant is formula 1 or 2:

$$a_1 \times Orn/(Trp+His) + b_1 \times (ABA+Ile)/Leu + c_1 \quad \text{(formula 1)}$$

$$a_2 \times Gln/Val + b_2 \times Cit/ABA + c_2 \times Thr/Glu + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

Still another aspect of the present invention is the colorectal cancer-evaluating apparatus, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the colorectal cancer-evaluating apparatus, wherein the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

Still another aspect of the present invention is the colorectal cancer-evaluating apparatus, wherein the control unit further includes a multivariate discriminant-preparing unit that prepares the multivariate discriminant stored in the memory unit, based on colorectal cancer state information containing the amino acid concentration data and colorectal cancer state index data on an index for indicating the colorectal cancer state, stored in the memory unit. The multivariate discriminant-preparing unit further includes a candidate multivariate discriminant-preparing unit that prepares a candidate multivariate discriminant that is a candidate of the multivariate discriminant, based on a predetermined discriminant-preparing method from the colorectal cancer state information, a candidate multivariate discriminant-verifying unit that verifies the candidate multivariate discriminant prepared by the candidate multivariate discriminant-preparing unit, based on a predetermined verifying method, and an explanatory variable-selecting unit that selects an explanatory variable of the candidate multivariate discriminant based on a predetermined explanatory variable-selecting method from the verification result obtained by the candidate multivariate discriminant-verifying unit, thereby selecting a combination of the amino acid concentration data contained in the colorectal cancer state information used in preparing the candidate multivariate discriminant. The multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the explanatory variable-selecting unit.

The present invention also relates to a colorectal cancer-evaluating method, one aspect of the present invention is the colorectal cancer-evaluating method of evaluating a colorectal cancer state in a subject to be evaluated. The method is carried out with an information processing apparatus including a control unit and a memory unit. The method includes (i) a discriminant value calculating step of calculating a discriminant value that is a value of multivariate discriminant, based on both the concentration value of at least one of Arg, Cys, Orn, Trp, Glu, ABA, Val, Phe, Leu, Gln, Ile and His contained in previously obtained amino acid concentration data on the concentration value of amino acid in the subject and a multivariate discriminant with the concentration of the amino acid as explanatory variable stored in the memory unit, where at least one of Arg, Cys, Orn, Trp, Glu, ABA, Val, Phe, Leu, Gln, Ile and His is contained as the explanatory variable, and (ii) a discriminant value criterion evaluating step of evaluating the colorectal cancer state in the subject, based on the discriminant value calculated at the discriminant value calculating step. The steps (i) and (ii) are executed by the control unit.

Another aspect of the present invention is the colorectal cancer-evaluating method, wherein the discriminant value criterion evaluating step further includes a discriminant value criterion discriminating step of discriminating between colorectal cancer and colorectal cancer-free in the subject based on the discriminant value calculated at the discriminant value calculating step.

Still another aspect of the present invention is the colorectal cancer-evaluating method, wherein the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant.

Still another aspect of the present invention is the colorectal cancer-evaluating method, wherein the multivariate discriminant is formula 1 or 2:

$$a_1 \times Orn/(Trp+His) + b_1 \times (ABA+Ile)/Leu + c_1 \quad \text{(formula 1)}$$

$$a_2 \times Gln/Val + b_2 \times Cit/ABA + c_2 \times Thr/Glu + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

Still another aspect of the present invention is the colorectal cancer-evaluating method, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the colorectal cancer-evaluating method, wherein the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

Still another aspect of the present invention is the colorectal cancer-evaluating method, wherein the method further includes a multivariate discriminant preparing step of preparing the multivariate discriminant stored in the memory unit, based on colorectal cancer state information containing the amino acid concentration data and colorectal cancer state index date on an index for indicating the colorectal cancer state, stored in the memory unit that is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the colorectal cancer state information, a candidate multivariate discriminant verifying step of verifying the candidate multivariate discriminant prepared at the candidate multivariate preparing step, based on a predetermined verifying method, and an explanatory variable selecting step of selecting explanatory variable of the candidate multivariate discriminant based on a predetermined explanatory variable-selecting method from the verification result obtained at the candidate multivariate discriminant verifying step, thereby selecting a combination of the amino acid concentration data contained in the colorectal cancer state information used in preparing the candidate multivariate discriminant. At the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the explanatory variable selecting step.

The present invention also relates to a colorectal cancer-evaluating system, the colorectal cancer-evaluating system according to one aspect of the present invention includes a colorectal cancer-evaluating apparatus including a control unit and a memory unit to evaluate a colorectal cancer state in a subject to be evaluated and an information communication terminal apparatus that provides amino acid concentration data on the concentration value of amino acid in the subject connected to each other communicatively via a network. The information communication terminal apparatus includes an amino acid concentration data-sending unit that transmits the amino acid concentration data of the subject to the colorectal cancer-evaluating apparatus, and an evaluation result-receiving unit that receives the evaluation result of the colorectal cancer state of the subject transmitted from the colorectal cancer-evaluating apparatus. The control unit of the colorectal cancer-evaluating apparatus includes an amino acid concentration data-receiving unit that receives the amino acid concentration data of the subject transmitted from the information communication terminal apparatus, a discriminant value-calculating unit that calculates a discriminant value that is a value of multivariate discriminant, based on both the concentration value of at least one of Arg, Cys, Orn, Trp, Glu, ABA, Val, Phe, Leu, Gln, Ile and His contained in the amino acid concentration data of the subject received by the amino acid concentration data-receiving unit and a multivariate discriminant with the concentration of the amino acid as explanatory variable stored in the memory unit, where at least one of Arg, Cys, Orn, Trp, Glu, ABA, Val, Phe, Leu, Gln, Ile and His is contained as the explanatory variable, a discriminant value criterion-evaluating unit that evaluates the colorectal cancer state in the subject, based on the discriminant value calculated by the discriminant value-calculating unit, and an evaluation result-sending unit that transmits the evaluation result of the subject obtained by the discriminant value criterion-evaluating unit to the information communication terminal apparatus.

Another aspect of the present invention is the colorectal cancer-evaluating system, wherein the discriminant value criterion-evaluating unit further includes a discriminant value criterion-discriminating unit that discriminates between colorectal cancer and colorectal cancer-free in the subject based on the discriminant value calculated by the discriminant value-calculating unit.

Still another aspect of the present invention is the colorectal cancer-evaluating system, wherein the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant.

Still another aspect of the present invention is the colorectal cancer-evaluating system, wherein the multivariate discriminant is formula 1 or 2:

$$a_1 \times Orn/(Trp+His) + b_1 \times (ABA+Ile)/Leu + c_1 \quad \text{(formula 1)}$$

$$a_2 \times Gln/Val + b_2 \times Cit/ABA + c_2 \times Thr/Glu + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

Still another aspect of the present invention is the colorectal cancer-evaluating system, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the colorectal cancer-evaluating system, wherein the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

Still another aspect of the present invention is the colorectal cancer-evaluating system, wherein the control unit of the colorectal cancer-evaluating apparatus further includes a multivariate discriminant-preparing unit that prepares the multivariate discriminant stored in the memory unit, based on colorectal cancer state information containing the amino acid concentration data and colorectal cancer state index data on an index for indicating the colorectal cancer state, stored in the memory unit. The multivariate discriminant-preparing unit further includes a candidate multivariate discriminant-preparing unit that prepares a candidate multivariate discriminant that is a candidate of the multivariate discriminant, based on a predetermined discriminant-preparing method from the colorectal cancer state information, a candidate multivariate discriminant-verifying unit that verifies the candidate multivariate discriminant prepared by the candidate multivariate discriminant-preparing unit, based on a predetermined verifying method, and an explanatory variable-selecting unit that selects an explanatory variable of the candidate multivariate discriminant based on a predetermined explanatory variable-selecting method from the verification result obtained by the candidate multivariate discriminant-verifying unit, thereby selecting a combination of the amino acid concentration data contained in the colorectal cancer state information used in preparing the candidate multivariate discriminant. The multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit and the explanatory variable-selecting unit.

The present invention also relates to a colorectal cancer-evaluating program product, one aspect of the present invention is the colorectal cancer-evaluating program product that makes an information processing apparatus including a control unit and a memory unit execute a method of evaluating a colorectal cancer state in a subject to be evaluated. The method includes (i) a discriminant value calculating step of calculating a discriminant value that is a value of multivariate discriminant, based on both the concentration value of at least one of Arg, Cys, Orn, Trp, Glu, ABA, Val, Phe, Leu, Gln, Ile and His contained in previously obtained amino acid concentration data on the concentration value of amino acid in the subject and a multivariate discriminant with the concentration of the amino acid as explanatory variable stored in the memory unit, where at least one of Arg, Cys, Orn, Trp, Glu, ABA, Val, Phe, Leu, Gln, Ile and His is contained as the explanatory variable, and (ii) a discriminant value criterion evaluating step of evaluating the colorectal cancer state in the subject, based on the discriminant value calculated at the discriminant value calculating step. The steps (i) and (ii) are executed by the control unit.

Another aspect of the present invention is the colorectal cancer-evaluating program product, wherein the discriminant value criterion evaluating step further includes a discriminant value criterion discriminating step of discriminating between colorectal cancer and colorectal cancer-free in the subject based on the discriminant value calculated at the discriminant value calculating step.

Still another aspect of the present invention is the colorectal cancer-evaluating program product, wherein the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant.

Still another aspect of the present invention is the colorectal cancer-evaluating program product, wherein the multivariate discriminant is formula 1 or 2:

$$a_1 \times Orn/(Trp+His)+b_1 \times (ABA+Ile)/Leu+c_1 \qquad \text{(formula 1)}$$

$$a_2 \times Gln/Val+b_2 \times Cit/ABA+c_2 \times Thr/Glu+d_2 \qquad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

Still another aspect of the present invention is the colorectal cancer-evaluating program product, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the colorectal cancer-evaluating program product, wherein the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

Still another aspect of the present invention is the colorectal cancer-evaluating program product, wherein the method further includes a multivariate discriminant preparing step of preparing the multivariate discriminant stored in the memory unit, based on colorectal cancer state information containing the amino acid concentration data and colorectal cancer state index date on an index for indicating the colorectal cancer state, stored in the memory unit that is executed by the control unit. The multivariate discriminant preparing step further includes a candidate multivariate discriminant preparing step of preparing a candidate multivariate discriminant that is a candidate of the multivariate discriminant, based on a predetermined discriminant-preparing method from the colorectal cancer state information, a candidate multivariate discriminant verifying step of verifying the candidate multivariate discriminant prepared at the candidate multivariate preparing step, based on a predetermined verifying method, and an explanatory variable selecting step of selecting explanatory variable of the candidate multivariate discriminant based on a predetermined explanatory variable-selecting method from the verification result obtained at the candidate multivariate discriminant verifying step, thereby selecting a combination of the amino acid concentration data contained in the colorectal cancer state information used in preparing the candidate multivariate discriminant. At the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step and the explanatory variable selecting step.

The present invention also relates to a recording medium, the recording medium according to one aspect of the present invention includes the colorectal cancer-evaluating program product described above.

According to the method of evaluating colorectal cancer of the present invention, amino acid concentration data on the concentration value of amino acid in blood collected from a subject to be evaluated is measured, and a colorectal cancer state in the subject is evaluated based on the concentration value of at least one of Arg, Cys, Orn, Trp, Glu, ABA, Val, Phe, Leu, Gln, Ile and His contained in the measured amino acid concentration data of the subject. Thus, the concentrations of the amino acids which among amino acids in blood, are related to a colorectal cancer state can be utilized to bring about an effect of enabling accurate evaluation of a colorectal cancer state.

According to the method of evaluating colorectal cancer of the present invention, between colorectal cancer and colorectal cancer-free in the subject is discriminated based on the concentration value of at least one of Arg, Cys, Orn, Trp, Glu, ABA, Val, Phe, Leu, Gln, Ile and His contained in the measured amino acid concentration data of the subject. Thus, the concentrations of the amino acids which among amino acids in blood, are useful for discriminating between the 2 groups of colorectal cancer and colorectal cancer-free can be utilized to bring about an effect of enabling accurate discrimination between the 2 groups of colorectal cancer and colorectal cancer-free.

According to the method of evaluating colorectal cancer of the present invention, a discriminant value that is a value of multivariate discriminant is calculated based on both the concentration value of at least one of Arg, Cys, Orn, Trp, Glu, ABA, Val, Phe, Leu, Gln, Ile and His contained in the measured amino acid concentration data of the subject and a previously established multivariate discriminant with the concentration of the amino acid as explanatory variable, where at least one of Arg, Cys, Orn, Trp, Glu, ABA, Val, Phe, Leu, Gln, Ile and His is contained as the explanatory variable, and the colorectal cancer state in the subject is evaluated based on the calculated discriminant value. Thus, a discriminant value obtained in a multivariate discriminant correlated significantly with a colorectal cancer state can be utilized to bring about an effect of enabling accurate evaluation of a colorectal cancer state.

According to the method of evaluating colorectal cancer of the present invention, between colorectal cancer and colorectal cancer-free in the subject is discriminated based on the calculated discriminant value. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

According to the method of evaluating colorectal cancer of the present invention, the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the method of evaluating colorectal cancer of the present invention, the multivariate discriminant is formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the method of evaluating colorectal cancer of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the method of evaluating colorectal cancer of the present invention, the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating apparatus, the colorectal cancer-evaluating method and the colorectal cancer-evaluating program of the present invention, a discriminant value that is a value of multivariate discriminant is calculated based on both the concentration value of at least one of Arg, Cys, Orn, Trp, Glu, ABA, Val, Phe, Leu, Gln, Ile and His contained in previously obtained amino acid concentration data on the concentration value of amino acid in the subject and a multivariate discriminant with the concentration of the amino acid as explanatory variable stored in the memory unit, where at least one of Arg, Cys, Orn, Trp, Glu, ABA, Val, Phe, Leu, Gln, Ile and His is contained as the explanatory variable, and the colorectal cancer state in the subject is evaluated based on the calculated discriminant value. Thus, a discriminant value obtained in a multivariate discriminant correlated significantly with a colorectal cancer state can be utilized to bring about an effect of enabling accurate evaluation of a colorectal cancer state.

According to the colorectal cancer-evaluating apparatus, the colorectal cancer-evaluating method and the colorectal cancer-evaluating program of the present invention, between colorectal cancer and colorectal cancer-free in the subject is discriminated based on the calculated discriminant value. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

According to the colorectal cancer-evaluating apparatus, the colorectal cancer-evaluating method and the colorectal cancer-evaluating program of the present invention, the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating apparatus, the colorectal cancer-evaluating method and the colorectal cancer-evaluating program of the present invention, the multivariate discriminant is formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating apparatus, the colorectal cancer-evaluating method and the colorectal cancer-evaluating program of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating apparatus, the colorectal cancer-evaluating method and the colorectal cancer-evaluating program of the present invention, the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating apparatus, the colorectal cancer-evaluating method and the colorectal cancer-evaluating program of the present invention, a multivariate discriminant stored in a memory unit is prepared based on the colorectal cancer state information containing the amino acid concentration data and colorectal cancer state index data on an index for indicating the colorectal cancer state, stored in the memory unit. Specifically, (1) a candidate multivariate discriminant is prepared from the colorectal cancer state information, according to a predetermined discriminant-preparing method, (2) the prepared candidate multivariate discriminant is verified based on a predetermined verification method, (3) based on a predetermined explanatory variable-selecting method, explanatory variables in the candidate multivariate discriminant are selected from the verification results in (2), thereby selecting a combination of amino acid concentration data contained in the colorectal cancer state information used in preparing of the candidate multivariate discriminant, and (4) based on verification results accumulated by executing (1), (2) and (3) repeatedly, the candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a colorectal cancer state (specifically a multivariate discriminant correlating significantly with the state (progress of a morbid state) of colorectal cancer (early colorectal cancer) (more specifically a multivariate discriminant useful for discrimination of the 2 groups of colorectal cancer and colorectal cancer-free)).

According to the colorectal cancer-evaluating system of the present invention, the information communication terminal apparatus first transmits amino acid concentration data of a subject to be evaluated to the colorectal cancer-evaluating apparatus. The colorectal cancer-evaluating apparatus receives the amino acid concentration data of the subject transmitted from the information communication terminal apparatus, calculates a discriminant value that is a value of a multivariate discriminant based on both the concentration value of at least one of Arg, Cys, Orn, Trp, Glu, ABA, Val, Phe, Leu, Gln, Ile and His contained in the received amino acid concentration data of the subject and the multivariate discriminant with amino acid concentration as explanatory variable stored in the memory unit, where at least one of Arg, Cys, Orn, Trp, Glu, ABA, Val, Phe, Leu, Gln, Ile and His is contained as an explanatory variable, and evaluates the colorectal cancer state in the subject based on the calculated discriminant value, and transmits the evaluation result of the subject to the information communication terminal apparatus. Then, the information communication terminal apparatus receives the evaluation result of the subject concerning the colorectal cancer state transmitted from the colorectal cancer-evaluating apparatus. Thus, a discriminant value obtained in a multivariate discriminant correlated significantly with a colorectal cancer state can be utilized to bring about an effect of enabling accurate evaluation of a colorectal cancer state.

According to the colorectal cancer-evaluating system of the present invention, between colorectal cancer and colorectal cancer-free in the subject is discriminated based on the calculated discriminant value. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

According to the colorectal cancer-evaluating system of the present invention, the multivariate discriminant is expressed by one fractional expression or the sum of a plurality of the fractional expressions and contains at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating system of the present invention, the multivariate discriminant is formula 1 or 2:

$$a_1 \times \text{Orn}/(\text{Trp}+\text{His}) + b_1 \times (\text{ABA}+\text{Ile})/\text{Leu} + c_1 \quad \text{(formula 1)}$$

$$a_2 \times \text{Gln}/\text{Val} + b_2 \times \text{Cit}/\text{ABA} + c_2 \times \text{Thr}/\text{Glu} + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating system of the present invention, the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating system of the present invention, the multivariate discriminant is the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free.

According to the colorectal cancer-evaluating system of the present invention, a multivariate discriminant stored in a memory unit is prepared based on the colorectal cancer state information containing the amino acid concentration data and colorectal cancer state index data on an index for indicating the colorectal cancer state, stored in the memory unit. Specifically, (1) a candidate multivariate discriminant is prepared from the colorectal cancer state information, according to a predetermined discriminant-preparing method, (2) the prepared candidate multivariate discriminant is verified based on a predetermined verification method, (3) based on a predetermined explanatory variable-selecting method, explanatory variables in the candidate multivariate discriminant are selected from the verification results in (2), thereby selecting a combination of amino acid concentration data contained in the colorectal cancer state information used in preparing of the candidate multivariate discriminant, and (4) based on verification results accumulated by executing (1), (2) and (3) repeatedly, the candidate multivariate discriminant used as the multivariate discriminant is selected from a plurality of candidate multivariate discriminants, thereby preparing the multivariate discriminant. There can thereby be brought about an effect of enabling preparation of the multivariate discriminant most appropriate for evaluation of a colorectal cancer state (specifically a multivariate discriminant correlating significantly with the state (progress of a morbid state) of colorectal cancer (early colorectal cancer) (more specifically a multivariate discriminant useful for discrimination of the 2 groups of colorectal cancer and colorectal cancer-free)).

According to the recording medium of the present invention, the colorectal cancer-evaluating program recorded on the recording medium is read and executed by the computer, thereby allowing the computer to execute the colorectal cancer-evaluating program, thus bringing about an effect of obtaining the same effect as in the colorectal cancer-evaluating program.

When colorectal cancer state is evaluated (specifically discrimination between colorectal cancer and colorectal cancer-free is conducted) in the present invention, the concentrations of other metabolites, the protein expression level, the age and sex of the subject or the like may be used in addition to the amino acid concentration. When colorectal cancer state is evaluated (specifically discrimination between colorectal cancer and colorectal cancer-free is conducted) in the present invention, the concentrations of other metabolites, the protein expression level, the age and sex of the subject or the like may be used as explanatory variables in the multivariate discriminant in addition to the amino acid concentration.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of the information stored in the user information file 106a;

FIG. 8 is a chart showing an example of the information stored in the amino acid concentration data file 106b;

FIG. 9 is a chart showing an example of the information stored in the colorectal cancer state information file 106c;

FIG. 10 is a chart showing an example of the information stored in the designated colorectal cancer state information file 106d;

FIG. 11 is a chart showing an example of the information stored in the candidate multivariable discriminant file 106e1;

FIG. 12 is a chart showing an example of the information stored in the verification result file 106e2;

FIG. 13 is a chart showing an example of the information stored in the selected colorectal cancer state information file 106e3;

FIG. 14 is a chart showing an example of the information stored in the multivariable discriminant file 106e4;

FIG. 15 is a chart showing an example of the information stored in the discriminant value file 106f;

FIG. 26 is a chart showing the cutoff value, sensitivity, specificity, positive predictive value, negative predictive value, and correct diagnostic rate in discrimination of 2 groups;

FIG. 27 is a chart showing a list of indices having the same diagnostic performance as that of index formula 1;

FIG. 28 is a chart showing a list of indices having the same diagnostic performance as that of index formula 1;

FIG. 29 is a chart showing a list of indices having the same diagnostic performance as that of index formula 1;

FIG. 30 is a chart showing a list of indices having the same diagnostic performance as that of index formula 1;

FIG. 32 is a chart showing the cutoff value, sensitivity, specificity, positive predictive value, negative predictive value, and correct diagnostic rate in discrimination of 2 groups;

FIG. 33 is a chart showing a list of indices having the same diagnostic performance as that of index formula 2;

FIG. 34 is a chart showing a list of indices having the same diagnostic performance as that of index formula 2;

FIG. 35 is a chart showing a list of indices having the same diagnostic performance as that of index formula 2;

FIG. 36 is a chart showing a list of indices having the same diagnostic performance as that of index formula 2;

FIG. 38 is a chart showing the cutoff value, sensitivity, specificity, positive predictive value, negative predictive value, and correct diagnostic rate in discrimination of 2 groups;

FIG. 39 is a chart showing a list of indices having the same diagnostic performance as that of index formula 3;

FIG. 40 is a chart showing a list of indices having the same diagnostic performance as that of index formula 3;

FIG. 41 is a chart showing a list of indices having the same diagnostic performance as that of index formula 3;

FIG. 42 is a chart showing a list of indices having the same diagnostic performance as that of index formula 3;

FIG. 43 is a graph showing a list of amino acids extracted based on the AUC of the ROC curve;

FIG. 45 is a graph showing the AUC of the ROC curve of amino acid explanatory variables;

FIG. 47 is a chart showing a list of indices having the same diagnostic performance as that of index formula 4;

FIG. 48 is a chart showing a list of indices having the same diagnostic performance as that of index formula 4;

FIG. 50 is a chart showing a list of indices having the same diagnostic performance as that of index formula 5;

FIG. 51 is a chart showing a list of indices having the same diagnostic performance as that of index formula 5;

FIG. 53 is a chart showing a list of indices having the same diagnostic performance as that of index formula 6;

FIG. 54 is a chart showing a list of indices having the same diagnostic performance as that of index formula 6; and FIG. 55 is a graph showing a list of amino acids extracted based on the AUC of the ROC curve.

DETAILED DESCRIPTION OF THE PREFERRED EMBODIMENTS

Hereinafter, an embodiment (first embodiment) of the method of evaluating colorectal cancer of the present invention and an embodiment (second embodiment) of the colorectal cancer-evaluating apparatus, the colorectal cancer-evaluating method, the colorectal cancer-evaluating system, the colorectal cancer-evaluating program and the recording medium of the present invention are described in detail with reference to the drawings. The present invention is not limited to these embodiments.

First Embodiment 1-1. Outline of the Invention

Figure 1:
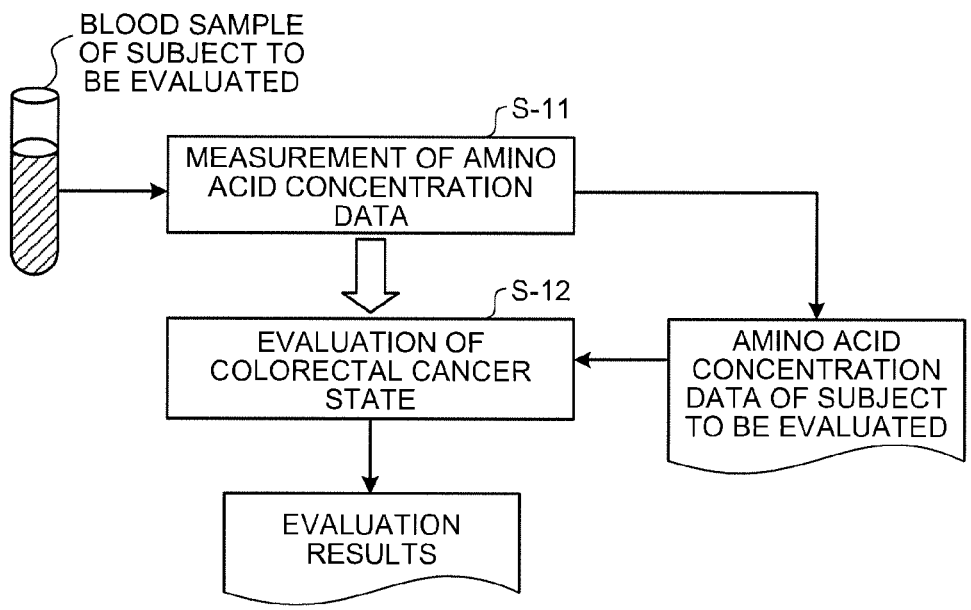
FIG. 1 is a principle configurational diagram showing the basic principle of the present invention.

Here, an outline of the method of evaluating colorectal cancer of the present invention will be described with reference to FIG. 1. FIG. 1 is a principle configurational diagram showing the basic principle of the present invention.

In the present invention, the amino acid concentration data on concentration values of amino acids in blood collected from a subject (for example, an individual such as animal or human) to be evaluated are first measured (step S-11). The concentrations of amino acids in blood were analyzed in the following manner. A blood sample is collected in a heparin-treated tube, and then the blood plasma is separated by centrifugation of the collected blood sample. All blood plasma samples separated were frozen and stored at −70° C. before measurement of amino acid concentration. Before measurement of amino acid concentration, the blood plasma sample was deproteinized by adding sulfosalicylic acid to a concentration of 3%. An amino acid analyzer by high-performance liquid chromatography (HPLC) by using ninhydrin reaction in the post column was used for measurement of amino acid concentration. The unit of amino acid concentration may be for example molar concentration, weight concentration, or these concentrations which are subjected to addition, subtraction, multiplication and division by an arbitrary constant.

In the present invention, the colorectal cancer state in the subject is evaluated based on at least one concentration value of Arg, Cys, Orn, Trp, Glu, ABA, Val, Phe, Leu, Gln, Ile and His contained in the amino acid concentration data of the subject measured in the step S-11 (step S-12).

According to the present invention described above, amino acid concentration data on the concentration value of amino acid in blood collected from the subject is measured, and the colorectal cancer state in the subject is evaluated based on the concentration value of at least one of Arg, Cys, Orn, Trp, Glu, ABA, Val, Phe, Leu, Gln, Ile and His contained in the measured amino acid concentration data of the subject. Thus, the concentrations of the amino acids which among amino acids in blood, are related to a colorectal cancer state can be utilized to bring about an effect of enabling accurate evaluation of a colorectal cancer state.

Before step S-12 is executed, data such as defective and outliers may be removed from the amino acid concentration data of the subject measured in step S-11. Thereby, a colorectal cancer state can be more accurately evaluated.

In step S-12, between colorectal cancer and colorectal cancer-free in the subject may be discriminated based on the concentration value of at least one of Arg, Cys, Orn, Trp, Glu, ABA, Val, Phe, Leu, Gln, Ile and His contained in the amino acid concentration data of the subject measured in step S-11. Specifically, at least one concentration value of Arg, Cys, Orn, Trp, Glu, ABA, Val, Phe, Leu, Gln, Ile and His may be compared with a previously established threshold (cutoff value), thereby discriminating between colorectal cancer and colorectal cancer-free in the subject. Thus, the concentrations of the amino acids which among amino acids in blood, are useful for discriminating between the 2 groups of colorectal cancer and colorectal cancer-free can be utilized to bring about an effect of enabling accurate discrimination between the 2 groups of colorectal cancer and colorectal cancer-free.

In step S-12, a discriminant value that is a value of multivariate discriminant may be calculated based on both the concentration value of at least one of Arg, Cys, Orn, Trp, Glu, ABA, Val, Phe, Leu, Gln, Ile and His contained in the amino acid concentration data of the subject measured in step S-11 and a previously established multivariate discriminant with the concentration of the amino acid as explanatory variable, where at least one of Arg, Cys, Orn, Trp, Glu, ABA, Val, Phe, Leu, Gln, Ile and His is contained as the explanatory variable, and the colorectal cancer state in the subject may be evaluated based on the calculated discriminant value. Thus, a discriminant value obtained in a multivariate discriminant correlated significantly with a colorectal cancer state can be utilized to bring about an effect of enabling accurate evaluation of a colorectal cancer state.

In step S-12, a discriminant value that is a value of multivariate discriminant may be calculated based on both the concentration value of at least one of Arg, Cys, Orn, Trp, Glu, ABA, Val, Phe, Leu, Gln, Ile and His contained in the amino acid concentration data of the subject measured in step S-11 and a previously established multivariate discriminant with the concentration of the amino acid as explanatory variable, where at least one of Arg, Cys, Orn, Trp, Glu, ABA, Val, Phe, Leu, Gln, Ile and His is contained as the explanatory variable, and between colorectal cancer and colorectal cancer-free in the subject may be discriminated based on the calculated discriminant value. Specifically, the discriminant value may be compared with a previously established threshold (cutoff value), thereby discriminating between colorectal cancer and colorectal cancer-free in the subject. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

The multivariate discriminant may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant may be formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in evaluation of a colorectal cancer state, regardless of the unit of amino acid concentration in the amino acid concentration data as input data.

In a fractional expression, the numerator of the fractional expression is expressed by the sum of amino acids A, B, C etc. and the denominator of the fractional expression is expressed by the sum of amino acids a, b, c etc. The fractional expression also includes the sum of fractional expressions α, β, γ etc. (for example, α+β) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each explanatory variable and the value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method (multivariate discriminant-preparing processing described in the second embodiment described later) described in International Publication WO 2006/098192 that is an international application filed by the present applicant. Any multivariate discriminants obtained by this method can be preferably used in evaluation of a colorectal cancer state, regardless of the unit of amino acid concentration in the amino acid concentration data as input data.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination.

The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When colorectal cancer state is evaluated (specifically discrimination between colorectal cancer and colorectal cancer-free is conducted) in the present invention, the concentrations of other metabolites, the protein expression level, the age and sex of the subject or the like may be used in addition to the amino acid concentration. When colorectal cancer state is evaluated (specifically discrimination between colorectal cancer and colorectal cancer-free is conducted) in the present invention, the concentrations of other metabolites, the protein expression level, the age and sex of the subject or the like may be used as explanatory variables in the multivariate discriminant in addition to the amino acid concentration.

Figure 2:
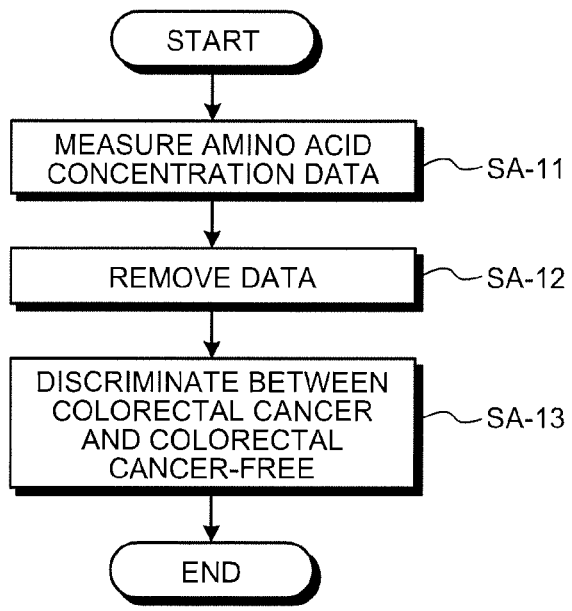
FIG. 2 is a flowchart showing one example of the method of evaluating colorectal cancer according to the first embodiment.

1-2. Method of Evaluating Colorectal Cancer in Accordance with the First Embodiment Herein, the method of evaluating colorectal cancer according to the first embodiment is described with reference to FIG. 2. FIG. 2 is a flowchart showing one example of the method of evaluating colorectal cancer according to the first embodiment.

From blood collected from an individual such as animal or human, amino acid concentration data on the concentration values of amino acids are measured (step SA-11). Measurement of the concentration values of amino acids is conducted by the method described above.

From the amino acid concentration data of the individual measured in step SA-11, data such as defective and outliers are then removed (step SA-12).

Then, at least one concentration value of Arg, Cys, Orn, Trp, Glu, ABA, Val, Phe, Leu, Gln, Ile and His contained in the amino acid concentration data of the individual from which defective and outliers have been removed in step SA-12 is compared with a previously established threshold (cutoff value), thereby discriminating between colorectal cancer and colorectal cancer-free in the individual, or a discriminant value is calculated based on both at least one concentration value of Arg, Cys, Orn, Trp, Glu, ABA, Val, Phe, Leu, Gln, Ile and His contained in the amino acid concentration data of the individual from which defective and outliers have been removed in step SA-12 and a previously established multivariate discriminant containing at least one of Arg, Cys, Orn, Trp, Glu, ABA, Val, Phe, Leu, Gln, Ile and His as explanatory variable, and the calculated discriminant value is compared with a previously established threshold (cutoff value), thereby discriminating between colorectal cancer and colorectal cancer-free in the individual (step SA-13).

1-3. Summary of the First Embodiment and Other Embodiments

In the method of evaluating colorectal cancer as described above in detail, (1) amino acid concentration data are measured from blood collected from the individual, (2) data such as defective and outliers are removed from the measured amino acid concentration data of the individual, and (3) at least one concentration value of Arg, Cys, Orn, Trp, Glu, ABA, Val, Phe, Leu, Gln, Ile and His contained in the amino acid concentration data of the individual from which defective and outliers have been removed is compared with the previously established threshold (cutoff value), thereby discriminating between colorectal cancer and colorectal cancer-free in the individual, or the discriminant value is calculated based on both at least one concentration value of Arg, Cys, Orn, Trp, Glu, ABA, Val, Phe, Leu, Gln, Ile and His contained in the amino acid concentration data of the individual from which detective and outliers have been removed and the previously established multivariate discriminant containing at least one of Arg, Cys, Orn, Trp, Glu, ABA, Val, Phe, Leu, Gln, Ile and His as explanatory variable, and the calculated discriminant value is compared with the previously established threshold (cutoff value), thereby discriminating between colorectal cancer and colorectal cancer-free in the individual. Thus, concentrations of amino acids which among amino acids in blood, are useful for discriminating between the 2 groups of colorectal cancer and colorectal cancer-free or a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

In step SA-13, the multivariate discriminant may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant may be formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in evaluation of a colorectal cancer state, regardless of the unit of amino acid concentration in the amino acid concentration data as input data.

In step SA-13, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method (multivariate discriminant-preparing processing described in the second embodiment described later) described in International Publication WO 2006/098192 that is an international application filed by the present applicant. Any multivariate discriminants obtained by this method can be preferably used in evaluation of a colorectal cancer state, regardless of the unit of amino acid concentration in the amino acid concentration data as input data.

Second Embodiment 2-1. Outline of the Invention

Figure 3:
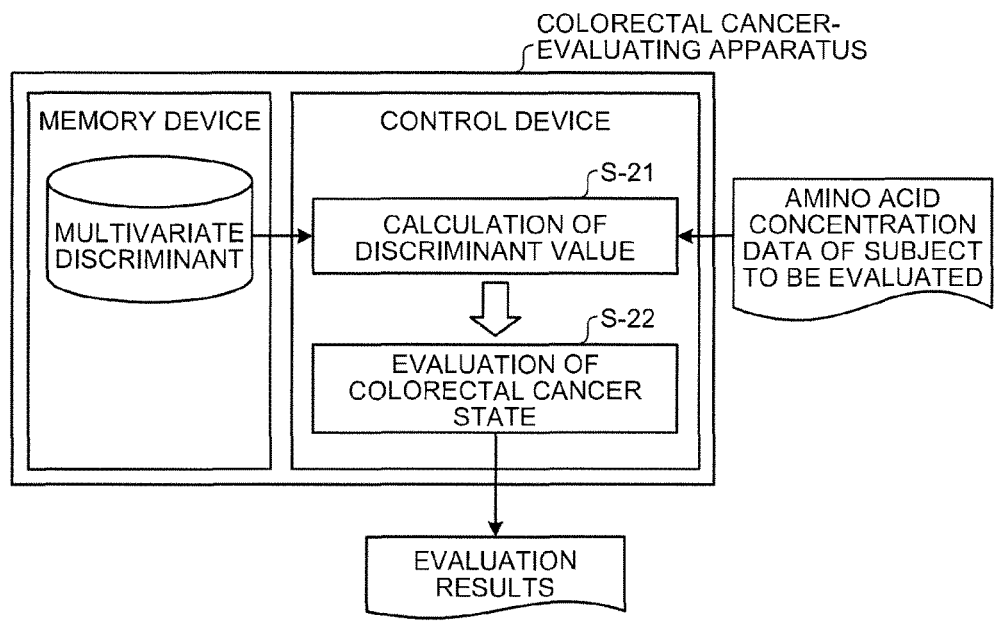
FIG. 3 is a principle configurational diagram showing the basic principle of the present invention.

Herein, an outline of the colorectal cancer-evaluating apparatus, the colorectal cancer-evaluating method, the colorectal cancer-evaluating system, the colorectal cancer-evaluating program and the recording medium of the present invention are described in detail with reference to FIG. 3. FIG. 3 is a principle configurational diagram showing the basic principle of the present invention.

In the present invention, a discriminant value that is a value of a multivalent discriminant is calculated in a control device based on both a concentration value of at least one of Arg, Cys, Orn, Trp, Glu, ABA, Val, Phe, Leu, Gln, Ile and His contained in previously obtained amino acid concentration data of a subject to be evaluated (for example, an individual such as animal or human) and a previously established multivariate discriminant with concentrations of amino acids as explanatory variables stored in a memory device, where at least one of Arg, Cys, Orn, Trp, Glu, ABA, Val, Phe, Leu, Gln, Ile and His is contained as explanatory variables (step S-21).

In the present invention, a colorectal cancer state in the subject is evaluated in the control device based on the discriminant value calculated in step S-21 (step S-22).

According to the present invention described above, the discriminant value that is the value of multivariate discriminant is calculated based on both the concentration value of at least one of Arg, Cys, Orn, Trp, Glu, ABA, Val, Phe, Leu, Gln, Ile and His contained in the previously obtained amino acid concentration data on the concentration value of amino acid in the subject and the multivariate discriminant with the concentration of the amino acid as explanatory variable stored in the memory device, where at least one of Arg, Cys, Orn, Trp, Glu, ABA, Val, Phe, Leu, Gln, Ile and His is contained as the explanatory variable, and the colorectal cancer state in the subject is evaluated based on the calculated discriminant value. Thus, a discriminant value obtained in a multivariate discriminant correlated significantly with a colorectal cancer state can be utilized to bring about an effect of enabling accurate evaluation of a colorectal cancer state.

In step S-22, between colorectal cancer and colorectal cancer-free in the subject may be discriminated based on the discriminant value calculated in step S-21. Specifically, the discriminant value may be compared with a previously established threshold (cutoff value), thereby discriminating between colorectal cancer and colorectal cancer-free in the subject. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

The multivariate discriminant may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant may be formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in evaluation of a colorectal cancer state, regardless of the unit of amino acid concentration in the amino acid concentration data as input data.

In a fractional expression, the numerator of the fractional expression is expressed by the sum of amino acids A, B, C etc. and the denominator of the fractional expression is expressed by the sum of amino acids a, b, c etc. The fractional expression also includes the sum of fractional expressions $\alpha$, $\beta$, $\gamma$ etc. (for example, $\alpha+\beta$) having such constitution. The fractional expression also includes divided fractional expressions. Amino acids used in the numerator or denominator may have suitable coefficients respectively. The amino acids used in the numerator or denominator may appear repeatedly. Each fractional expression may have a suitable coefficient. The value of a coefficient for each explanatory variable and the value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method (multivariate discriminant-preparing processing described later) described in International Publication WO 2006/098192 that is an international application filed by the present applicant. Any multivariate discriminants obtained by this method can be preferably used in evaluation of a colorectal cancer state, regardless of the unit of amino acid concentration in the amino acid concentration data as input data.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

When colorectal cancer state is evaluated (specifically discrimination between colorectal cancer and colorectal cancer-free is conducted) in the present invention, the concentrations of other metabolites, the protein expression level, the age and sex of the subject or the like may be used in addition to the amino acid concentration. When colorectal cancer state is evaluated (specifically discrimination between colorectal cancer and colorectal cancer-free is conducted) in the present invention, the concentrations of other metabolites, the protein expression level, the age and sex of the subject or the like may be used as explanatory variables in the multivariate discriminant in addition to the amino acid concentration.

Here, the summary of the multivariate discriminant-preparing processing (steps 1 to 4) is described in detail.

First, from colorectal cancer state information including amino acid concentration data and colorectal cancer state index data concerning an index showing a colorectal cancer state stored in a memory device, a candidate multivariate discriminant (e.g., $y=a_1x_1+a_2x_2+ \ldots +a_nx_n$, y: colorectal cancer state index data, $x_i$: amino acid concentration data, $a_i$: constant, i=1, 2, ..., n) that is a candidate for a multivariate discriminant is prepared by a predetermined discriminant-preparing method at the control device (step 1). Data containing defective and outliers may be removed in advance from the colorectal cancer state information.

In step 1, a plurality of candidate multivariate discriminants may be prepared from the colorectal cancer state information by using a plurality of different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of candidate multivariate discriminant groups may be prepared simultaneously and concurrently by using a plurality of different algorithms with the colorectal cancer state information which is multivariate data composed of the amino acid concentration data and the colorectal cancer state index data obtained by analyzing blood samples from a large number of healthy subjects and colorectal cancer patients. For example, two different candidate multivariate discriminants may be formed by performing discriminant analysis and logistic regression analysis simultaneously with different algorithms. Alternatively, a candidate multivariate discriminant may be formed by converting the colorectal cancer state information with the candidate multivariate discriminant prepared by performing principal component analysis and then performing discriminant analysis of the converted colorectal cancer state information. In this way, it is possible to finally prepare the multivariate discriminant suitable for diagnostic condition.

The candidate multivariate discriminant prepared by principal component analysis is a linear expression consisting of amino acid explanatory variables maximizing the variance of all amino acid concentration data. The candidate multivariate discriminant prepared by discriminant analysis is a high-powered expression (including exponential and logarithmic expressions) consisting of amino acid explanatory variables minimizing the ratio of the sum of the variances in respective groups to the variance of all amino acid concentration data. The candidate multivariate discriminant prepared by using support vector machine is a high-powered expression (including kernel function) consisting of amino acid explanatory variables maximizing the boundary between groups. The candidate multivariate discriminant prepared by multiple regression analysis is a high-powered expression consisting of amino acid explanatory variables minimizing the sum of the distances from all amino acid concentration data. The candidate multivariate discriminant prepared by logistic regression analysis is a fraction expression having, as a component, the natural logarithm having a linear expression consisting of amino acid explanatory variables maximizing the likelihood as the exponent. The k-means method is a method of searching k pieces of neighboring amino acid concentration data in various groups designating the group containing the greatest number of the neighboring points as its data-belonging group, and selecting the amino acid explanatory variable that makes the group to which input amino acid concentration data belong agree well with the designated group. The cluster analysis is a method of clustering (grouping) the points closest in entire amino acid concentration data. The decision tree is a method of ordering amino acid explanatory variables and predicting the group of amino acid concentration data from the pattern possibly held by the higher-ordered amino acid explanatory variable.

Returning to the description of the multivariate discriminant-preparing processing, the candidate multivariate discriminant prepared in step 1 is verified (mutually verified) in the control device by a particular verification method (step 2). Verification of the candidate multivariate discriminant is performed on each other to each candidate multivariate discriminant prepared in step 1.

In step 2, at least one of the discrimination rate, sensitivity, specificity, information criterion, and the like of the candidate multivariate discriminant may be verified by at least one of the bootstrap method, holdout method, leave-one-out method, and the like. In this way, it is possible to prepare the candidate multivariate discriminant higher in predictability or reliability, by taking the colorectal cancer state information and the diagnostic condition into consideration.

The discrimination rate is the rate of the data wherein the colorectal cancer state evaluated according to the present invention is correct in all input data. The sensitivity is the rate of the colorectal cancer states judged correct according to the present invention in the colorectal cancer states declared colorectal cancer in the input data. The specificity is the rate of the colorectal cancer states judged correct according to the present invention in the colorectal cancer states described healthy in the input data. The information criterion is the sum of the number of the amino acid explanatory variables in the candidate multivariate discriminant prepared in step 1 and the difference in number between the colorectal cancer states evaluated according to the present invention and those described in input data. The predictability is the average of the discrimination rate, sensitivity, or specificity obtained by repeating verification of the candidate multivariate discriminant. Alternatively, the reliability is the variance of the discrimination rate, sensitivity, or specificity obtained by repeating verification of the candidate multivariate discriminant.

Returning to the description of the multivariate discriminant-preparing processing, a combination of amino acid concentration data contained in the colorectal cancer state information used in preparing the candidate multivariate discriminant is selected by selecting an explanatory variable of the candidate multivariate discriminant from the verification result in step 2 according to a predetermined explanatory variable selection method in the control device (step 3). The selection of amino acid explanatory variable is performed on each candidate multivariate discriminant prepared in step 1. In this way, it is possible to select the amino acid explanatory variable of the candidate multivariate discriminant properly. The step 1 is executed once again by using the colorectal cancer state information including the amino acid concentration data selected in step 3.

From the verification result in step 2, an amino acid explanatory variable of the candidate multivariate discriminant may be selected in step 3, based on at least one of stepwise method, best path method, local search method, and genetic algorithm.

The best path method is a method of selecting an amino acid explanatory variable by optimizing the evaluation index of the candidate multivariate discriminant while eliminating the explanatory variables contained in the candidate multivariate discriminant one by one.

Returning to the description of the multivariate discriminant-preparing processing, the steps 1, 2 and 3 are repeatedly performed in the control device, and based on verification results thus accumulated, a candidate multivariate discriminant used as the multivariate discriminant is selected from a plurality of candidate multivariate discriminants, thereby preparing the multivariate discriminant (step 4). In selection of the candidate multivariate discriminants, there are cases where the optimum multivariate discriminant is selected from candidate multivariate discriminants prepared in the same method or the optimum multivariate discriminant is selected from all candidate multivariate discriminants.

As described above, processing for preparation of candidate multivariate discriminants, verification of the candidate multivariate discriminants, and selection of explanatory variables in the candidate multivariate discriminants are performed based on the colorectal cancer state information in a series of operations in a systematized manner in the multivariate discriminant-preparing processing, whereby the optimum multivariate discriminant for evaluation of colorectal cancer state can be prepared.

2-2. System Configuration

Hereinafter, the configuration of the colorectal cancer-evaluating system according to the second embodiment (hereinafter referred to sometimes as the present system) will be described with reference to FIGS. 4 to 20. This system is merely one example, and the present invention is not limited thereto.

Figure 4:
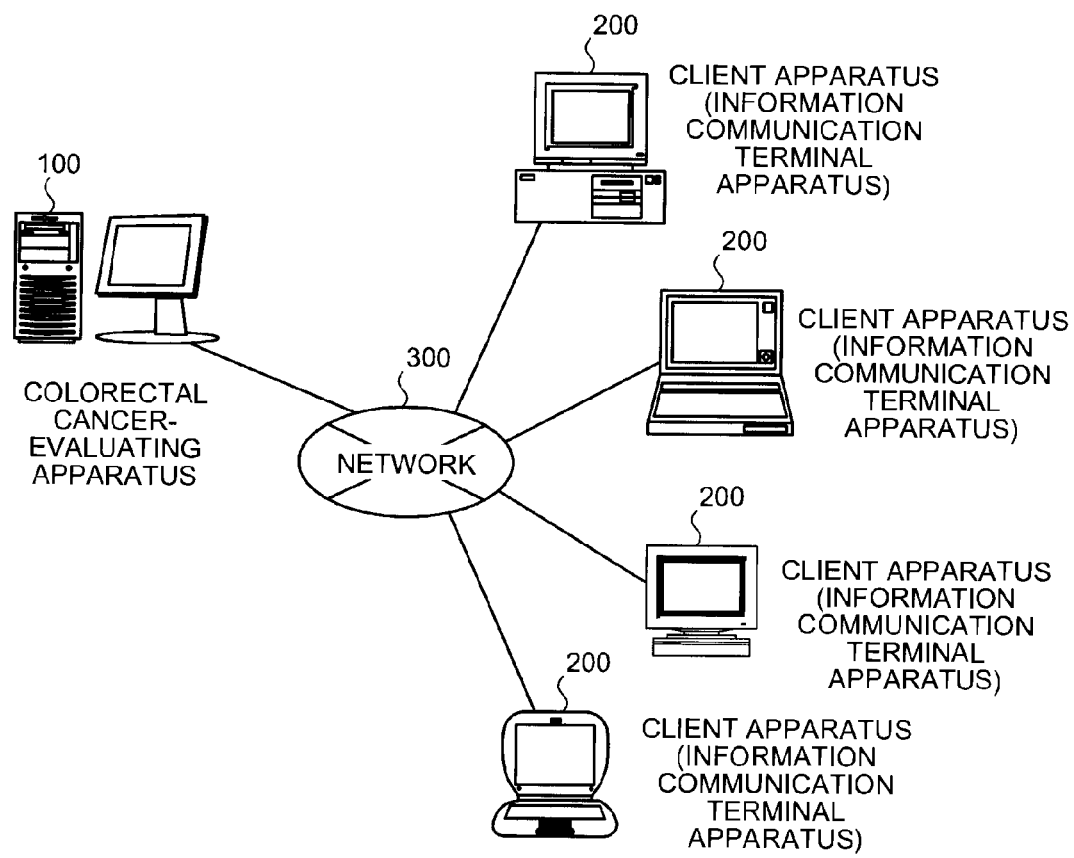
FIG. 4 is a diagram showing an example of the entire configuration of the present system.
Figure 5:
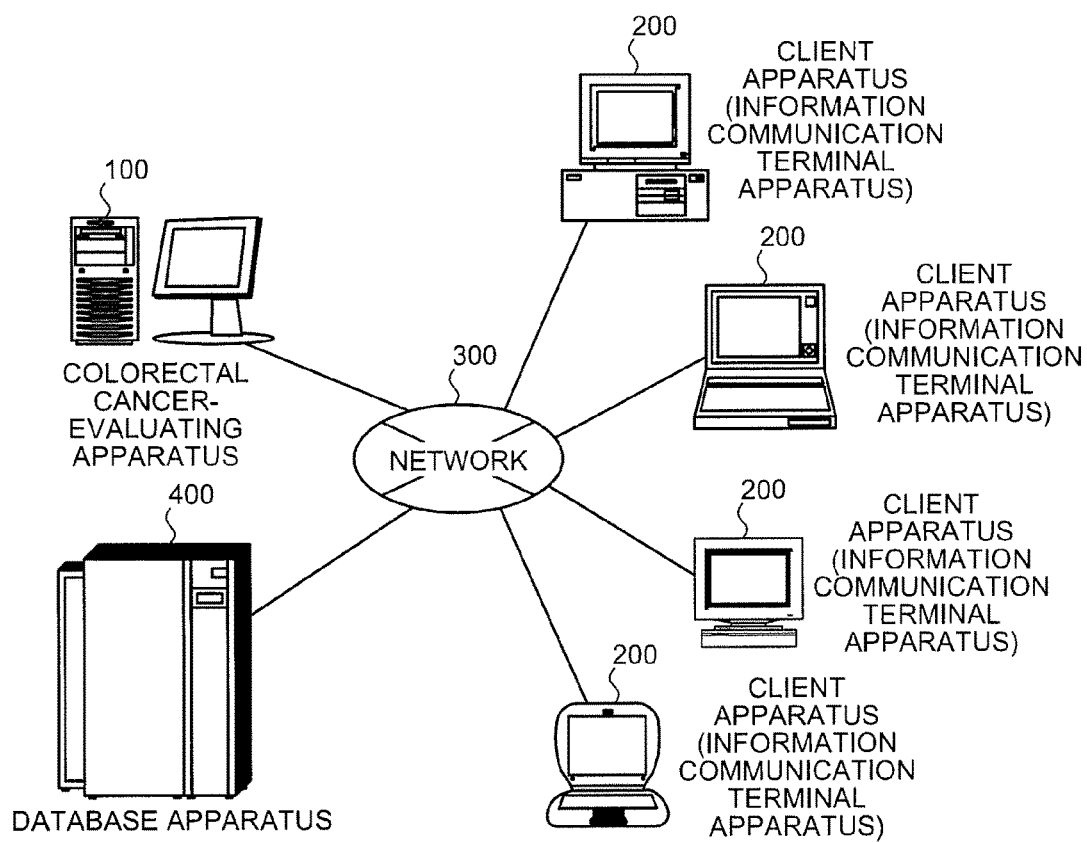
FIG. 5 is a diagram showing another example of the entire configuration of the present system.

First, the entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which a colorectal cancer-evaluating apparatus 100 that evaluates a colorectal cancer state in a subject to be evaluated, and a client apparatus 200 (corresponding to the information communication terminal apparatus of the present invention) which provides the amino acid concentration data on the concentration values of amino acids in the subject, are communicatively connected to each other via a network 300.

In the present system as shown in FIG. 5, in addition to the colorectal cancer-evaluating apparatus 100 and the client apparatus 200, a database apparatus 400 storing, for example, the colorectal cancer state information used in preparing a multivariate discriminant and the multivariate discriminant used in evaluating the colorectal cancer state in the colorectal cancer-evaluating apparatus 100, may be communicatively connected via the network 300. In this configuration, the information on a colorectal cancer state etc. are provided via the network 300 from the colorectal cancer-evaluating apparatus 100 to the client apparatuses 200 and the database apparatus 400, or from the client apparatuses 200 and the database apparatus 400 to the colorectal cancer-evaluating apparatus 100. The "information on a colorectal cancer state" is information on the measured values of particular items of the colorectal cancer state of organisms including human. The information on a colorectal cancer state is generated in the colorectal cancer-evaluating apparatus 100, client apparatus 200, and other apparatuses (e.g., various measuring apparatuses) and stored mainly in the database apparatus 400.

Figure 6:
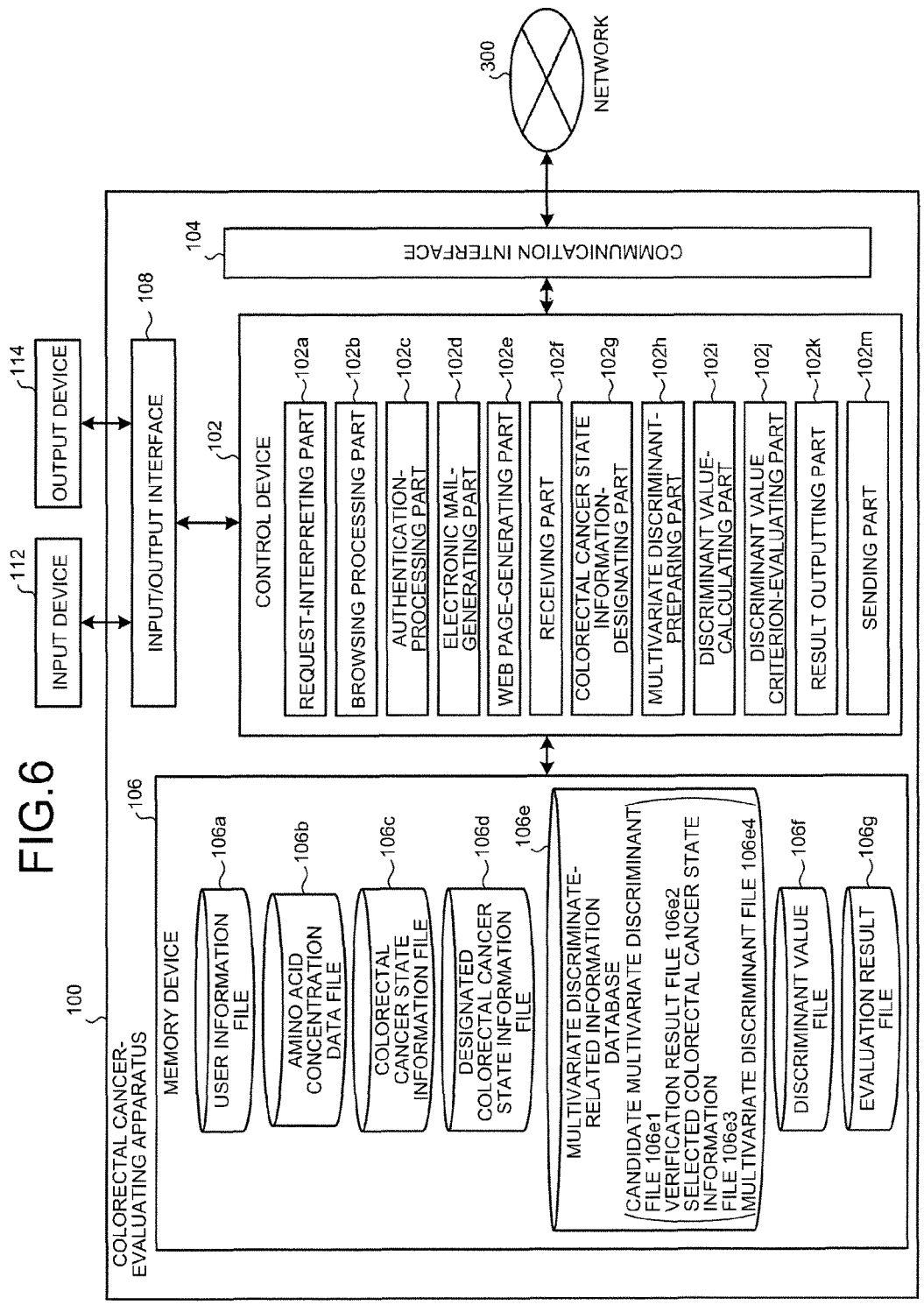
FIG. 6 is a block diagram showing an example of the configuration of the colorectal cancer-evaluating apparatus 100 in the present system.

Now, the configuration of the colorectal cancer-evaluating apparatus 100 in the present system will be described with reference to FIGS. 6 to 18. FIG. 6 is a block diagram showing an example of the configuration of the colorectal cancer-evaluating apparatus 100 in the present system, showing conceptually only the region relevant to the present invention.

The colorectal cancer-evaluating apparatus 100 includes a control device 102, such as CPU (Central Processing Unit), that integrally controls the colorectal cancer-evaluating apparatus 100, a communication interface 104 that connects the colorectal cancer-evaluating apparatus 100 to the network 300 communicatively via communication apparatuses such as router and a wired or wireless communication line such as private line, a memory device 106 that stores various databases, tables, files and others, and an input/output interface 108 connected to an input device 112 and an output device 114, that are connected to each other communicatively via any communication channel. The colorectal cancer-evaluating apparatus 100 may be present together with various analyzers (e.g., amino acid analyzer) in a same housing. Typical configuration of disintegration/integration of the colorectal cancer-evaluating apparatus 100 is not limited to that shown in the figure, and all or a part of it may be disintegrated or integrated functionally or physically in any unit, for example, according to various loads applied.

For example, a part of the processing may be performed via a CGI (Common Gateway Interface).

The memory device 106 is a storage means, and examples thereof include memory apparatuses such as RAM (Random Access Memory) and ROM (Read Only Memory), fixed disk drives such as hard disk, flexible disk, optical disk, and the like. The memory device 106 stores computer programs giving instructions to CPU for various processing, together with OS (Operating System). As shown in the figure, the memory device 106 stores a user information file 106a, an amino acid concentration data file 106b, a colorectal cancer state information file 106c, a designated colorectal cancer state information file 106d, a multivariate discriminant-related information database 106e, a discriminant value file 106f and an evaluation result file 106g.

The user information file 106a stores a user information on users. FIG. 7 is a chart showing an example of the information stored in the user information file 106a. As shown in FIG. 7, the information stored in the user information file 106a includes user ID (identification) for identifying the user uniquely, user password for authentication of the user, user name, organization ID for uniquely identifying the organization of the user, department ID for uniquely identifying the department of the user organization, department name, and electronic mail address of the user that are correlated to one another.

Returning to FIG. 6, the amino acid concentration data file 106b stores amino acid concentration data on amino acid concentration values. FIG. 8 is a chart showing an example of the information stored in the amino acid concentration data file 106b. As shown in FIG. 8, the information stored in the amino acid concentration data file 106b includes individual number for uniquely identifying an individual (sample) as a subject to be evaluated and amino acid concentration data that are correlated to one another. In FIG. 8, the amino acid concentration data are assumed to be numerical values, i.e., on continuous scale, but the amino acid concentration data may be expressed on nominal scale or ordinal scale. In the case of nominal or ordinal scale, any number may be allocated to each state for analysis. The amino acid concentration data may be combined with other biological information (e.g., sex difference, age, smoking, digitalized electrocardiogram waveform, enzyme concentration, gene expression level, and the concentrations of metabolites other than amino acids).

Returning to FIG. 6, the colorectal cancer state information file 106c stores the colorectal cancer state information used in preparing a multivariate discriminant. FIG. 9 is a chart showing an example of the information stored in the colorectal cancer state information file 106c. As shown in FIG. 9, the information stored in the colorectal cancer state information file 106c includes individual (sample) number, colorectal cancer state index data (T) corresponding to the colorectal cancer state index (index $T_1$, index $T_2$, index $T_3$ . . . ), and amino acid concentration data that are correlated to one another. In FIG. 9, the colorectal cancer state index data and the amino acid concentration data are assumed to be numerical values, i.e., on continuous scale, but the colorectal cancer state index data and the amino acid concentration data may be expressed on nominal scale or ordinal scale. In the case of nominal or ordinal scale, any number may be allocated to each state for analysis. The colorectal cancer state index data is a single known state index serving as a marker of colorectal cancer state, and numerical data may be used.

Returning to FIG. 6, the designated colorectal cancer state information file 106d stores the colorectal cancer state information designated in the colorectal cancer state information-designating part 102g described below. FIG. 10 is a chart showing an example of the information stored in the designated colorectal cancer state information file 106d. As shown in FIG. 10, the information stored in the designated colorectal cancer state information file 106d includes individual number, designated colorectal cancer state index data, and designated amino acid concentration data that are correlated to one another.

Returning to FIG. 6, the multivariate discriminant-related information database 106e is composed of a candidate multivariate discriminant file 106e1 storing the candidate multivariate discriminant prepared in the candidate multivariate discriminant-preparing part 102h1 described below; a verification result file 106e2 storing the verification results in the candidate multivariate discriminant-verifying part 102h2 described below; a selected colorectal cancer state information file 106e3 storing the colorectal cancer state information containing the combination of amino acid concentration data selected in the explanatory variable-selecting part 102h3 described below; and a multivariate discriminant file 106e4 storing the multivariate discriminant prepared in the multivariate discriminant-preparing part 102h described below.

The candidate multivariate discriminant file 106e1 stores the candidate multivariate discriminant prepared in the candidate multivariate discriminant-preparing part 102h1 described below. FIG. 11 is a chart showing an example of the information stored in the candidate multivariate discriminant file 106e1. As shown in FIG. 11, the information stored in the candidate multivariate discriminant file 106e1 includes rank, and candidate multivariate discriminant (e.g., $F_1$ (Gly, Leu, Phe, . . . ), $F_2$ (Gly, Leu, Phe, . . . ), or $F_3$ (Gly, Leu, Phe, . . . ) in FIG. 11) that are correlated to each other.

Returning to FIG. 6, the verification result file 106e2 stores the verification results verified in the candidate multivariate discriminant-verifying part 102h2 described below. FIG. 12 is a chart showing an example of the information stored in the verification result file 106e2. As shown in FIG. 12, the information stored in the verification result file 106e2 includes rank, candidate multivariate discriminant (e.g., $F_k$ (Gly, Leu, Phe, . . . ), $F_m$ (Gly, Leu, Phe, . . . ), $F_l$ (Gly, Leu, Phe, . . . ) in FIG. 12), and the verification results of each candidate multivariate discriminant (e.g., evaluation value of each candidate multivariate discriminant) that are correlated to one another.

Returning to FIG. 6, the selected colorectal cancer state information file 106e3 stores the colorectal cancer state information including the combination of amino acid concentration data corresponding to the explanatory variable selected in the explanatory variable-selecting part 102$h$3 described below. FIG. 13 is a chart showing an example of the information stored in the selected colorectal cancer state information file 106$e$3. As shown in FIG. 13, the information stored in the selected colorectal cancer state information file 106$e$3 includes individual number, the colorectal cancer state index data designated in the colorectal cancer state information-designating part 102$g$ described below, and the amino acid concentration data selected in the explanatory variable-selecting part 102$h$3 described below that are correlated to one another.

Returning to FIG. 6, the multivariate discriminant file 106$e$4 stores the multivariate discriminant prepared in the multivariate discriminant-preparing part 102$h$ described below. FIG. 14 is a chart showing an example of the information stored in the multivariate discriminant file 106$e$4. As shown in FIG. 14, the information stored in the multivariate discriminant file 106$e$4 includes rank, multivariate discriminant (e.g., $F_p$ (Phe, ... ), $F_p$ (Gly, Leu, Phe), $F_k$ (Gly, Leu, Phe, ... ) in FIG. 14), a threshold corresponding to each discriminant-preparing method, and verification results of each multivariate discriminant (e.g., evaluation value of each multivariate discriminant) that are correlated to one another.

Returning to FIG. 6, the discriminant value file 106$f$ stores the discriminant value calculated in the discriminant value-calculating part 102$i$ described below. FIG. 15 is a chart showing an example of the information stored in the discriminant value file 106$f$. As shown in FIG. 15, the information stored in the discriminant value file 106$f$ includes individual number for uniquely identifying an individual (sample) as a subject to be evaluated, rank (number for uniquely identifying the multivariate discriminant), and discriminant value that are correlated to one another.

Figures 16, 17:
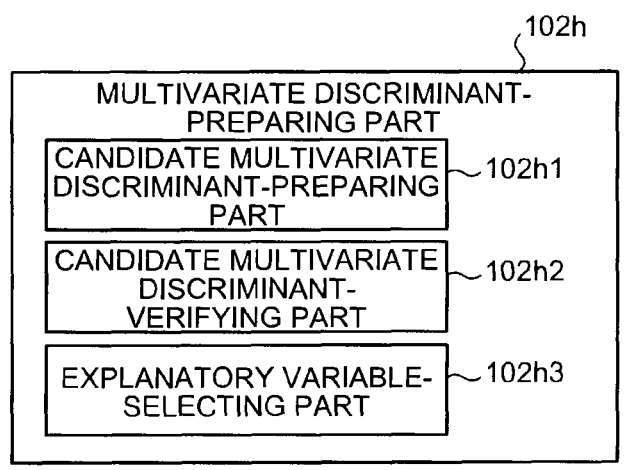
FIG. 16 is a chart showing an example of the information stored in the evaluation result file 106g.
FIG. 17 is a block diagram showing the configuration of the multivariable discriminant-preparing part 102h.

Returning to FIG. 6, the evaluation result file 106$g$ stores the evaluation results obtained in the discriminant value criterion-evaluating part 102$j$ described below (specifically the discrimination results obtained in the discriminant value criterion-discriminating part 102$j$1). FIG. 16 is a chart showing an example of the information stored in the evaluation result file 106$g$. The information stored in the evaluation result file 106$g$ includes individual number for uniquely identifying an individual (sample) as a subject to be evaluated, previously obtained amino acid concentration data on a subject to be evaluated, discriminant value calculated in a multivariate discriminant, and evaluation results on a colorectal cancer state (specifically, discrimination results as to discrimination between colorectal cancer and colorectal cancer-free) that are correlated to one another.

Returning to FIG. 6, the memory device 106 stores various Web data, CGI programs, and others for providing the client apparatuses 200 with web site information as information other than the information described above. The Web data include various data for displaying the Web page described below and others, and the data are generated as, for example, a HTML (HyperText Markup Language) or XML (Extensible Markup Language) text file. Other temporary files such as files for the components for generation of Web data and for operation, and others are also stored in the memory device 106. In addition, it may store as needed sound files in the WAVE or AIFF (Audio Interchange File Format) format for transmission to the client apparatuses 200 and image files of still image or motion picture in the JPEG (Joint Photographic Experts Group) or MPEG2 (Moving Picture Experts Group phase 2) format.

The communication interface 104 allows communication between the colorectal cancer-evaluating apparatus 100 and the network 300 (or communication apparatus such as router). Thus, the communication interface 104 has a function to communicate data via a communication line with other terminals.

The input/output interface 108 is connected to the input device 112 and the output device 114. A monitor (including home television), a speaker, or a printer may be used as the output device 114 (hereinafter, the output device 114 may be described as monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs information processing according to these programs. As shown in the figure, the control device 102 includes mainly a request-interpreting part 102$a$, a browsing processing part 102$b$, an authentication-processing part 102$c$, an electronic mail-generating part 102$d$, a Web page-generating part 102$e$, a receiving part 102$f$, a colorectal cancer state information-designating part 102$g$, a multivariate discriminant-preparing part 102$h$, a discriminant value-calculating part 102$i$, a discriminant value criterion-evaluating part 102$j$, a result outputting part 102$k$ and a sending part 102$m$. The control device 102 performs data processing such as removal of data including defective or many outliers and of explanatory variables for the defective value-including data in the colorectal cancer state information transmitted from the database apparatus 400 and in the amino acid concentration data transmitted from the client apparatus 200.

The request-interpreting part 102$a$ interprets the request from the client apparatus 200 or the database apparatus 400 and sends the request to other parts in the control device 102 according to the analytical result. Upon receiving browsing request for various screens from the client apparatus 200, the browsing processing part 102$b$ generates and transmits the web data for these screens. Upon receiving authentication request from the client apparatus 200 or the database apparatus 400, the authentication-processing part 102$c$ performs authentication. The electronic mail-generating part 102$d$ generates an electronic mail including various kinds of information. The Web page-generating part 102$e$ generates a Web page for a user to browse with the client apparatus 200.

The receiving part 102$f$ receives, via the network 300, the information (specifically, the amino acid concentration data, colorectal cancer state information, multivariate discriminant etc.) transmitted from the client apparatus 200 and the database apparatus 400. The colorectal cancer state information-designating part 102$g$ designates the objective colorectal cancer state index data and amino acid concentration data in preparing the multivariate discriminant.

The multivariate discriminant-preparing part 102$h$ generates a multivariate discriminant based on the colorectal cancer state information received in the receiving part 102$f$ and the colorectal cancer state information designated in the colorectal cancer state information-designating part 102$g$. Specifically, the multivariate discriminant-preparing part 102$h$ generates a multivariate discriminant by selecting a candidate multivariate discriminant to be used as the multivariate discriminant from a plurality of candidate multivariate discriminants, according to the verification results accumulated by repeating the processings in the candidate multivariate discriminant-preparing part 102$h$1, the candidate multivariate discriminant-verifying part 102h2 and the explanatory variable-selecting part 102h3 from the colorectal cancer state information.

If a previously generated multivariate discriminant is stored in a predetermined region of the memory device 106, the multivariate discriminant-preparing part 102h may generate a multivariate discriminant by selecting a desired multivariate discriminant out of the memory device 106. Alternatively, the multivariate discriminant-preparing part 102h may generate the multivariate discriminant by selecting and downloading a desired multivariate discriminant from the multivariate discriminants previously stored in another computer apparatus (e.g., the database apparatus 400).

Hereinafter, the configuration of the multivariate discriminant-preparing part 102h will be described with reference to FIG. 17. FIG. 17 is a block diagram showing the configuration of the multivariate discriminant-preparing part 102h, and only a part in the configuration related to the present invention is shown conceptually. The multivariate discriminant-preparing part 102h has a candidate multivariate discriminant-preparing part 102h1, a candidate multivariate discriminant-verifying part 102h2, and an explanatory variable-selecting part 102h3, additionally. The candidate multivariate discriminant-preparing part 102h1 generates a candidate multivariate discriminant that is a candidate of the multivariate discriminant from the colorectal cancer state information according to a predetermined discriminant-preparing method. Specifically, the candidate multivariate discriminant-preparing part 102h1 may generate a plurality of candidate multivariate discriminants from the colorectal cancer state information, by using a plurality of different discriminant-preparing methods. The candidate multivariate discriminant-verifying part 102h2 verifies the candidate multivariate discriminants prepared in the candidate multivariate discriminant-preparing part 102h1 according to a particular verification method. Specifically, the candidate multivariate discriminant-verifying part 102h2 may verify at least one of the discrimination rate, sensitivity, specificity, and information criterion of the candidate multivariate discriminants according to at least one of bootstrap method, holdout method, and leave-one-out method. The explanatory variable-selecting part 102h3 selects the combination of the amino acid concentration data contained in the colorectal cancer state information to be used in preparing the candidate multivariate discriminant, by selecting an explanatory variable of the candidate multivariate discriminant from the verification results in the candidate multivariate discriminant-verifying part 102h2 according to a particular explanatory variable selection method. The explanatory variable-selecting part 102h3 may select the explanatory variable of the candidate multivariate discriminant from the verification results according to at least one of stepwise method, best path method, local search method, and genetic algorithm.

Returning to FIG. 6, the discriminant value-calculating part 102i calculates a discriminant value that is the value of the multivariate discriminant, based on at least one concentration value of Arg, Cys, Orn, Trp, Glu, ABA, Val, Phe, Leu, Gln, Ile and His contained in the amino acid concentration data of the subject to be evaluated received in the receiving part 102f and the multivariate discriminant containing at least one of Arg, Cys, Orn, Trp, Glu, ABA, Val, Phe, Leu, Gln, Ile and His as explanatory variable prepared in the multivariate discriminant-preparing part 102h.

The multivariate discriminant may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant may be formula 1 or 2:

$$a_1 \times Orn/(Trp+His) + b_1 \times (ABA+Ile)/Leu + c_1 \quad \text{(formula 1)}$$

$$a_2 \times Gln/Val + b_2 \times Cit/ABA + c_2 \times Thr/Glu + d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

The multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

Figure 18:
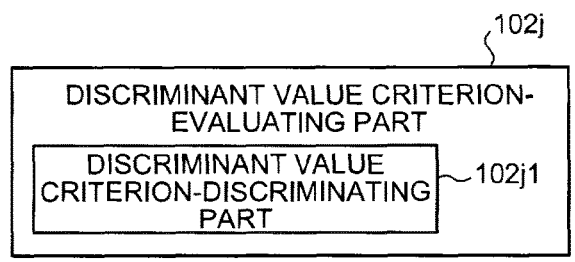
FIG. 18 is a block diagram showing the configuration of the discriminant criterion-evaluating part 102j.

The discriminant value criterion-evaluating part 102j evaluates the colorectal cancer state in the subject to be evaluated, based on the discriminant value calculated in the discriminant value-calculating part 102i. The discriminant value criterion-evaluating part 102j further includes a discriminant value criterion-discriminating part 102j1. Now, the configuration of the discriminant value criterion-evaluating part 102j will be described with reference to FIG. 18. FIG. 18 is a block diagram showing the configuration of the discriminant value criterion-evaluating part 102j, and only a part in the configuration related to the present invention is shown conceptually.

Based on the discriminant value, the discriminant value criterion-discriminating part 102j1 discriminates between colorectal cancer and colorectal cancer-free in the subject to be evaluated. Specifically, the discriminant value criterion-discriminating part 102j1 compares the discriminant value with a predetermined threshold value (cutoff value), thereby discriminating between colorectal cancer and colorectal cancer-free in the subject to be evaluated.

Returning to FIG. 6, the result outputting part 102k outputs, into the output device 114, the processing results in each processing part in the control device 102 (the evaluation results in the discriminant value criterion-evaluating part 102j (specifically the discrimination results in the discriminant value criterion-discriminating part 102j1)) etc.

The sending part 102m sends the evaluation results to the client apparatus 200 that is the sender of the amino acid concentration data of the subject to be evaluated or sends the multivariate discriminant prepared in the colorectal cancer-evaluating apparatus 100, and the evaluation results, to the database apparatus 400.

Figure 19:
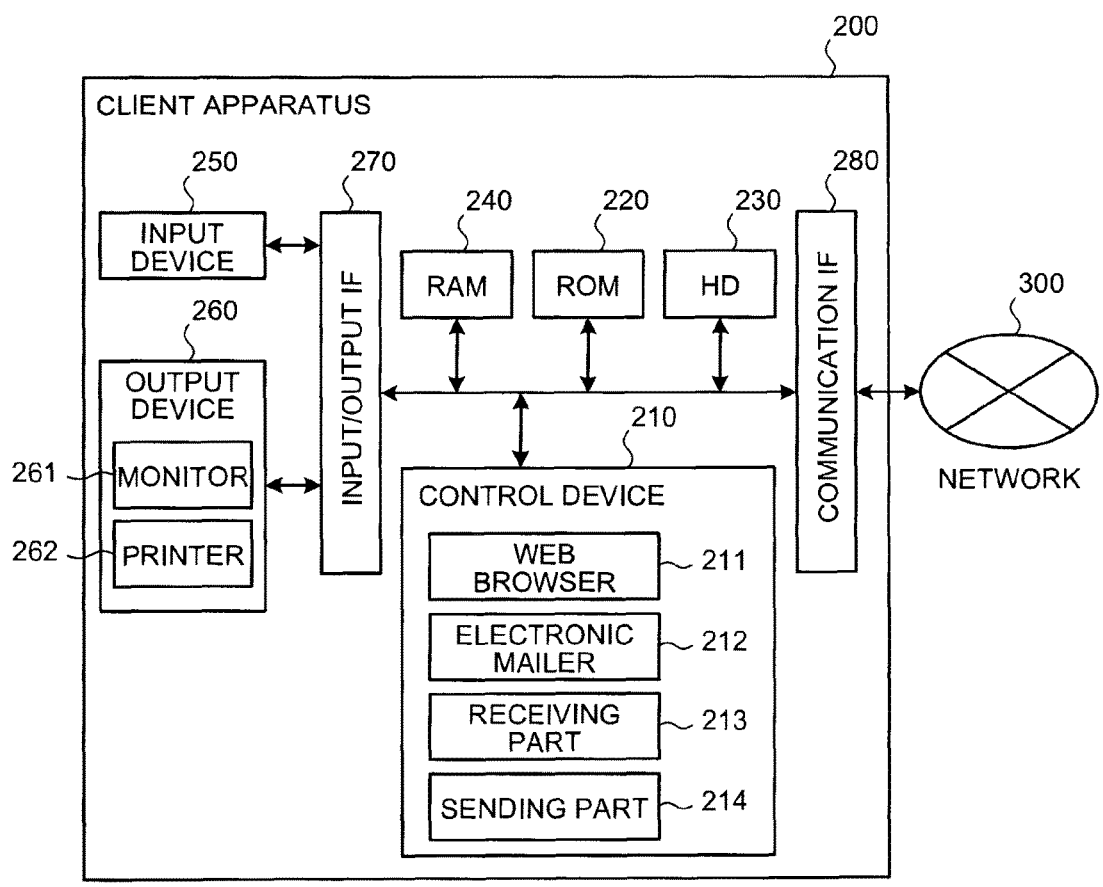
FIG. 19 is a block diagram showing an example of the configuration of the client apparatus 200 in the present system.

Hereinafter, the configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel.

The control device 210 has a Web browser 211, an electronic mailer 212, a receiving part 213, and a sending part 214. The Web browser 211 performs browsing processing of interpreting Web data and displaying the interpreted Web data on a monitor 261 described below. The Web browser 211 may have various plug-in software, such as stream player, having functions to receive, display and feedback streaming screen image. The electronic mailer 212 sends and receives electronic mails using a particular protocol (e.g., SMTP (Simple Mail Transfer Protocol) or POP3 (Post Office Protocol version 3)). The receiving part 213 receives various information, such as the evaluation results transmitted from the colorectal cancer-evaluating apparatus 100, via the communication IF 280. The sending part 214 sends various information such as the amino acid concentration data on the subject to be evaluated, via the communication IF 280, to the colorectal cancer-evaluating apparatus 100.

The input device 250 is for example a keyboard, a mouse or a microphone. The monitor 261 described below also functions as a pointing device together with a mouse. The output device 260 is an output means for outputting the information received via the communication IF 280, and includes the monitor (including home television) 261 and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as router) communicatively. In other words, the client apparatuses 200 are connected to the network 300 via a communication apparatus such as modem, TA (Terminal Adapter) or router, and a telephone line, or a private line. In this way, the client apparatuses 200 can access to the colorectal cancer-evaluating apparatus 100 by using a particular protocol.

The client apparatus 200 may be realized by installing software (including programs, data and others) for Web data-browsing function and electronic mail-processing function to information processing apparatus (for example, information processing terminal such as known personal computer, workstation, family computer, Internet TV (Television), PHS (Personal Handyphone System) terminal, mobile phone terminal, mobile unit communication terminal or PDA (Personal Digital Assistants)) connected as needed with peripheral devices such as printer, monitor, and image scanner.

All or a part of processings of the control device 210 in the client apparatus 200 may be performed by a CPU and programs read and executed by the CPU. Thus, computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in an application program server connected via any network to the client apparatus 200, and the client apparatus 200 may download all or a part of them as needed. All or any part of processings of the control device 210 may be realized by hardware such as wired-logic.

Hereinafter, the network 300 in the present system will be described with reference to FIGS. 4 and 5. The network 300 has a function to connect the colorectal cancer-evaluating apparatus 100, the client apparatuses 200, and the database apparatus 400 mutually, communicatively to one another, and is for example the Internet, intranet, or LAN (Local Area Network (both wired/wireless)). The network 300 may be VAN (Value Added Network), personal computer communication network, public telephone network (including both analog and digital), leased line network (including both analog and digital), CATV (Community Antenna Television) network, portable switched network or portable packet-switched network (including IMT2000 (International Mobile Telecommunication 2000) system, GSM (Global System for Mobile Communications) system, or PDC (Personal Digital Cellular)/PDC-P system), wireless calling network, local wireless network such as Bluetooth (registered trademark), PHS network, satellite communication network (including CS (Communication Satellite), BS (Broadcasting Satellite), and ISDB (Integrated Services Digital Broadcasting)), or the like.

Figure 20:
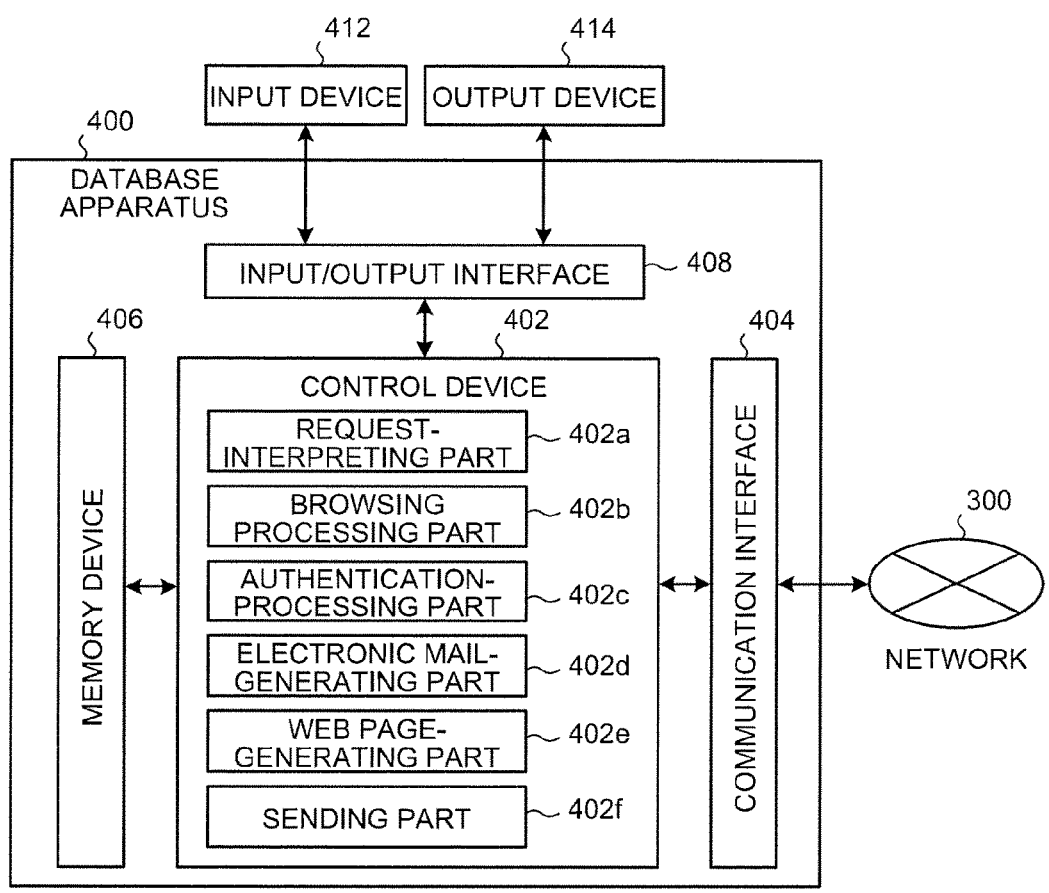
FIG. 20 is a block diagram showing an example of the configuration of the database apparatus 400 in the present system.

Hereinafter, the configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the colorectal cancer state information used in preparing a multivariate discriminant in the colorectal cancer-evaluating apparatus 100 or in the database apparatus 400, the multivariate discriminant prepared in the colorectal cancer-evaluating apparatus 100, and the evaluation results in the colorectal cancer-evaluating apparatus 100. As shown in FIG. 20, the database apparatus 400 includes a control device 402, such as CPU, which controls the entire database apparatus 400 integrally, a communication interface 404 connecting the database apparatus to the network 300 communicatively via a communication apparatus such as router and via a wired or wireless communication circuit such as private line, a memory device 406 storing various data, tables and files (for example, file for Web page), and an input/output interface 408 connected to an input device 412 and an output device 414, and these parts are connected communicatively to each other via any communication channel.

The memory device 406 is a storage means, and may be, for example, memory apparatus such as RAM or ROM, fixed disk drive such as harddisk, flexible disk, optical disk, or the like. Various programs used in various processings are stored in the memory device 406. The communication interface 404 allows communication between the database apparatus 400 and the network 300 (or communication apparatus such as router). Thus, the communication interface 404 has a function to communicate data with other terminal via a communication line. The input/output interface 408 is connected to the input device 412 and the output device 414. A monitor (including home television), a speaker, or a printer may be used as the output device 414 (hereinafter, the output device 414 may be described as monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processing according to these programs. As shown in the figure, the control device 402 includes mainly a request-interpreting part 402a, a browsing processing part 402b, an authentication-processing part 402c, an electronic mail-generating part 402d, a Web page-generating part 402e, and a sending part 402f.

The request-interpreting part 402a interprets the request from the colorectal cancer-evaluating apparatus 100 and sends the request to other parts in the control device 402 according to the analytical result. Upon receiving various screen-browsing request from the colorectal cancer-evaluating apparatus 100, the browsing processing part 402b generates and transmits web data for these screens. Upon receipt of authentication request from the colorectal cancer-evaluating apparatus 100, the authentication-processing part 402c performs authentication. The electronic mail-generating part 402d generates an electronic mail including various information. The Web page-generating part 402e generates a Web page for a user to browse with the client apparatus 200. The sending part 402f sends the information such as the colorectal cancer state information and the multivariate discriminant to the colorectal cancer-evaluating apparatus 100.

2-3. Processing in the Present System

Figure 21:
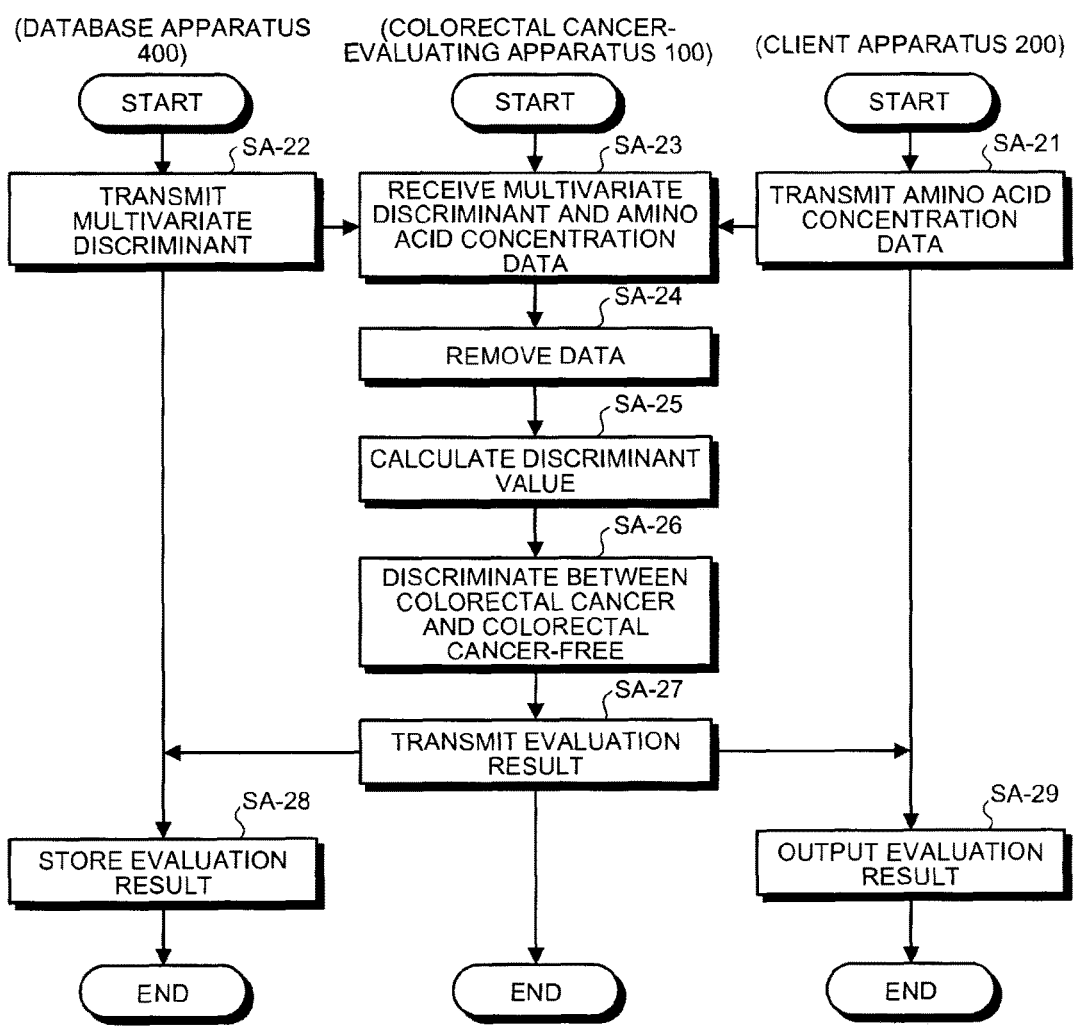
FIG. 21 is a flowchart showing an example of the colorectal cancer evaluation service processing performed in the present system.

Here, an example of the colorectal cancer evaluation service processing performed in the present system constituted as described above will be described with reference to FIG. 21. FIG. 21 is a flowchart showing an example of the colorectal cancer evaluation service processing.

The amino acid concentration data used in the present processing concerns amino acid concentration value obtained by analyzing blood previously collected from an individual. Hereinafter, the method of analyzing blood amino acid will be described briefly. First, a blood sample is collected in a heparin-treated tube, and then the blood plasma is separated by centrifugation of the tube. All blood plasma samples separated are frozen and stored at −70° C. before measurement of amino acid concentration. Before measurement of amino acid concentration, the blood plasma sample is deproteinized by adding sulfosalicylic acid to a concentration of 3%. An amino acid analyzer by high-performance liquid chromatography (HPLC) by using ninhydrin reaction in the post column was used for measurement of amino acid concentration.

First, the client apparatus 200 accesses the colorectal cancer-evaluating apparatus 100 when the user specifies the Web site address (such as URL) provided from the colorectal cancer-evaluating apparatus 100, via the input device 250 on the screen displaying Web browser 211. Specifically, when the user instructs update of the Web browser 211 screen on the client apparatus 200, the Web browser 211 sends the Web site's address provided from the colorectal cancer-evaluating apparatus 100 by a particular protocol, thereby transmitting a request demanding transmission of the Web page corresponding to the amino acid concentration data transmission screen to the colorectal cancer-evaluating apparatus 100 based on the routing of the address.

Then, upon receipt of the request from the client apparatus 200, the request-interpreting part 102a in the colorectal cancer-evaluating apparatus 100 analyzes the transmitted request and sends the request to other parts in the control device 102 according to the analytical result. Specifically, when the transmitted request is a request to send the Web page corresponding to the amino acid concentration data transmission screen, mainly the browsing processing part 102b in the colorectal cancer-evaluating apparatus 100 obtains the Web data for display of the Web page stored in a predetermined region of the memory device 106 and sends the obtained Web data to the client apparatus 200. More specifically, upon receiving the Web page transmission request corresponding to the amino acid concentration data transmission screen by the user, the control device 102 in the colorectal cancer-evaluating apparatus 100 demands input of user ID and user password from the user. If the user ID and password are input, the authentication-processing part 102c in the colorectal cancer-evaluating apparatus 100 examines the input user ID and password by comparing them with the user ID and user password stored in the user information file 106a for authentication. Only when the user is authenticated, the browsing processing part 102b in the colorectal cancer-evaluating apparatus 100 sends, to the client apparatus 200, the Web data for displaying the Web page corresponding to the amino acid concentration data transmission screen. The client apparatus 200 is identified with the IP (Internet Protocol) address transmitted from the client apparatus 200 together with the transmission request.

Then, the client apparatus 200 receives, in the receiving part 213, the Web data (for displaying the Web page corresponding to the amino acid concentration data transmission screen) transmitted from the colorectal cancer-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 sends an identifier for identifying input information and selected items to the colorectal cancer-evaluating apparatus 100, thereby transmitting the amino acid concentration data of the individual as the subject to be evaluated to the colorectal cancer-evaluating apparatus 100 (step SA-21). In step SA-21, transmission of the amino acid concentration data may be realized for example by using an existing file transfer technology such as FTP (File Transfer Protocol).

Then, the request-interpreting part 102a of the colorectal cancer-evaluating apparatus 100 interprets the identifier transmitted from the client apparatus 200 thereby analyzing the request from the client apparatus 200, and requests the database apparatus 400 to send the multivariate discriminant for colorectal cancer evaluation (specifically for discrimination of the 2 groups of colorectal cancer and colorectal cancer-free).

Then, the request-interpreting part 402a of the database apparatus 400 interprets the transmission request from the colorectal cancer-evaluating apparatus 100 and transmits, to the colorectal cancer-evaluating apparatus 100, the multivariate discriminant (for example, the updated newest multivariate discriminant) containing at least one of Arg, Cys, Orn, Trp, Glu, ABA, Val, Phe, Leu, Gln, Ile and His as explanatory variables, stored in a predetermined region of the memory device 406 (step SA-22).

In step SA-22, the multivariate discriminant transmitted to the colorectal cancer-evaluating apparatus 100 may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant transmitted to the colorectal cancer-evaluating apparatus 100 may be formula 1 or 2:

$$a_1 \times Orn/(Trp+His)+b_1 \times (ABA+Ile)/Leu+c_1 \quad \text{(formula 1)}$$

$$a_2 \times Gln/Val+b_2 \times Cit/ABA+c_2 \times Thr/Glu+d_2 \quad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real number.

In step SA-22, the multivariate discriminant transmitted to the colorectal cancer-evaluating apparatus 100 may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant transmitted to the colorectal cancer-evaluating apparatus 100 may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables.

The colorectal cancer-evaluating apparatus 100 receives, in the receiving part 102f, the amino acid concentration data of the individual transmitted from the client apparatuses 200 and the multivariate discriminant transmitted from the database apparatus 400, and stores the received amino acid concentration data in a predetermined memory region of the amino acid concentration data file 106b and the received multivariate discriminant in a predetermined memory region of the multivariate discriminant file 106e4 (step SA-23).

In the control device 102 of the colorectal cancer-evaluating apparatus 100, data such as defective and outliers are then removed from the amino acid concentration data of the individual received in step SA-23 (step SA-24).

Then, the colorectal cancer-evaluating apparatus 100 calculates the discriminant value in the discriminant value-calculating part 102i, based on the multivariate discriminant received in step SA-23 and the amino acid concentration data of the individual from which defective and outliers have been removed in step SA-24 (step SA-25).

Then, the discriminant value criterion-discriminating part 102j1 of the colorectal cancer-evaluating apparatus 100 compares the discriminant value calculated in step SA-25 with a previously established threshold (cutoff value), thereby discriminating between colorectal cancer and colorectal cancer-free in the individual, and the discrimination results are stored in a predetermined memory region of the evaluation result file 106g (step SA-26).

The sending part 102m of the colorectal cancer-evaluating apparatus 100 then sends the discrimination results (discrimination results as to discrimination between colorectal cancer and colorectal cancer-free) obtained in step SA-26 to the client apparatus 200 that has sent the amino acid concentration data and to the database apparatus 400 (step SA-27). Specifically, the colorectal cancer-evaluating apparatus 100 first generates a Web page for display of discrimination results in the Web page-generating part 102e and stores the Web data corresponding to the generated Web page, in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the colorectal cancer-evaluating apparatus 100. The colorectal cancer-evaluating apparatus 100 then examines the browsing request transmitted from the client apparatus 200 in the browsing processing part 102b and reads the Web data corresponding to the Web page for displaying the discrimination results, out of the predetermined memory region of the memory device 106. The sending part 102m of the colorectal cancer-evaluating apparatus 100 then sends the read-out Web data to the client apparatus 200 and simultaneously sends the Web data or the discrimination results to the database apparatus 400.

In step SA-27, the control device 102 of the colorectal cancer-evaluating apparatus 100 may notify the discrimination results to the user client apparatus 200 by electronic mail. Specifically, the colorectal cancer-evaluating apparatus 100 first acquires the user electronic mail address in the electronic mail-generating part 102d at the transmission timing for example based on the user ID, with reference to the user information stored in the user information file 106a. The colorectal cancer-evaluating apparatus 100 then generates electronic mail data including user name and discrimination result, with the electronic mail address obtained as its mail address in the electronic mail-generating part 102d. The sending part 102m of the colorectal cancer-evaluating apparatus 100 then sends the generated data to the user client apparatus 200.

Also in step SA-27, the colorectal cancer-evaluating apparatus 100 may send the discrimination results to the user client apparatus 200 by using an existing file transfer technology such as FTP.

Returning to FIG. 21, the control device 402 in the database apparatus 400 receives the discrimination results or the Web data transmitted from the colorectal cancer-evaluating apparatus 100 and stores (accumulates) the received discrimination results or Web data in a predetermined memory region of the memory device 406 (step SA-28).

The receiving part 213 of the client apparatus 200 receives the Web data transmitted from the colorectal cancer-evaluating apparatus 100, and the received Web data are interpreted with the Web browser 211, to display on the monitor 261 the Web page screen displaying the discrimination result of the individual (step SA-29). When the discrimination results are sent from the colorectal cancer-evaluating apparatus 100 by electronic mail, the electronic mail transmitted from the colorectal cancer-evaluating apparatus 100 is received at any timing, and the received electronic mail is displayed on the monitor 261 with the known function of the electronic mailer 212 of the client apparatus 200.

In this way, the user knows the discrimination results as to the discrimination of the 2 groups of colorectal cancer and colorectal cancer-free in the individual, by browsing the Web page displayed on the monitor 261. The user can print out the content of the Web page displayed on the monitor 261 by the printer 262.

When the discrimination results are transmitted by electronic mail from the colorectal cancer-evaluating apparatus 100, the user reads the electronic mail displayed on the monitor 261, whereby the user can confirm the discrimination results as to the discrimination of the 2 groups of colorectal cancer and colorectal cancer-free in the individual. The user may print out the content of the electronic mail displayed on the monitor 261 by the printer 262.

Given the foregoing description, the explanation of the colorectal cancer evaluation service processing is finished.

2-4. Summary of the Second Embodiment and Other Embodiments

According to the colorectal cancer-evaluating system described above in detail, the client apparatus 200 sends the amino acid concentration data of the individual to the colorectal cancer-evaluating apparatus 100, and upon receiving a request from the colorectal cancer-evaluating apparatus 100, the database apparatus 400 transmits the multivariate discriminant for discrimination of the 2 groups of colorectal cancer and colorectal cancer-free to the colorectal cancer-evaluating apparatus 100. By the colorectal cancer-evaluating apparatus 100, the amino acid concentration data are received from the client apparatus 200, and simultaneously the multivariate discriminant is received from the database apparatus 400, the discriminant value is calculated based on the received amino acid concentration data and the received multivariate discriminant, the calculated discriminant value is compared with the previously established threshold, thereby discriminating between colorectal cancer and colorectal cancer-free in the individual, and this discrimination result is transmitted to the client apparatus 200 and database apparatus 400. Then, the client apparatus 200 receives and displays the discrimination result transmitted from the colorectal cancer-evaluating apparatus 100, and the database apparatus 400 receives and stores the discrimination result transmitted from the colorectal cancer-evaluating apparatus 100. Thus, a discriminant value obtained in a multivariate discriminant useful for discriminating between the 2 groups of colorectal cancer and colorectal cancer-free can be utilized to bring about an effect of enabling accurate discrimination between the 2 groups of colorectal cancer and colorectal cancer-free.

According to the colorectal cancer-evaluating system, the multivariate discriminant may be expressed by one fractional expression or the sum of a plurality of the fractional expressions and may contain at least one of Arg, Cys, Orn, Trp, Glu, ABA, Val, Phe, Leu, Gln, Ile and His as the explanatory variable in any one of the numerator and denominator or both in the fractional expression constituting the multivariate discriminant. Specifically, the multivariate discriminant may be formula 1 or 2:

$$a_1 \times Orn/(Trp+His) + b_1 \times (ABA+Ile)/Leu + c_1 \qquad \text{(formula 1)}$$

$$a_2 \times Gln/Val + b_2 \times Cit/ABA + c_2 \times Thr/Glu + d_2 \qquad \text{(formula 2)}$$

wherein $a_1$ and $b_1$ in the formula 1 are arbitrary non-zero real numbers, $c_1$ in the formula 1 is arbitrary real number, $a_2$, $b_2$ and $c_2$ in the formula 2 are arbitrary non-zero real numbers, and $d_2$ in the formula 2 is arbitrary real numbers. Thus, a discriminant value obtained in a multivariate discriminant useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in evaluation of a colorectal cancer state, regardless of the unit of amino acid concentration in the amino acid concentration data as input data.

According to the colorectal cancer-evaluating system, the multivariate discriminant may be any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Specifically, the multivariate discriminant may be the logistic regression equation with Orn, Gln, Trp and Cit as the explanatory variables, the linear discriminant with Orn, Gln, Trp, Phe, Cit and Tyr as the explanatory variables, the logistic regression equation with Val, Glu, Thr, ABA, Gln and Pro as the explanatory variables, or the linear discriminant with Ile, His, Glu and ABA as the explanatory variables. Thus, a discriminant value obtained in a multivariate discriminant using amino acid explanatory variables useful particularly for discriminating between the 2 groups of colorectal cancer and colorectal cancer-free can be utilized to bring about an effect of enabling more accurate discrimination between the 2 groups of colorectal cancer and colorectal cancer-free. The multivariate discriminants described above can be prepared by a method (multivariate discriminant-preparing processing described later) described in International Publication WO 2006/098192 that is an international application filed by the present applicant.

In addition to the second embodiment described above, the colorectal cancer-evaluating apparatus, the colorectal cancer-evaluating method, the colorectal cancer-evaluating system, the colorectal cancer-evaluating program product and the recording medium according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the colorectal cancer-evaluating apparatus 100 shown in the figures are conceptual and functional and may not be the same physically as those shown in the figure. In addition, all or a part of the operational function of each component and each device in the colorectal cancer-evaluating apparatus 100 (in particular, processings in the control device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may not be configured singly, and may be operated together with plurality of modules and libraries or with a different program such as OS (Operating System) to achieve the function. The program is stored on a recording medium and read mechanically as needed by the colorectal cancer-evaluating apparatus 100. Any well-known configuration or procedure may be used for reading the programs recorded on the recording medium in each apparatus and for reading procedure and installation of the procedure after reading.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), and the like. Examples of the "fixed physical media" include various media installed in a computer system such as ROM, RAM, and HD. The "communication media" for example stores the program for a short period of time such as communication line and carrier wave when the program is transmitted via a network such as LAN (Local Area Network), WAN (Wide Area Network), or the Internet.

Figure 22:
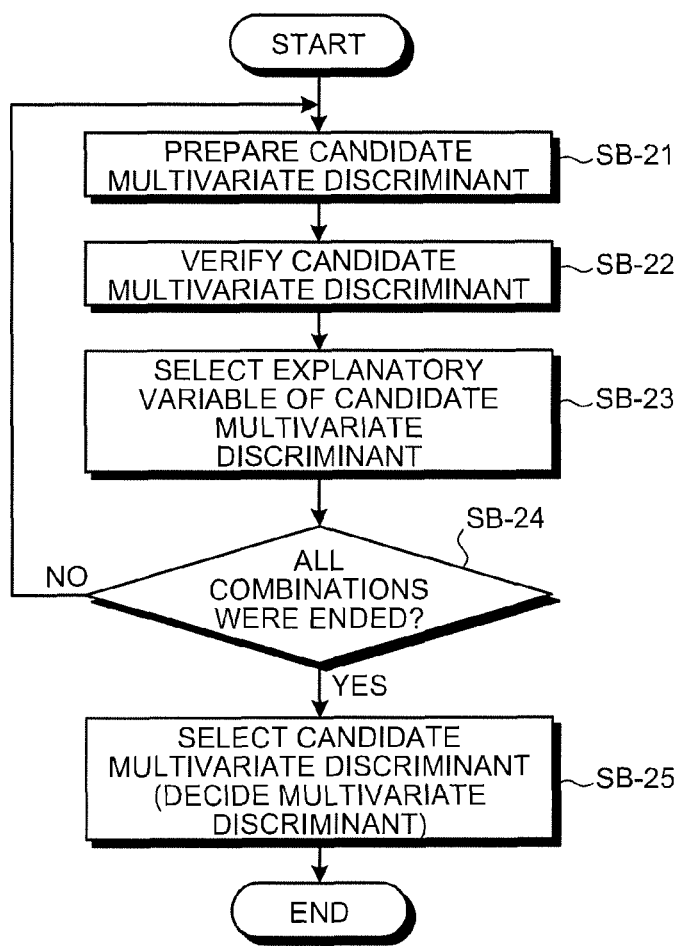
FIG. 22 is a flowchart showing an example of the multivariate discriminant-preparing processing performed in the colorectal cancer-evaluating apparatus 100 in the present system.

Finally, an example of the multivariate discriminant-preparing processing performed in the colorectal cancer-evaluating apparatus 100 is described in detail with reference to FIG. 22. FIG. 22 is a flowchart showing an example of the multivariate discriminant-preparing processing. The multivariate discriminant-preparing processing may be performed in the database apparatus 400 handling the colorectal cancer state information.

In the present description, the colorectal cancer-evaluating apparatus 100 stores the colorectal cancer state information previously obtained from the database apparatus 400 in a predetermined memory region of the colorectal cancer state information file 106c. The colorectal cancer-evaluating apparatus 100 shall store, in a predetermined memory region of the designated colorectal cancer state information file 106d, the colorectal cancer state information including the colorectal cancer state index data and amino acid concentration data designated previously in the colorectal cancer state information-designating part 102g.

According to a predetermined discriminant-preparing method, the candidate multivariate discriminant-preparing part 102h1 in the multivariate discriminant-preparing part 102h first prepares a candidate multivariate discriminant from the colorectal cancer state information stored in a predetermine memory region of the designated colorectal cancer state information file 106d, and the prepared candidate multivariate discriminate is stored in a predetermined memory region of the candidate multivariate discriminant file 106e1 (step SB-21). Specifically, the candidate multivariate discriminant-preparing part 102h1 in the multivariate discriminant-preparing part 102h first selects a desired method out of a plurality of different discriminant-preparing methods (including multivariate analysis methods such as principal component analysis, discriminant analysis, support vector machine, multiple regression analysis, logistic regression analysis, k-means method, cluster analysis, and decision tree and the like) and determines the form of the candidate multivariate discriminant to be prepared based on the selected discriminant-preparing method. The candidate multivariate discriminant-preparing part 102h1 in the multivariate discriminant-preparing part 102h then performs various calculation corresponding to the selected function-selecting method (e.g., average or variance), based on the colorectal cancer state information. The candidate multivariate discriminant-preparing part 102h1 in the multivariate discriminant-preparing part 102h then determines the parameters for the calculation result and the determined candidate multivariate discriminant. In this way, a candidate multivariate discriminant is generated based on the selected discriminant-preparing method. When candidate multivariate discriminants are generated simultaneously and concurrently (in parallel) by using a plurality of different discriminant-preparing methods in combination, the processings described above may be executed concurrently for each selected discriminant-preparing method. Alternatively when candidate multivariate discriminants are to be generated in series by using a plurality of different discriminant-preparing methods in combination, for example, candidate multivariate discriminants may be generated by converting colorectal cancer state information with a candidate multivariate discriminant prepared by performing principal component analysis and performing discriminant analysis of the converted colorectal cancer state information.

The candidate multivariate discriminant-verifying part 102h2 in the multivariate discriminant-preparing part 102h verifies (mutually verifies) the candidate multivariate discriminant prepared in step SB-21 according to a particular verification method and stores the verification result in a predetermined memory region of the verification result file 106e2 (step SB-22). Specifically, the candidate multivariate discriminant-verifying part 102h2 in the multivariate discriminant-preparing part 102h first generates the verification data to be used in verification of the candidate multivariate discriminant, based on the colorectal cancer state information stored in a predetermined memory region of the designated colorectal cancer state information file 106d, and verifies the candidate multivariate discriminant according to the generated verification data. If a plurality of candidate multivariate discriminants are generated by using a plurality of different discriminant-preparing methods in step SB-21, the candidate multivariate discriminant-verifying part 102h2 in the multivariate discriminant-preparing part 102h verifies each candidate multivariate discriminant corresponding to each discriminant-preparing method according to a particular verification method. Here in step SB-22, at least one of the discrimination rate, sensitivity, specificity, information criterion, and the like of the candidate multivariate discriminant may be verified based on at least one method of the bootstrap, holdout, leave-one-out, and other methods. Thus, it is possible to select a candidate multivariate discriminant higher in predictability or reliability, based on the colorectal cancer state information and diagnostic condition.

Then, the explanatory variable-selecting part 102h3 in the multivariate discriminant-preparing part 102h selects the combination of amino acid concentration data contained in the colorectal cancer state information to be used in preparing the candidate multivariate discriminant by selecting an explanatory variable of the candidate multivariate discriminant from the verification results in step SB-22 according to a particular explanatory variable selection method, and stores the colorectal cancer state information including the selected combination of amino acid concentration data in a predetermined memory region of the selected colorectal cancer state information file 106e3 (step SB-23). When a plurality of candidate multivariate discriminants are generated by using a plurality of different discriminant-preparing methods in step SB-21 and each candidate multivariate discriminant corresponding to each discriminant-preparing method is verified according to a particular verification method in step SB-22, the explanatory variable-selecting part 102h3 in the multivariate discriminant-preparing part 102h selects the explanatory variable of the candidate multivariate discriminant for each candidate multivariate discriminant corresponding to the verification result obtained in step SB-22, according to a particular explanatory variable selection method in step SB-23. Here in step SB-23, the explanatory variable of the candidate multivariate discriminant may be selected from the verification results according to at least one of stepwise method, best path method, local search method, and genetic algorithm. The best path method is a method of selecting an explanatory variable by optimizing the evaluation index of the candidate multivariate discriminant while eliminating the explanatory variables contained in the candidate multivariate discriminant one by one. In step SB-23, the explanatory variable-selecting part 102h3 in the multivariate discriminant-preparing part 102h may select the combination of amino acid concentration data based on the colorectal cancer state information stored in a predetermined memory region of the designated colorectal cancer state information file 106d.

The multivariate discriminant-preparing part 102h then judges whether all combinations of the amino acid concentration data contained in the colorectal cancer state information stored in a predetermined memory region of the designated colorectal cancer state information file 106d are processed, and if the judgment result is "End" (Yes in step SB-24), the processing advances to the next step (step SB-25), and if the judgment result is not "End" (No in step SB-24), it returns to step SB-21. The multivariate discriminant-preparing part 102h judges whether the processing is performed a predetermined number of times, and if the judgment result is "End" (Yes in step SB-24), the processing may advance to the next step (step SB-25), and if the judgment result is not "End" (No in step SB-24), it returns to step SB-21. The multivariate discriminant-preparing part 102h may judge whether the combination of the amino acid concentration data selected in step SB-23 is the same as the combination of the amino acid concentration data contained in the colorectal cancer state information stored in a predetermined memory region of the designated colorectal cancer state information file 106d or the combination of the amino acid concentration data selected in the previous step SB-23, and if the judgment result is "the same" (Yes in step SB-24), the processing may advance to the next step (step SB-25) and if the judgment result is not "the same" (No in step SB-24), it may return to step SB-21. If the verification result is specifically the evaluation value for each multivariate discriminant, the multivariate discriminant-preparing part 102h may advance to step SB-25 or return to step SB-21, based on the comparison of the evaluation value with a particular threshold corresponding to each discriminant-preparing method.

Then, the multivariate discriminant-preparing part 102h determines the multivariate discriminant based on the verification results by selecting a candidate multivariate discriminant to be used as the multivariate discriminant among the candidate multivariate discriminants, and stores the determined multivariate discriminant (selected candidate multivariate discriminant) in particular memory region of the multivariate discriminant file 106e4 (step SB-25). Here, in step SB-25, for example, the optimal multivariate discriminant may be selected from the candidate multivariate discriminants prepared by the same discriminant-preparing method or from all candidate multivariate discriminants.

These are description of the multivariate discriminant-preparing processing.

EXAMPLE 1

Figure 23:
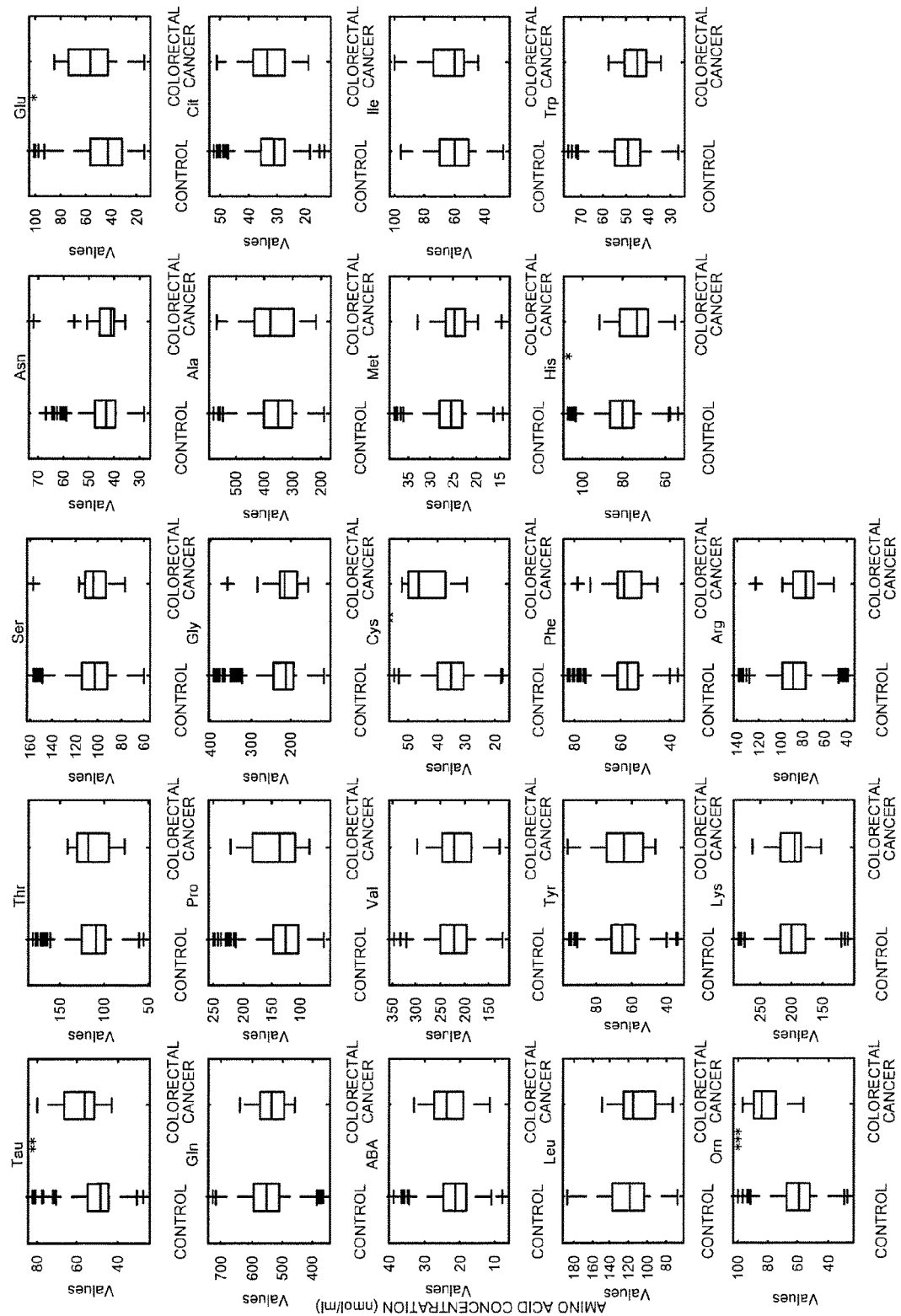
FIG. 23 is a boxplot showing the distribution of amino acid explanatory variables between 2 groups of colorectal cancer-free and colorectal cancer.

Blood samples of a group of colorectal cancer patients definitively diagnosed as colorectal cancer by colorectal biopsy, and blood samples of a group of colorectal cancer-free patients, were subjected to measurement of the amino acid concentration in blood by the amino acid analysis method. The unit of amino acid concentration is nmol/ml. FIG. 23 is a boxplot showing the distribution of amino acid explanatory variables in the colorectal cancer patients and the colorectal cancer-free patients. In FIG. 23, the horizontal axis indicates the colorectal cancer-free group (control group) and the colorectal cancer group, and ABA and Cys in the figure represent α-ABA (α-aminobutyric acid) and Cystine, respectively. For the purpose of discrimination between the colorectal cancer group and the colorectal cancer-free group, a t-test between the 2 groups was performed.

In the colorectal cancer group as compared with the colorectal cancer-free group, Tau, Glu, Cys and Orn significantly increased (probability of significant difference P<0.05), and His significantly decreased. Thus, it was made clear that amino acid explanatory variables Tau, Glu, Cys, Orn and His have an ability to discriminate between the 2 groups of colorectal cancer group and colorectal cancer-free group.

Figure 24:
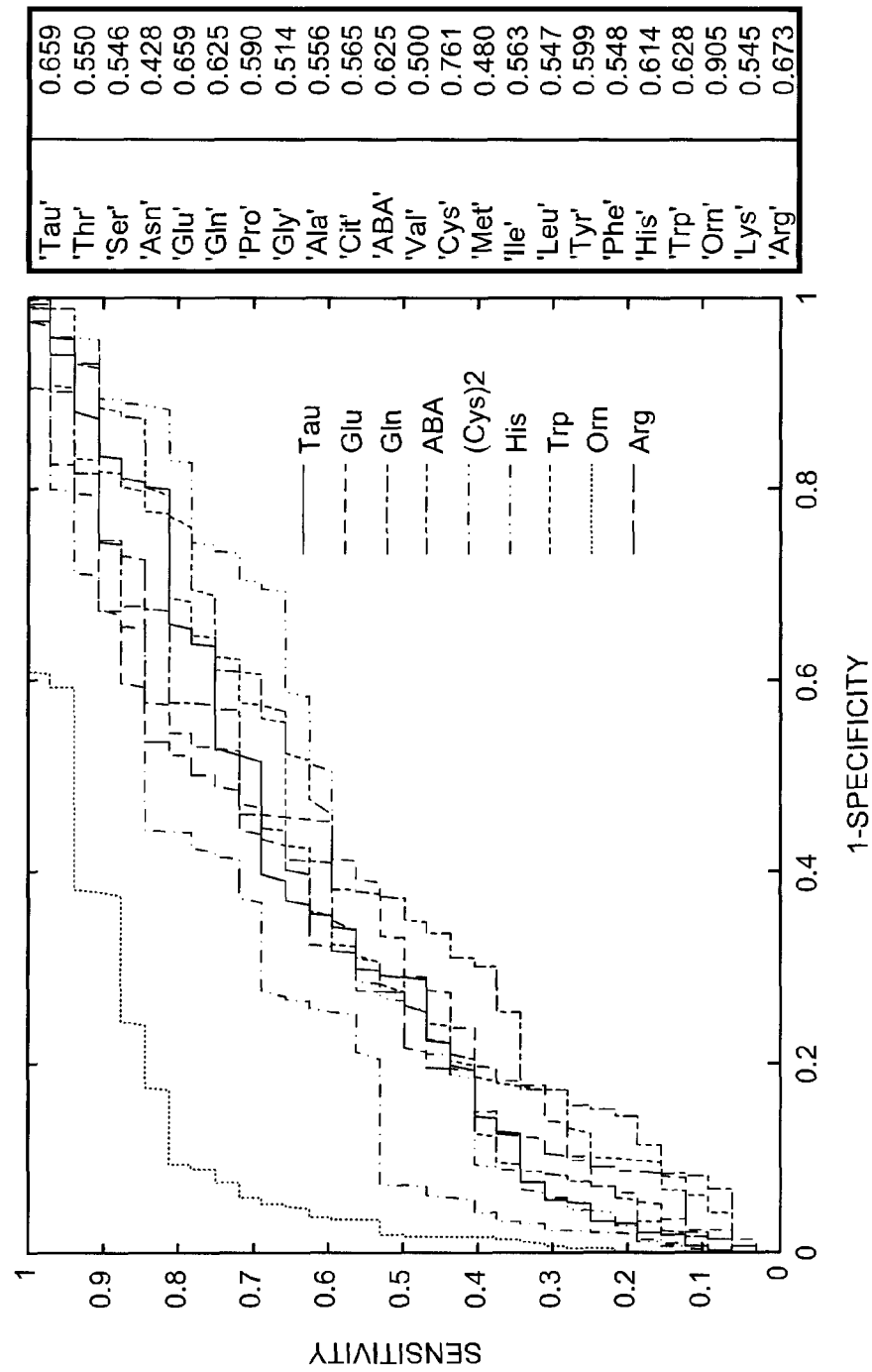
FIG. 24 is a graph showing the AUC of the ROC curve of amino acid explanatory variables.

Furthermore, an evaluation using the area under curve (AUC) of an ROC (receiver operating characteristic) curve (FIG. 24) was carried out for the discrimination between the 2 groups of colorectal cancer group and colorectal cancer-free group based on the respective amino acid explanatory variables, and the AUC showed values larger than 0.65 for the amino acid explanatory variables Tau, Glu, Cys, Orn and Arg. Therefore, it was made clear that the amino acid explanatory variables Tau, Glu, Cys, Orn and Arg have an ability to discriminate between the 2 groups of colorectal cancer group and colorectal cancer-free group.

EXAMPLE 2

The sample data used in Example 1 were used. Using a method described in International Publication WO 2004/052191 that is an international application filed by the present applicant, an index by which the performance of discriminating between the 2 groups of colorectal cancer group and colorectal cancer-free group is maximized with regard to the discrimination of colorectal cancer was eagerly searched, and an index formula 1 was obtained among a plurality of indices having an equivalent performance.

$$(Orn)/(Trp+His)+(ABA+Ile)/(Leu) \quad \text{Index formula 1}$$

Figure 25:
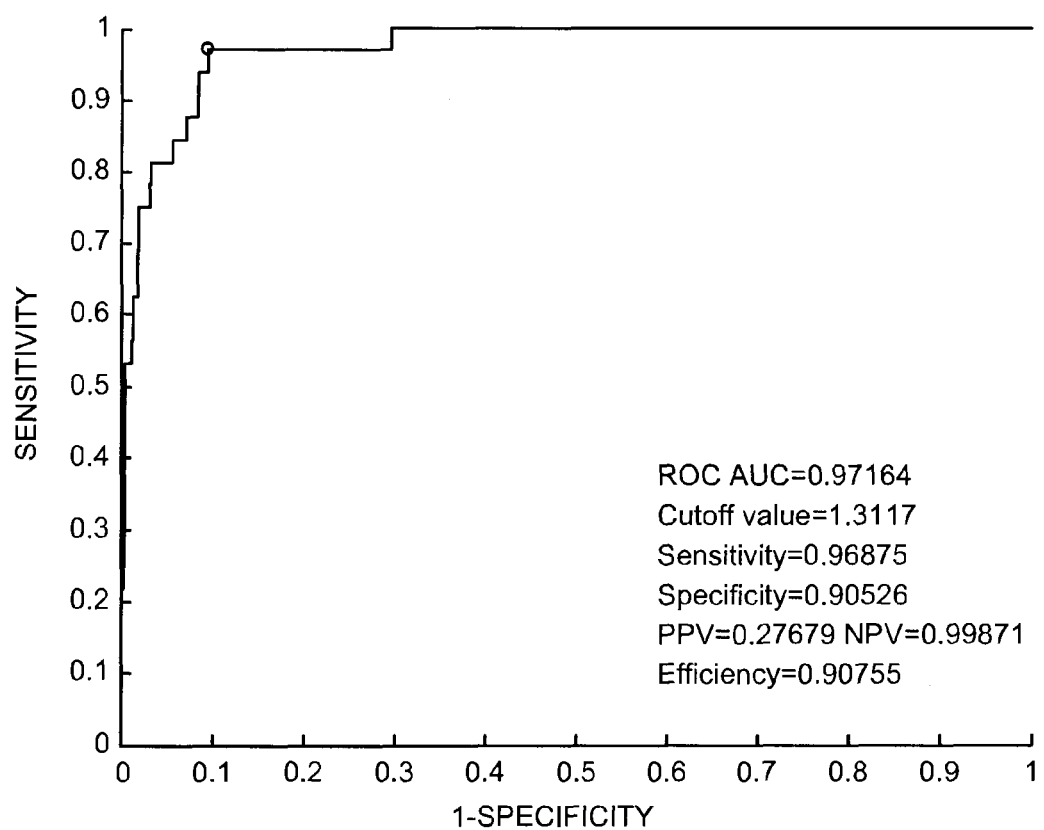
FIG. 25 is a graph showing an ROC curve for evaluation of diagnostic performance between 2 groups.

The performance for diagnosis of colorectal cancer based on the index formula 1 was evaluated based on the AUC of the ROC curve (FIG. 25) in connection with the discrimination between the 2 groups of colorectal cancer group and colorectal cancer-free group, and an AUC of 0.972±0.010 (95% confidence interval: 0.952 to 0.992) was obtained. When the optimum cutoff value for the discrimination between the 2 groups of colorectal cancer group and colorectal cancer-free group by the index formula 1 was determined assuming that the symptom prevalence of the colorectal cancer group was 0.038, the cutoff value was 1.311, and a sensitivity of 97%, a specificity of 91%, a positive predictive value of 28%, a negative predictive value of 99%, and a correct diagnostic rate of 91% were obtained (FIG. 26). Thus, the index formula 1 was found to be a useful index with high diagnostic performance. In addition to that, a plurality of fractional expressions having a discrimination performance equivalent to that of the index formula 1 was obtained. Those fractional expressions are presented in FIG. 27, FIG. 28, FIG. 29 and FIG. 30.

EXAMPLE 3

The sample data used in Example 1 were used. An index by which the performance of discriminating between the 2 groups of colorectal cancer group and colorectal cancer-free group is maximized with regard to colorectal cancer was searched by logistic analysis (explanatory variable coverage method based on the BIC (bayesian information criterion) minimum criterion), and a logistic regression equation composed of Orn, Gln, Trp and Cit (the numerical coefficients of the amino acid explanatory variables Orn, Gln, Trp and Cit and the constant terms are, in the same order, 0.190±0.026, −0.012±0.004, −0.172±0.037, −0.110±0.040, and 1.060±2.681, respectively) was obtained as an index formula 2.

Figure 31:
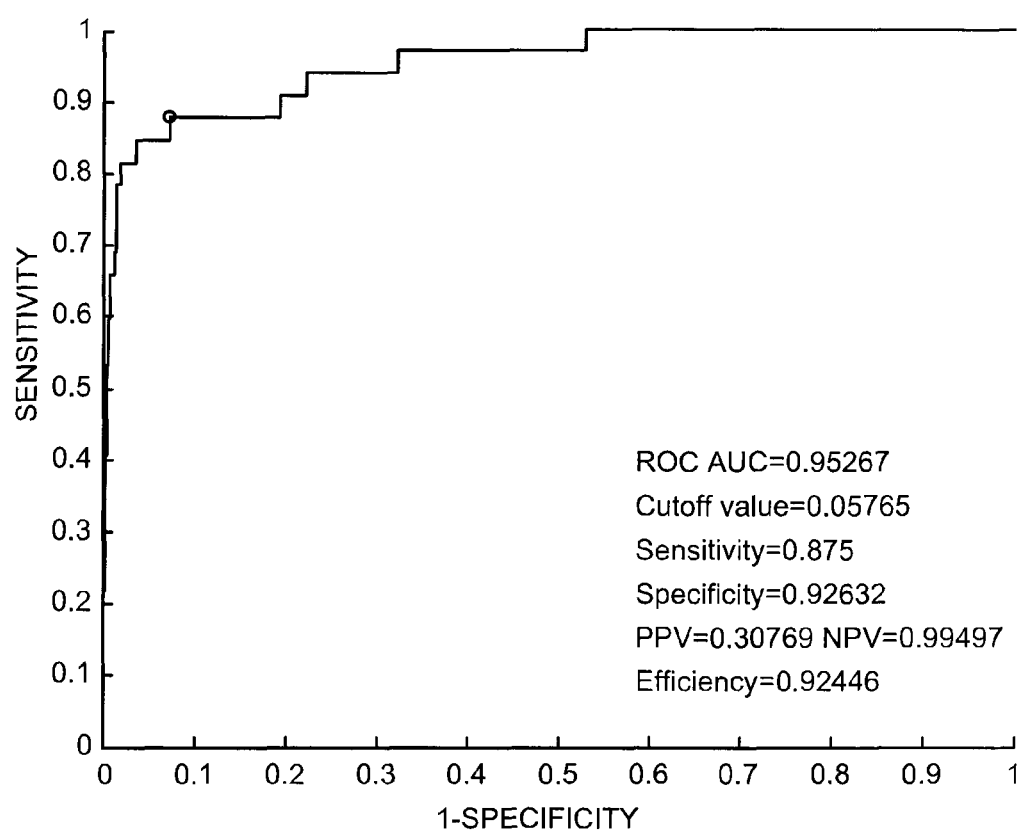
FIG. 31 is a graph showing an ROC curve for evaluation of diagnostic performance between 2 groups.

The performance for diagnosis of colorectal cancer based on the index formula 2 was evaluated based on the AUC of the ROC curve (FIG. 31) in connection with the discrimination between the 2 groups of colorectal cancer group and colorectal cancer-free group, and an AUC of 0.953±0.020 (95% confidence interval: 0.913 to 0.992) was obtained. Thus, the index formula 2 was found to be a useful index with high diagnostic performance. When the optimum cutoff value for the discrimination between the 2 groups of colorectal cancer group and colorectal cancer-free group by the index formula 2 was determined assuming that the symptom prevalence of the colorectal cancer group was 0.036, the cutoff value was 0.057, and a sensitivity of 88%, a specificity of 93%, a positive predictive value of 31%, a negative predictive value of 99%, and a correct diagnostic rate of 92% were obtained (FIG. 32). Thus, the index formula 2 was found to be a useful index with high diagnostic performance. In addition to that, a plurality of logistic regression equations having a discrimination performance equivalent to that of the index formula 2 was obtained. Those logistic regression equations are presented in FIG. 33, FIG. 34, FIG. 35 and FIG. 36. The respective values of the coefficients and 95% confidence intervals thereof for the equations presented in FIG. 33, FIG. 34, FIG. 35 and FIG. 36 may be values multiplied by a real number, and the values of the constant terms and 95% confidence intervals thereof may be values obtained by addition, subtraction, multiplication or division by an arbitrary real constant.

EXAMPLE 4

The sample data used in Example 1 were used. An index by which the performance of discriminating between the 2 groups of colorectal cancer group and colorectal cancer-free group is maximized with regard to colorectal cancer was searched by linear discriminant analysis (explanatory variable coverage method), and a linear discriminant function composed of Orn, Gln, Trp, Phe, Cit and Tyr (the numerical coefficients for the amino acid explanatory variables Orn, Gln, Trp, Phe, Cit and Tyr are, in the same order, 15.258±1.929, 1.000±0.372, −6.581±3.059, 7.328±3.346, −6.492±3.880, and −6.753±2.744, respectively) was obtained as an index formula 3.

Figure 37:
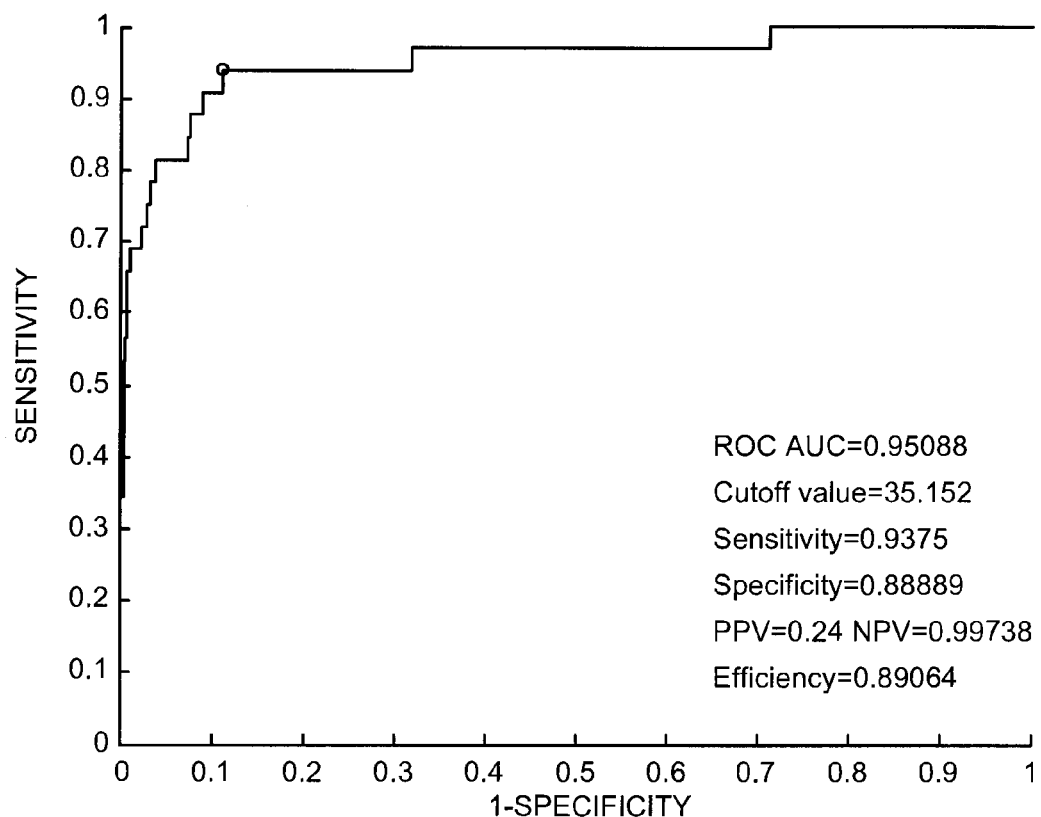
FIG. 37 is a graph showing an ROC curve for evaluation of diagnostic performance between 2 groups.

The performance for diagnosis of colorectal cancer based on the index formula 3 was evaluated based on the AUC of the ROC curve (FIG. 37) in connection with the discrimination between the 2 groups of colorectal cancer group and colorectal cancer-free group, and an AUC of 0.951±0.024 (95% confidence interval: 0.904 to 0.997) was obtained. Thus, the index formula 3 was found to be a useful index with high diagnostic performance. When the optimum cutoff value for the discrimination between the 2 groups of colorectal cancer group and colorectal cancer-free group by the index formula 3 was determined assuming that the symptom prevalence of the colorectal cancer group was 0.038, the cutoff value was 35.15, and a sensitivity of 94%, a specificity of 89%, a positive predictive value of 24%, a negative predictive value of 99%, and a correct diagnostic rate of 89% were obtained (FIG. 38). Thus, the index formula 3 was found to be a useful index with high diagnostic performance.

In addition to that, a plurality of linear discriminants having a discrimination performance equivalent to that of the index formula 3 was obtained. Those linear discriminants are presented in FIG. 39, FIG. 40, FIG. 41 and FIG. 42. The respective values of the coefficients and 95% confidence intervals thereof for the discriminants presented in FIG. 39, FIG. 40, FIG. 41 and FIG. 42 may be values multiplied by a real number, and the values of the constant terms and 95% confidence intervals thereof may be values obtained by addition, subtraction, multiplication or division by an arbitrary real constant.

EXAMPLE 5

The sample data used in Example 1 were used. All linear discriminants for performing discrimination between the 2 groups of colorectal cancer group and colorectal cancer-free group with regard to colorectal cancer, were extracted by the explanatory variable coverage method. Assuming that the maximum value of the amino acid explanatory variables appearing in each discriminant was 6, the area under the ROC curve of every discriminant satisfying this condition was calculated. Here, measurement was made of the frequency of each amino acid appearing in the discriminant in which the area under the ROC curve was equal to or greater than a certain threshold value, and as a result, Arg, Cys, Orn, Trp and Ile were verified to be included in top 10 amino acids which are always extracted at high frequency when areas under the ROC curve of 0.7, 0.75, 0.8 and 0.85 were respectively taken as the threshold values. Thus, it was made clear that the multivariate discriminant using these amino acids as explanatory variables has an ability to discriminate between the 2 groups of colorectal cancer group and colorectal cancer-free group (FIG. 43).

EXAMPLE 6

Figure 44:
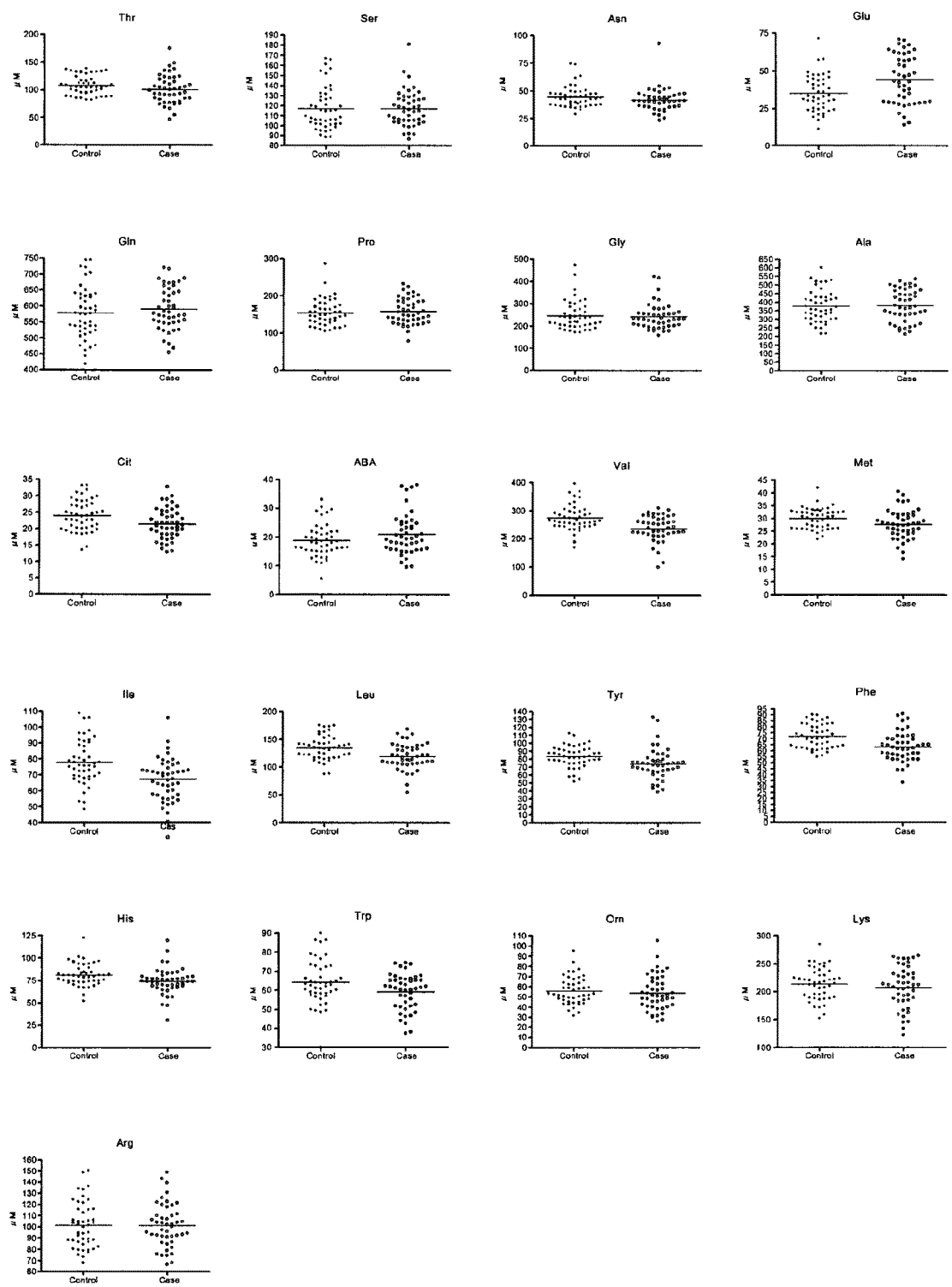
FIG. 44 is a boxplot showing the distribution of amino acid explanatory variables of colorectal cancer patients and colorectal cancer-free patients.

Blood samples of a group of colorectal cancer patients diagnosed as colorectal cancer by colorectal biopsy, and blood samples of a group of colorectal cancer-free patients, were subjected to measurement of the amino acid concentration in blood by the amino acid analysis method. FIG. 44 is a diagram showing the distribution of amino acid explanatory variables in the colorectal cancer patients and the colorectal cancer-free patients. For the purpose of discrimination between the colorectal cancer group and the colorectal cancer-free group, a t-test between the 2 groups was performed.

In the colorectal cancer group as compared with the colorectal cancer-free group, Glu significantly increased, and Cit, Val, Met, Ile, Leu, Tyr, Phe, His and Trp significantly decreased. Thus, it was made clear that amino acid explanatory variables Glu, Cit, Val, Met, Ile, Leu, Tyr, Phe, His and Trp have an ability to discriminate between the 2 groups of colorectal cancer group and colorectal cancer-free group.

Furthermore, an evaluation using the AUC of an ROC curve was carried out for the discrimination between the 2 groups of colorectal cancer group and colorectal cancer-free group, and the AUC of the amino acid explanatory variables Glu, Cit, Val, Ile, Leu, Tyr, Phe and His showed values larger than 0.65 (FIG. 45). Therefore, it was made clear that the amino acid explanatory variables Glu, Cit, Val, Ile, Leu, Tyr, Phe and His have an ability to discriminate between the 2 groups of colorectal cancer group and colorectal cancer-free group.

EXAMPLE 7

The sample data used in Example 6 were used. Using a method described in International Publication WO 2004/052191 that is an international application filed by the present applicant, an index by which the performance of discriminating between the 2 groups of colorectal cancer group and colorectal cancer-free group is maximized with regard to the discrimination of colorectal cancer was eagerly searched, and an index formula 4 was obtained among a plurality of indices having an equivalent performance.

$$Gln/Val - 0.83 \times Cit/ABA - 0.15 \times Thr/Glu \qquad \text{Index formula 4}$$

Figure 46:
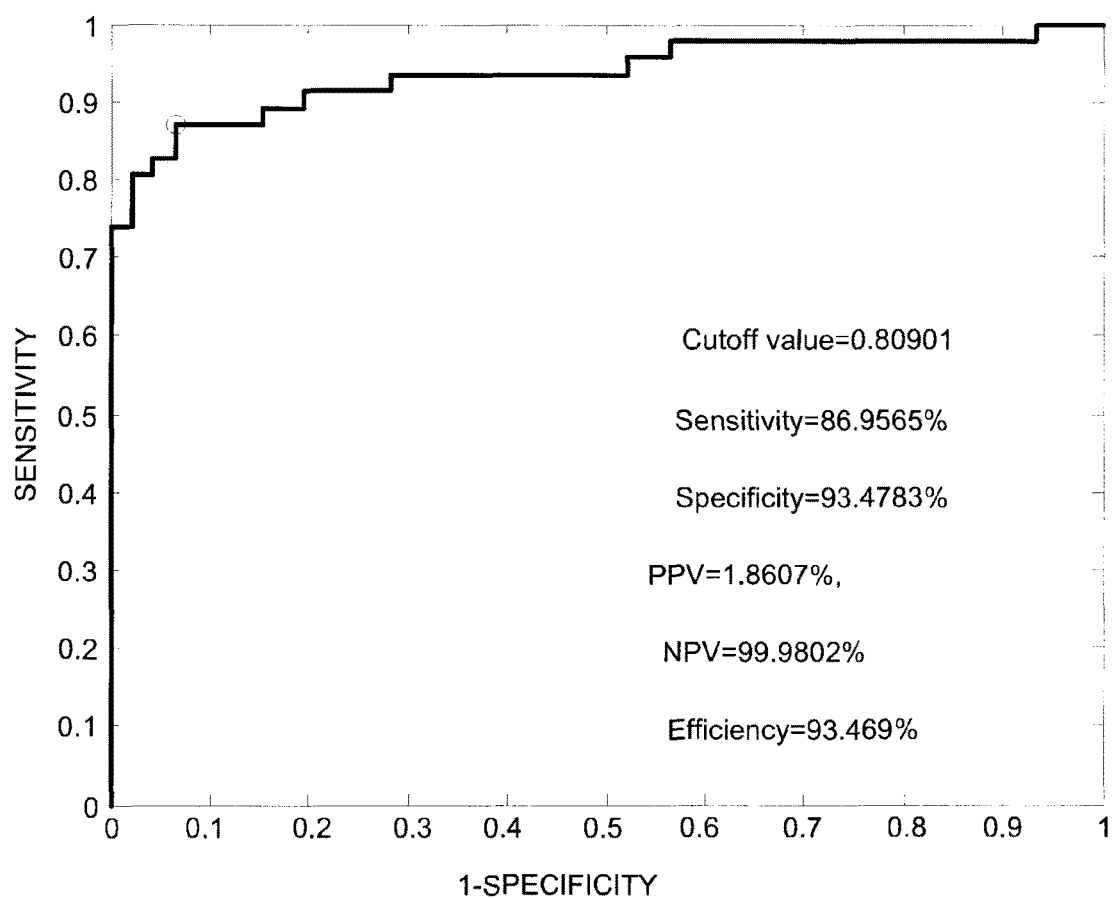
FIG. 46 is a graph showing an ROC curve for evaluation of diagnostic performance between 2 groups.

The performance for diagnosis of colorectal cancer based on the index formula 4 was evaluated based on the AUC of the ROC curve (FIG. 46) in connection with the discrimination between the 2 groups of colorectal cancer group and colorectal cancer-free group, and an AUC of 0.937±0.027 (95% confidence interval: 0.883 to 0.991) was obtained. When the optimum cutoff value for the discrimination between the 2 groups of colorectal cancer group and colorectal cancer-free group by the index formula 4 was determined assuming that the symptom prevalence of the colorectal cancer group was 0.142%, the cutoff value was 0.809, and a sensitivity of 86.96%, a specificity of 93.48%, a positive predictive value of 1.86%, a negative predictive value of 99.98%, and a correct diagnostic rate of 93.47% were obtained (FIG. 46). Thus, the index formula 4 was found to be a useful index with high diagnostic performance. In addition to that, a plurality of multivariate discriminants having a discrimination performance equivalent to that of the index formula 4 was obtained. Those multivariate discriminants are presented in FIG. 47 and FIG. 48. The respective values of the coefficients for the discriminants presented in FIG. 47 and FIG. 48 may be values multiplied by a real number, or values obtained by adding an arbitrary constant term.

EXAMPLE 8

The sample data used in Example 6 were used. An index by which the performance of discriminating between the 2 groups of colorectal cancer group and colorectal cancer-free group is maximized with regard to colorectal cancer was searched by logistic analysis (explanatory variable coverage method based on the BIC minimum criterion), and a logistic regression equation composed of Val, Glu, Thr, ABA, Gln and Pro (the numerical coefficients of the amino acid explanatory variables Val, Glu, Thr, ABA, Gln and Pro and the constant terms are, in the same order, −0.0417±0.0018, 0.0959±0.0043, −0.0388±0.0028, 0.1771±0.0102, 0.0094±0.0007, 0.0181±0.0014, and −0.8978±0.3672, respectively) was obtained as an index formula 5.

Figure 49:
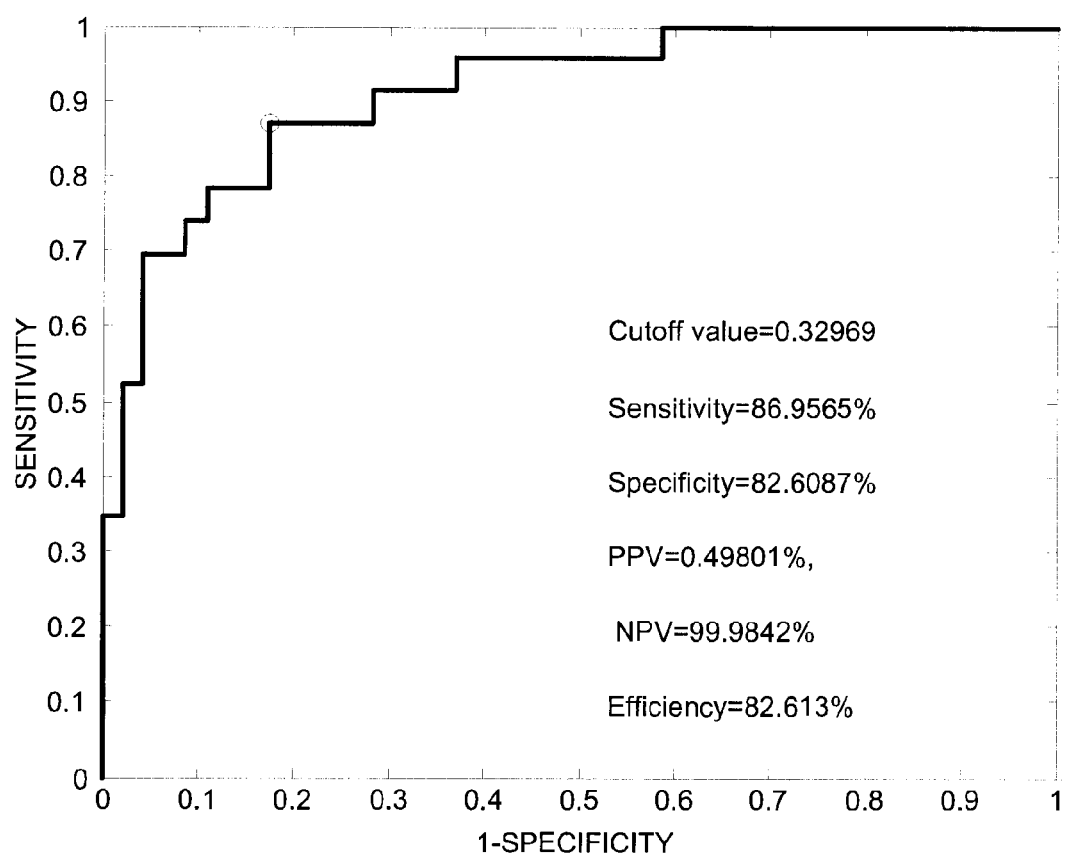
FIG. 49 is a graph showing an ROC curve for evaluation of diagnostic performance between 2 groups.

The performance for diagnosis of colorectal cancer based on the index formula 5 was evaluated based on the area under curve of the ROC curve (FIG. 49) in connection with the discrimination between the 2 groups of colorectal cancer group and colorectal cancer-free group, and an AUC of 0.899±0.034 (95% confidence interval: 0.833 to 0.966) was obtained. Thus, the index formula 5 was found to be a useful index with high diagnostic performance. When the optimum cutoff value for the discrimination between the 2 groups of colorectal cancer group and colorectal cancer-free group by the index formula 5 was determined assuming that the symptom prevalence of the colorectal cancer group was 0.142%, the cutoff value was 0.511, and a sensitivity of 80.4%, a specificity of 91.3%, a positive predictive value of 1.30%, a negative predictive value of 99.97%, and a correct diagnostic rate of 91.29% were obtained (FIG. 49). Thus, the index formula 5 was found to be a useful index with high diagnostic performance. In addition to that, a plurality of logistic regression equations having a discrimination performance equivalent to that of the index formula 5 was obtained. The logistic regression equations are presented in FIG. 50 and FIG. 51. The respective values of the coefficients for the equations presented in FIG. 50 and FIG. 51 may be values multiplied by a real number.

EXAMPLE 9

The sample data used in Example 6 were used. An index by which the performance of discriminating between the 2 groups of colorectal cancer group and colorectal cancer-free group is maximized with regard to colorectal cancer was searched by linear discriminant analysis (explanatory variable coverage method), and a linear discriminant function composed of Ile, His, Glu and ABA (the numerical coefficients of the amino acid explanatory variables Ile, His, Glu and ABA are, in the same order, 1±0.2, 0.692±0.027, −0.720±0.025, and −1.85±0.06, respectively) was obtained as an index formula 6.

Figure 52:
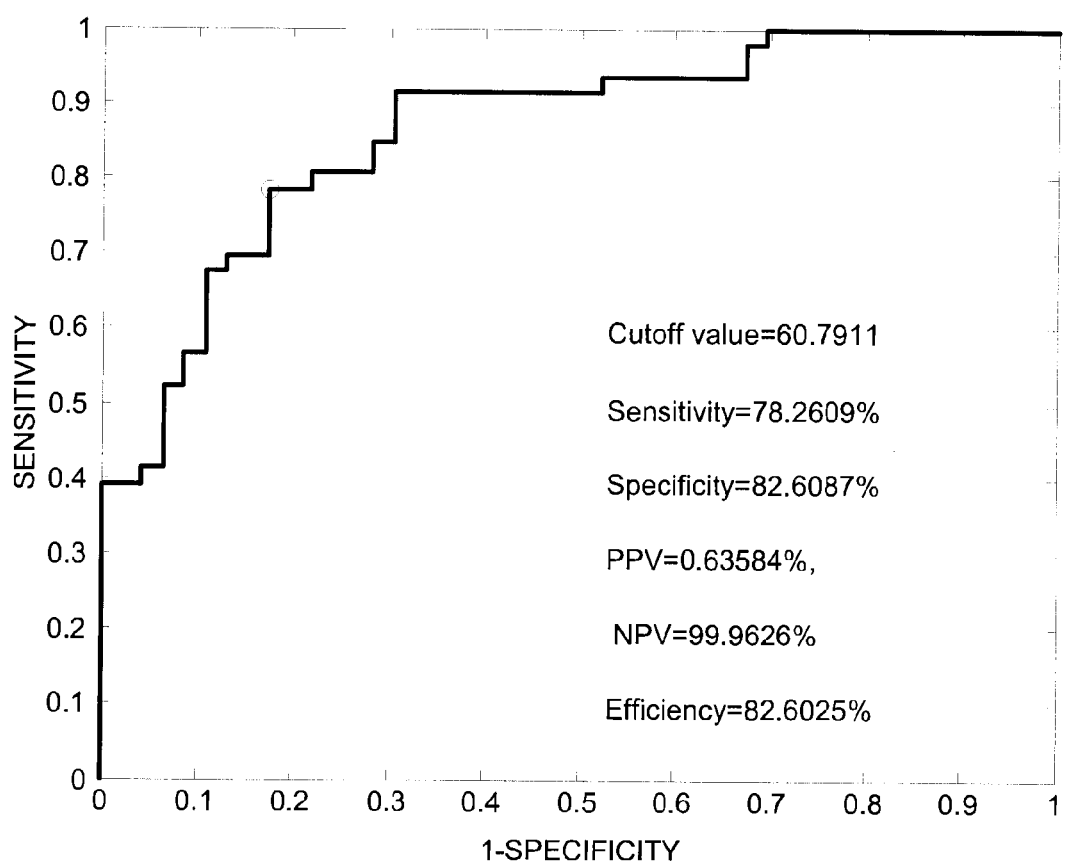
FIG. 52 is a graph showing an ROC curve for evaluation of diagnostic performance between 2 groups.

The performance for diagnosis of colorectal cancer based on the index formula 6 was evaluated based on the AUC of the ROC curve (FIG. 52) in connection with the discrimination between the 2 groups of colorectal cancer group and colorectal cancer-free group, and an AUC of 0.866±0.037 (95% confidence interval: 0.793 to 0.934) was obtained. Thus, the index formula 6 was found to be a useful index with high diagnostic performance. When the optimum cutoff value for the discrimination between the 2 groups of colorectal cancer group and colorectal cancer-free group by the index formula 6 was determined assuming that the symptom prevalence of the colorectal cancer group was 0.142%, the cutoff value was 60.79, and a sensitivity of 78.3%, a specificity of 82.6%, a positive predictive value of 0.64%, a negative predictive value of 99.96%, and a correct diagnostic rate of 82.6% were obtained (FIG. 52). Thus, the index formula 6 was found to be a useful index with high diagnostic performance. In addition to that, a plurality of linear discriminant functions having a discrimination performance equivalent to that of the index formula 6 was obtained. The linear discriminants are presented in FIG. 53 and FIG. 54. The respective values of the coefficients for the discriminants presented in FIG. 53 and FIG. 54 may be values multiplied by a real number, or values obtained by adding an arbitrary constant term.

EXAMPLE 10

The sample data used in Example 6 were used. All logistic regression equations for performing discrimination between the 2 groups of colorectal cancer group and colorectal cancer-free group with regard to colorectal cancer, were extracted by the explanatory variable coverage method. Assuming that the maximum value of the amino acid explanatory variables appearing in each equation was 6, the area under the ROC curve of every equation satisfying this condition was calculated. Here, measurement was made of the frequency of each amino acid appearing in the discriminant in which the area under the ROC curve was top 500 in rank, and as a result, Glu, ABA, Val, Phe, Leu, Gln, Ile and His were verified to be included in top 8 amino acids which are extracted at high frequency. Thus, it was made clear that a multivariate discriminant using these amino acids as explanatory variables has an ability to discriminate between the 2 groups of colorectal cancer group and colorectal cancer-free group (FIG. 55).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating colorectal cancer, comprising:
a concentration value criterion evaluating step of evaluating a colorectal cancer state in a subject to be evaluated, by a central processing unit (CPU) executing a colorectal cancer-evaluating program stored on a computer-readable recording medium, using at least a concentration value of at least Val contained in amino acid concentration data on the concentration value of the amino acid in blood of the subject;
wherein the concentration value criterion evaluating step further includes:
a discriminant value calculating step of calculating, by the CPU, a discriminant value that is a value of a multivariate discriminant, using at least both the concentration value of at least Val contained in the amino acid concentration data of the subject and the multivariate discriminant for evaluating the colorectal cancer state containing at least Val as an explanatory variable.

2. The method of evaluating colorectal cancer according to claim 1, wherein the concentration value criterion evaluating step further includes a concentration value criterion discriminating step of discriminating, by the CPU, between colorectal cancer and colorectal cancer-free in the subject, using at least the concentration value of at least Val contained in the amino acid concentration data of the subject.

3. The method of evaluating colorectal cancer according to claim 1, wherein the concentration value criterion evaluating step further includes a discriminant value criterion evaluating step of evaluating, by the CPU, the colorectal cancer state in the subject, using at least the discriminant value calculated at the discriminant value calculating step,
wherein the discriminant value criterion evaluating step further includes a discriminant value criterion discriminating step of discriminating, by the CPU, between colorectal cancer and colorectal cancer-free in the subject using at least the discriminant value calculated at the discriminant value calculating step.

4. The method of evaluating colorectal cancer according to claim 3, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

5. The method of evaluating colorectal cancer according to claim 4, wherein the multivariate discriminant is the logistic regression equation containing Orn, Gln, Trp and Cit as the explanatory variables, the linear discriminant containing Orn, Gln, Trp, Phe, Cit and Tyr as the explanatory variables, the logistic regression equation containing Val, Glu, Thr, ABA, Gln and Pro as the explanatory variables, or the linear discriminant containing Ile, His, Glu and ABA as the explanatory variables.

6. The method of evaluating colorectal cancer of claim 1, wherein the concentration value used contains at least Val and Ile.

7. The method of evaluating colorectal cancer of claim 1, wherein the concentration value used contains at least Val, Ile, and Met.

8. The method of evaluating colorectal cancer according to claim 1, wherein the concentration value criterion evaluating step further includes a discriminant value criterion evaluating step of evaluating, by the CPU, the colorectal cancer state in the subject, using at least the discriminant value calculated at the discriminant value calculating step.

9. A colorectal cancer-evaluating apparatus comprising a CPU executing a colorectal cancer-evaluating program stored on a computer-readable recording medium,
wherein the CPU is configured to:
calculate a discriminant value that is a value of a multivariate discriminant, using at least both a concentration value of at least Val contained in amino acid concentration data on the concentration value of the amino acid in blood of a subject to be evaluated and the multivariate discriminant for evaluating a colorectal cancer state containing at least Val as an explanatory variable.

10. The colorectal cancer-evaluating apparatus according to claim 9, wherein the CPU is further configured to evaluate the colorectal cancer state in the subject, using at least the discriminant value,
wherein the CPU is further configured to discriminate between colorectal cancer and colorectal cancer-free in the subject using at least the discriminant value.

11. The colorectal cancer-evaluating apparatus according to claim 10, wherein the multivariate discriminant is any one of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

12. The colorectal cancer-evaluating apparatus according to claim 11, wherein the multivariate discriminant is the logistic regression equation containing Orn, Gln, Trp and Cit as the explanatory variables, the linear discriminant containing Orn, Gln, Trp, Phe, Cit and Tyr as the explanatory variables, the logistic regression equation containing Val, Glu, Thr, ABA, Gln and Pro as the explanatory variables, or the linear discriminant containing Ile, His, Glu and ABA as the explanatory variables.

13. The colorectal cancer-evaluating apparatus according to claim 9, wherein the CPU is configured to prepare the multivariate discriminant, using at least colorectal cancer state information containing the amino acid concentration data and colorectal cancer state index data on an index for indicating the colorectal cancer state,
wherein the CPU is further configured to:
prepare a candidate multivariate discriminant that is a candidate of the multivariate discriminant, using at least a predetermined discriminant-preparing method from the colorectal cancer state information;
verify the candidate multivariate, using at least a predetermined verifying method; and
select an explanatory variable of the candidate multivariate discriminant using at least a predetermined explanatory variable selecting method, thereby selecting a combination of the amino acid concentration data contained in the colorectal cancer state information used in preparing the candidate multivariate discriminant, and wherein the multivariate discriminant is prepared by selecting the candidate multivariate discriminant used as the multivariate discriminant, from a plurality of the candidate multivariate discriminants, using at least the verification results accumulated by executing the colorectal cancer-evaluating program by the CPU.

14. The colorectal cancer-evaluating apparatus of claim 9, wherein the concentration value used contains at least Val and Ile.

15. The colorectal cancer-evaluating apparatus of claim 9, wherein the concentration value used contains at least Val, Ile, and Met.

16. The colorectal cancer-evaluating apparatus according to claim 9, wherein the CPU is further configured to evaluate the colorectal cancer state in the subject, using at least the discriminant value.

17. A colorectal cancer-evaluating method carried out with an information processing apparatus comprising a CPU executing a colorectal cancer-evaluating program stored on a computer-readable recording medium, the CPU is configured to:
(i) calculate a discriminant value that is a value of a multivariate discriminant, using at least both a concentration value of at least Val contained in amino acid concentration data on the concentration value of the amino acid in blood of a subject to be evaluated and the multivariate discriminant for evaluating a colorectal cancer state containing at least Val as an explanatory variable.

18. The colorectal cancer-evaluating method according to claim 17, wherein the CPU is further configured to evaluate the colorectal cancer state in the subject, using at least the discriminant value,
wherein the CPU is further configured to discriminate between colorectal cancer and colorectal cancer-free in the subject using at least the discriminant value.

19. The colorectal cancer-evaluating method according to claim 18, wherein the multivariate discriminant is anyone of a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

20. The colorectal cancer-evaluating method according to claim 19, wherein the multivariate discriminant is the logistic regression equation containing Orn, Gln, Trp and Cit as the explanatory variables, the linear discriminant containing Orn, Gln, Trp, Phe, Cit and Tyr as the explanatory variables, the logistic regression equation containing Val, Glu, Thr, ABA, Gln and Pro as the explanatory variables, or the linear discriminant containing Ile, His, Glu and ABA as the explanatory variables.

21. The colorectal cancer-evaluating method according to claim 17, wherein the CPU is configured to prepare the multivariate discriminant, using at least colorectal cancer state information containing the amino acid concentration data and colorectal cancer state index date on an index for indicating the colorectal cancer state,
wherein the CPU is further configured to:
prepare a candidate multivariate discriminant that is a candidate of the multivariate discriminant, using at least a predetermined discriminant-preparing method from the colorectal cancer state information;
verify the candidate multivariate discriminant, using at least a predetermined verifying method; and
select an explanatory variable of the candidate multivariate discriminant using at least a predetermined explanatory variable selecting method, thereby selecting a combination of the amino acid concentration data contained in the colorectal cancer state information used in preparing the candidate multivariate discriminant, and wherein the multivariate discriminant is prepared by selecting the candidate multivariate discriminant used as the multivariate discriminant from a plurality of the candidate multivariate discriminants, using at least the verification results accumulated by executing the colorectal cancer-evaluating program by the CPU.

22. The colorectal cancer-evaluating method of claim 17, wherein the concentration value used contains at least Val and Ile.

23. The colorectal cancer-evaluating method of claim 17, wherein the concentration value used contains at least Val, Ile, and Met.

24. The colorectal cancer-evaluating method according to claim 17, wherein the CPU is further configured to evaluate the colorectal cancer state in the subject, using at least the discriminant value.

25. A colorectal cancer-evaluating system comprising a colorectal cancer evaluating apparatus comprising a CPU executing a colorectal cancer evaluating program stored on a computer-readable recording medium, and a terminal apparatus configured to provide amino acid concentration data on a concentration value of an amino acid in blood of a subject to be evaluated, wherein the apparatuses are connected to each other communicatively via a network,
wherein the terminal apparatus includes:
an amino acid concentration data-sending unit configured to transmit the amino acid concentration data of the subject to the colorectal cancer-evaluating apparatus; and
a result-receiving unit configured to receive a discriminant value that is a value of a multivariate discriminant or an evaluation result of a colorectal cancer state transmitted from the colorectal cancer-evaluating apparatus,
wherein the CPU is configured to:
receive the amino acid concentration data of the subject transmitted from the terminal apparatus;
calculate the discriminant value, using at least both the concentration value of at least Val contained in the amino acid concentration data of the subject and the multivariate discriminant for evaluating a colorectal cancer state containing at least Val as an explanatory variable or calculate a discriminant value that is a value of a multivariate discriminant, using at least both the concentration value of at least Val contained in the amino acid concentration data of the subject and the multivariate discriminant for evaluating the colorectal cancer state containing at least Val as an explanatory variable, and evaluate the colorectal cancer state in the subject using at least the discriminant value; and
transmit the discriminant value or the evaluating result of the subject to the terminal apparatus.

26. The colorectal cancer-evaluating system of claim 25, wherein the concentration value used contains at least Val and Ile.

27. The colorectal cancer-evaluating system of claim 25, wherein the concentration value used contains at least Val, Ile, and Met.

28. A colorectal cancer-evaluating program installed in a non-transitory computer-readable recording medium, wherein the program is executed by a CPU configured to:
(i) calculate a discriminant value that is a value of a multivariate discriminant, using at least both a concentration value of at least Val contained in amino acid concentration data on the concentration value of the amino acid in blood of a subject to be evaluated and the multivariate discriminant for evaluating a colorectal cancer state containing at least Val as an explanatory variable.

29. The colorectal cancer-evaluating program of claim 28, wherein the concentration value used contains at least Val and Ile.

30. The colorectal cancer-evaluating program of claim 28, wherein the concentration value used contains at least Val, Ile, and Met.

31. The colorectal cancer-evaluating program according to claim 28, wherein the CPU is further configured to evaluate the colorectal cancer state in the subject, using at least the discriminant value.

32. A terminal apparatus comprising:
a result-obtaining unit configured to obtain a discriminant value that is a value of a multivariate discriminant or an evaluation result of a colorectal cancer state,
wherein the discriminant value is calculated using at least both a concentration value of at least Val contained in amino acid concentration data on the concentration value of the amino acid in blood of a subject to be evaluated and the multivariate discriminant for evaluating a colorectal cancer state containing at least Val as an explanatory variable or the evaluation result is the result of evaluating the colorectal cancer state in a subject to be evaluated using at least a discriminant value that is a value of a multivariate discriminant, wherein the discriminant value is calculated using at least both a concentration value of at least Val contained in amino acid concentration data on the concentration value of the amino acid in blood of the subject and the multivariate discriminant for evaluating the colorectal cancer state containing at least Val as an explanatory variable.

33. The terminal apparatus of claim 32, wherein the concentration value used contains at least Val and Ile.

34. The terminal apparatus of claim 32, wherein the concentration value used contains at least Val, Ile, and Met.

35. The terminal apparatus according to claim 32, wherein the terminal apparatus is communicatively connected via a network to a colorectal cancer-evaluating apparatus comprising a CPU executing a colorectal cancer-evaluating program stored on a computer-readable recording medium to calculate the discriminant value or evaluate the colorectal cancer state,
wherein the result-obtaining unit is configured to receive the discriminant value or the evaluation result transmitted from the colorectal cancer-evaluating apparatus.

36. A colorectal cancer-evaluating apparatus comprising a CPU executing a colorectal cancer-evaluating program stored on a computer-readable recording medium, wherein the apparatus is communicatively connected via a network to a terminal apparatus configured to provide amino acid concentration data on a concentration value of an amino acid in blood of a subject to be evaluated,
wherein the CPU is configured:
receive the amino acid concentration data of the subject transmitted from the terminal apparatus;
calculate a discriminant value that is a value of a multivariate discriminant, using at least both the concentration value of at least Val contained in the amino acid concentration data of the subject and the multivariate discriminant for evaluating a colorectal cancer state containing at least Val as an explanatory variable; or calculate a discriminant value that is a value of a multivariate discriminant, using at least both the concentration value of at least Val contained in the amino acid concentration data of the subject and the multivariate discriminant for evaluating a colorectal cancer state containing at least Val as an explanatory variable and evaluate the colorectal cancer state in the subject using at least the discriminant value; and
transmit the discriminant value or an evaluation result of the colorectal cancer state of the subject to the terminal apparatus.

37. The colorectal cancer-evaluating apparatus of claim 36, wherein the concentration value used contains at least Val and Ile.

38. The colorectal cancer-evaluating apparatus of claim 36, wherein the concentration value used contains at least Val, Ile, and Met.

39. A colorectal cancer-evaluating apparatus comprising a CPU executing a colorectal cancer evaluating program stored on a computer-readable recording medium, wherein the CPU is configured to:
evaluate a colorectal cancer state in a subject to be evaluated, using at least a discriminant value that is a value of a multivariate discriminant,
wherein the discriminant value is calculated using at least both a concentration value of at least Val contained in amino acid concentration data on the concentration value of the amino acid in blood of the subject and the multivariate discriminant for evaluating the colorectal cancer state containing at least Val as an explanatory variable.

40. A colorectal cancer-evaluating method carried out with an information processing apparatus comprising a CPU executing a colorectal cancer evaluating program stored on a computer-readable recording medium, the CPU is configured to:
evaluate a colorectal cancer state in a subject to be evaluated, using at least a discriminant value that is a value of a multivariate discriminant,
wherein the discriminant value is calculated using at least both a concentration value of at least Val contained in amino acid concentration data on the concentration value of the amino acid in blood of the subject and the multivariate discriminant for evaluating the colorectal cancer state containing at least Val as an explanatory variable.

41. A colorectal cancer-evaluating program installed in a non-transitory computer-readable recording medium, wherein the program is executed by a CPU configured to:
evaluate a colorectal cancer state in a subject to be evaluated, using at least a discriminant value that is a value of a multivariate discriminant,
wherein the discriminant value is calculated using at least both a concentration value of at least Val contained in amino acid concentration data on the concentration value of the amino acid in blood of the subject and the multivariate discriminant for evaluating the colorectal cancer state containing at least Val as an explanatory variable.

42. A method of evaluating colorectal cancer, comprising:
a discriminant value calculating step of calculating, by a CPU executing a colorectal cancer-evaluating program stored on a computer-readable recording medium, a discriminant value that is a value of a multivariate discriminant, using at least both a concentration value of at least Val contained in amino acid concentration data on the concentration value of the amino acid in blood of a subject to be evaluated and the multivariate discriminant for evaluating a colorectal cancer state containing at least Val as an explanatory variable.

43. The method of evaluating colorectal cancer according to claim 42, wherein the method further includes a discriminant value criterion evaluating step of evaluating, by the CPU, the colorectal cancer state in the subject, using at least the discriminant value calculated at the discriminant value calculating step.

44. A method of evaluating colorectal cancer, comprising:
a discriminant value criterion evaluating step of evaluating, by a CPU executing a colorectal cancer-evaluating program stored on a computer-readable recording medium, a colorectal cancer state in a subject to be evaluated, using at least a discriminant value that is a value of a multivariate discriminant,
wherein the discriminant value is calculated using at least a concentration value of at least Val contained in amino acid concentration data on the concentration value of the amino acid in blood of the subject and the multivariate discriminant for evaluating the colorectal cancer state containing at least Val as an explanatory variable.

* * * * *